(12) United States Patent
Nihalani

(10) Patent No.: US 10,010,441 B2
(45) Date of Patent: Jul. 3, 2018

(54) GASTRIC RESTRICTION DEVICES FOR TREATING OBESITY

(71) Applicant: Onciomed, Inc., Irvine, CA (US)

(72) Inventor: Raj Nihalani, Irvine, CA (US)

(73) Assignee: ReShape Lifesciences, Inc., San Clemente, CA (US)

( * ) Notice: Subject to any disclaimer, the term of this patent is extended or adjusted under 35 U.S.C. 154(b) by 726 days.

(21) Appl. No.: 14/571,144

(22) Filed: Dec. 15, 2014

(65) Prior Publication Data

US 2016/0166417 A1    Jun. 16, 2016
US 2017/0202693 A9    Jul. 20, 2017

Related U.S. Application Data

(63) Continuation of application No. 12/474,254, filed on May 28, 2009, now Pat. No. 8,911,346, which is a continuation-in-part of application No. 12/328,979, filed on Dec. 5, 2008, now Pat. No. 8,357,081.

(51) Int. Cl.
    *A61F 5/00*    (2006.01)

(52) U.S. Cl.
    CPC .......... *A61F 5/0063* (2013.01); *A61F 5/0066* (2013.01)

(58) Field of Classification Search
    CPC .......................... A61F 5/0063; A61F 5/0066
    See application file for complete search history.

(56) References Cited

U.S. PATENT DOCUMENTS

2005/0119674 A1 *    6/2005    Gingras ................ A61F 5/0003
                                                              606/151

* cited by examiner

*Primary Examiner* — Christine H Matthews
*Assistant Examiner* — Joshua D Lannu
(74) *Attorney, Agent, or Firm* — Snell & Wilmer LLP

(57) ABSTRACT

A gastric restraining device for treating excessive weight or obesity in mammals. The gastric restraining device includes an elastomeric sheet configured to be placed around a stomach of a mammal, an ablation device attached to the elastomeric sheet, the ablation device configured to emit energy toward an outer surface of the stomach when the elastomeric sheet is placed around the stomach, and an energy device coupled to the ablation device to generate the energy and to transfer the energy to the ablation device.

12 Claims, 56 Drawing Sheets

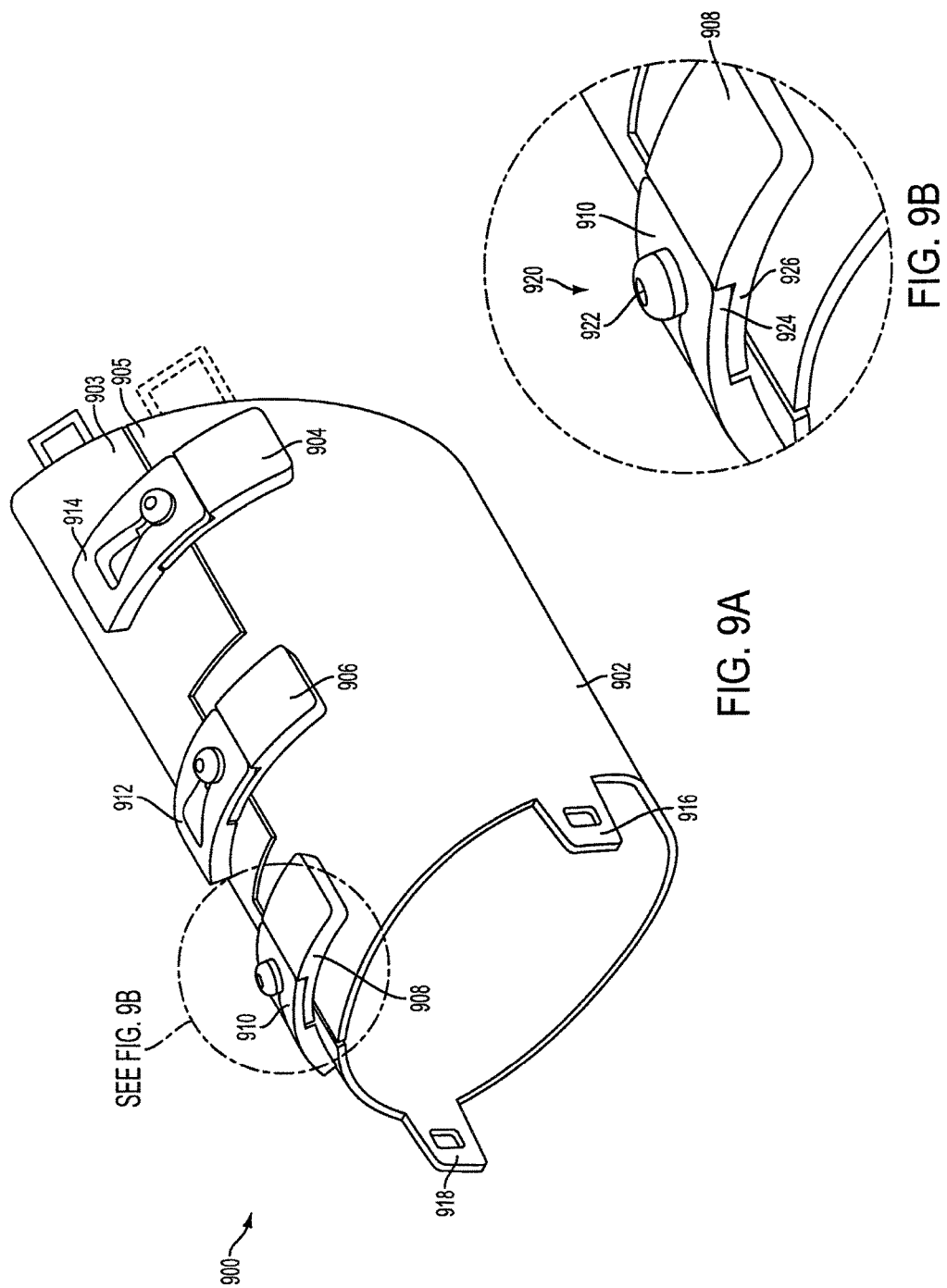

GASTRIC RESTRICTION DEVICES FOR TREATING OBESITY

CROSS-REFERENCE TO RELATED APPLICATIONS

This application is a continuation of U.S. patent application Ser. No. 12/474,254, entitled "Gastric Restriction Devices with Fillable Chambers and Ablation Means for Treating Obesity," filed May 28, 2009 and now U.S. Pat. No. 8,911,346, which is a continuation-in-part of U.S. patent application Ser. No. 12/328,979, entitled "Method and Apparatus for Gastric Restriction of the Stomach to Treat Obesity," filed Dec. 5, 2008, now U.S. Pat. No. 8,357,081, the entire contents of both applications are hereby incorporated by reference herein for all purposes.

BACKGROUND

Field

The invention relates to a method and apparatus for treating obesity and controlling weight gain in mammals, and more specifically, to an inflatable gastric skirt placed around the stomach to cause a reduced desire for eating for treating obesity and controlling weight gain in mammals.

Description of the Related Art

Extreme obesity is a major illness in the United States and other developed countries. More than half of Americans are overweight, while nearly one-third are categorized as obese. Obesity is the accumulation of excess fat on the body, and is defined as having a body mass index (BMI) of greater than 30. Many serious long-term health consequences are associated with obesity, such as, hypertension, diabetes, coronary artery disease, stroke, congestive heart failure, venous disease, multiple orthopedic problems and pulmonary insufficiency with markedly decreased life expectancy.

Medical management of obesity including dietary, psychotherapy, medications and behavioral modification techniques have yielded extremely poor results in terms of treating obesity. Several surgical procedures have been tried which have bypassed the absorptive surface of the small intestine or have been aimed at reducing the stomach size by either partition or bypass. These procedures have been proven both hazardous to perform in morbidly obese patients and have been fraught with numerous life-threatening postoperative complications. Moreover, such operative procedures are often difficult to reverse.

One procedure for treating morbid obesity is referred to as a "biliopancreatic diversion." Biliopancreatic diversion surgery is a reduction of the stomach volume and a diversion of food from the stomach to the final segment of the small intestine, bypassing the beginning and middle portions of the small intestine to limit the amount of nutrients and calories absorbed by the body. This procedure removes about one half of the stomach, and then connects the stomach to the last 250 cm of the small intestine. Some disadvantages of this surgery include patients suffering from protein malnutrition, anemia, gastric retention, diarrhea, abdominal bloating, and intestinal obstruction.

Another bariatric surgery, "gastric bypass," is a bypass connecting the lower compartment of the stomach to the initial portion of the small intestine. This procedure limits the amount of food that can be ingested at one sitting and reduces absorption of food across the small intestine. In addition to surgical complications, patients may also suffer from acute gastric dilation, anastomotic leak, anemia, and dumping syndrome.

Yet another bariatric surgical procedure is "vertical-banded gastroplasty," which restricts the volume of the stomach by using staples. In this procedure, staples are placed in the upper stomach region to create a small pouch with a narrow outlet to the remaining portion of the stomach. A band is placed around the narrow outlet to provide support and inhibit stretching of the stomach. In addition to surgical complications, patients undergoing this procedure may suffer from vomiting, ulcers, band erosion, and leaks.

Recently, minimally invasive procedures and devices which create a feeling of early satiety have been introduced into the marketplace in an attempt to address some of the issues above. The LAP-BAND® is a band which encircles the stomach at the region of the fundus-cardia junction; it is a restrictive procedure similar to stomach stapling. The procedure requires general anesthesia, a pneumoperitoneum, muscle paralysis, and extensive dissection of the stomach at the region of the gastro esophageal junction. The procedure also requires continual adjustment of the band, or restriction of a portion of the device. Although less invasive than other bariatric surgical procedures and potentially reversible, the LAP-BAND® does not reduce the volume of the stomach by any great extent and some patients report a feeling of hunger most of the time. Furthermore, once implanted, the LAP-BAND®, although it is adjustable by percutaneous means, may require many iterative adjustments before it is optimally positioned. In addition, the port used to adjust the LAP-BAND® is left inside the patient's body.

Therefore, there is a need for minimally-invasive procedures and devices that eliminate the above-mentioned drawbacks of conventional methods and devices that are currently being used to treat obesity.

SUMMARY

In one embodiment, the invention includes a gastric restraining device for treating excessive weight or obesity in mammals. The gastric restraining device includes a skirt having an interior surface and an exterior surface having a surface area of at least 14 square centimeters, a chamber attached to the interior surface of the skirt and capable of holding a fluid, the chamber configured to be positioned around a stomach of a mammal so that the chamber covers a portion of a greater curvature of the stomach and a portion of a lesser curvature of the stomach, and a tube connected to the chamber for delivering the fluid into and out of the chamber to cause the chamber to expand and contract.

In one embodiment, the invention includes a gastric restraining device for treating excessive weight or obesity in mammals. The gastric restraining device includes an elastomeric sheet configured to be placed around a stomach of a mammal, an ablation device attached to the elastomeric sheet, the ablation device configured to emit energy toward an outer surface of the stomach when the elastomeric sheet is placed around the stomach, and an energy device coupled to the ablation device to generate the energy and to transfer the energy to the ablation device.

In one embodiment, the invention includes a method for treating excessive weight or obesity in mammals by gastric constriction or restraining. The method includes using an endoscopic device, inserting a bougie into the stomach adjacent to a lesser curvature of the stomach. The method also includes tucking a portion of a greater curvature of the stomach toward the bougie which results in a first untucked stomach portion, a second untucked stomach portion, and a cavity between the first untucked stomach portion and the second untucked stomach portion. The method also includes using a ligation device, inserting a ligature through the first untucked portion, the cavity, and the second untucked portion and using the endoscopic device, removing the bougie from the stomach.

BRIEF DESCRIPTION OF THE DRAWINGS

These and other embodiments of the invention will be discussed with reference to the following exemplary and non-limiting illustrations, in which like elements are numbered similarly, and where:

FIG. 9A is a view of a folded gastric skirt with locking clips;
FIG. 9B is a view of a locking clip for a gastric skirt.

DETAILED DESCRIPTION

Throughout this description, the term gastric "skirt" is used to refer to a device made of a flexible, semi-flexible, or minimally stretchable material that can be tightly wrapped around portions of a stomach to provide constriction to the stomach. The term "skirt" can be used interchangeably with "vest", "wrap", "wrapping", "wrapper", "bandage", "blanket", "cape", "cloak", "cover", "jacket", "envelope", and equivalents thereof.

Figure 1A:
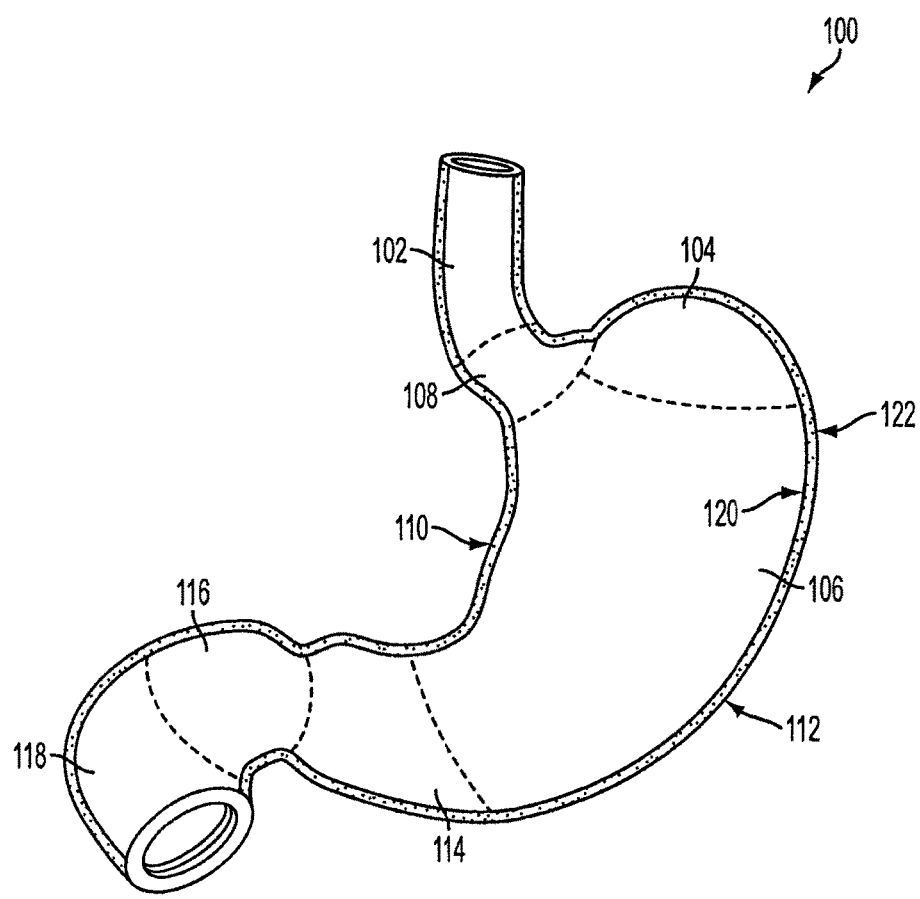
FIG. 1A is a view of a stomach of a mammal.

FIG. 1A is a view of a stomach 100 of a mammal (e.g., human). As shown in FIG. 1A, the stomach 100 has at least two curvatures, a lesser curvature 110 and a greater curvature 112. The cardia or proximal stomach 108 is located in the upper left portion of the stomach 100 and serves as the junction between the esophagus 102 and the body of the stomach 106. The fundus 104 is located in the upper right portion of the stomach 100. The lower portion of the stomach 100 is known as the distal stomach and includes the antrum 114 and the pylorus 116. The antrum 114 is where food is mixed with gastric juices. The pylorus 116 has a muscular pyloric sphincter that acts as a valve to control emptying of the stomach contents into the proximal segment of the small intestine 118 (partially shown). The inner lining 120 of the stomach 100 separates the body 106 from the outer wall 122.

The invention is directed to a gastric skirt that is placed around the stomach 100 by a healthcare professional, such as a surgeon, a bariatric surgeon or a gastrointestinal specialist trained in laparoscopic and/or general surgery procedures. The gastric skirt can be positioned using a routine laparoscopic procedure or a conventional open-surgical procedure. Furthermore, the gastric skirt can be placed around the stomach 100 using newer techniques, methods and procedures for laparoscopic surgery.

The invention can be utilized in conjunction with the LAP-BAND® procedure and/or other post-gastric bypass procedures such as vertical gastric sleeve procedure treatments that provide reinforcement and restraining devices to prevent further expansion or re-expansion of the stomach 100.

Figure 1B:
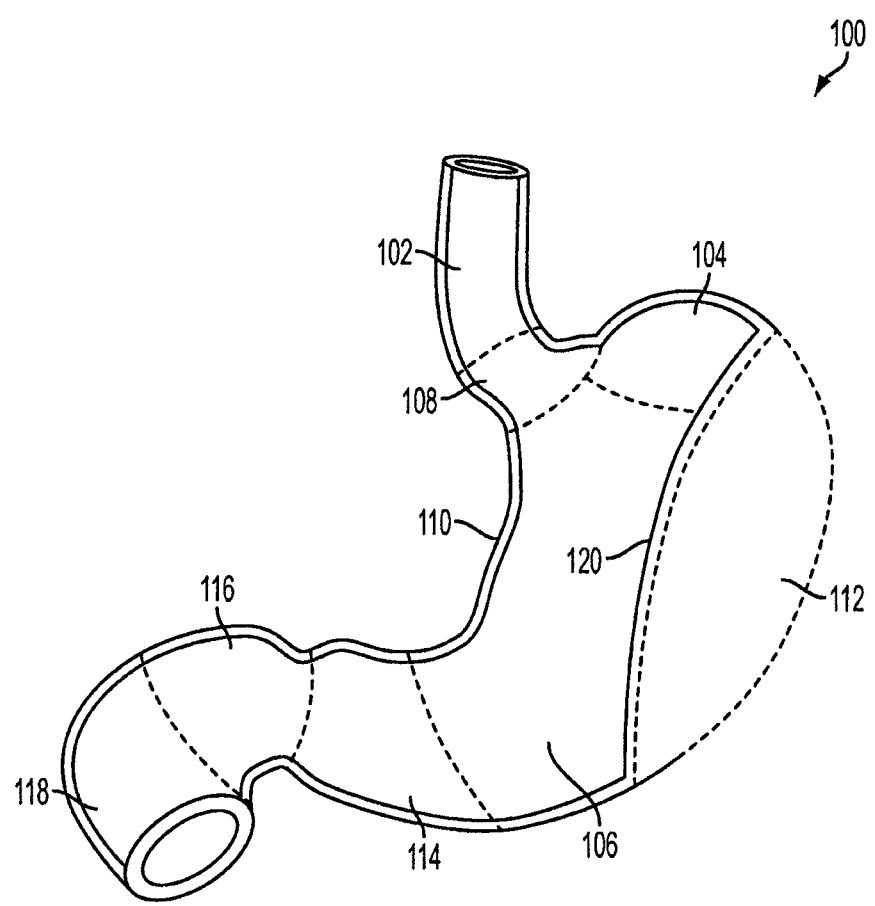
FIG. 1B is a view of a partially tucked-in stomach of a mammal.

FIG. 1B is a view of a partially tucked-in stomach 100 of a human. Prior to placing the gastric skirt around the stomach 100, a linear portion of the greater curvature 112 is tucked inwards into the stomach 100. As shown in FIG. 1B, the inner lining 120 is depressed within the stomach 100 as a result of the tucking procedure, and the tucked-in portion occupies space within the stomach 100. Thus, the internal volume of the stomach 100 is substantially decreased, creating a ridge like effect, leading to the slowing of the passage of food, and thus less food consumption, while still enabling absorption of vital fluids and nutrients (unlike a gastric bypass procedure). In addition, the internal volume of the fundus 104 is reduced.

In another embodiment, the tucked-in portion of the stomach 100 may be a linear portion of the lesser curvature 110, a portion of the body 106, or a portion of the fundus 104, not along either the greater curvature 112 or the lesser curvature 110. Therefore, any portion of the stomach 100 may be tucked-in and wrapped using the gastric skirts disclosed herein.

Figure 2A:
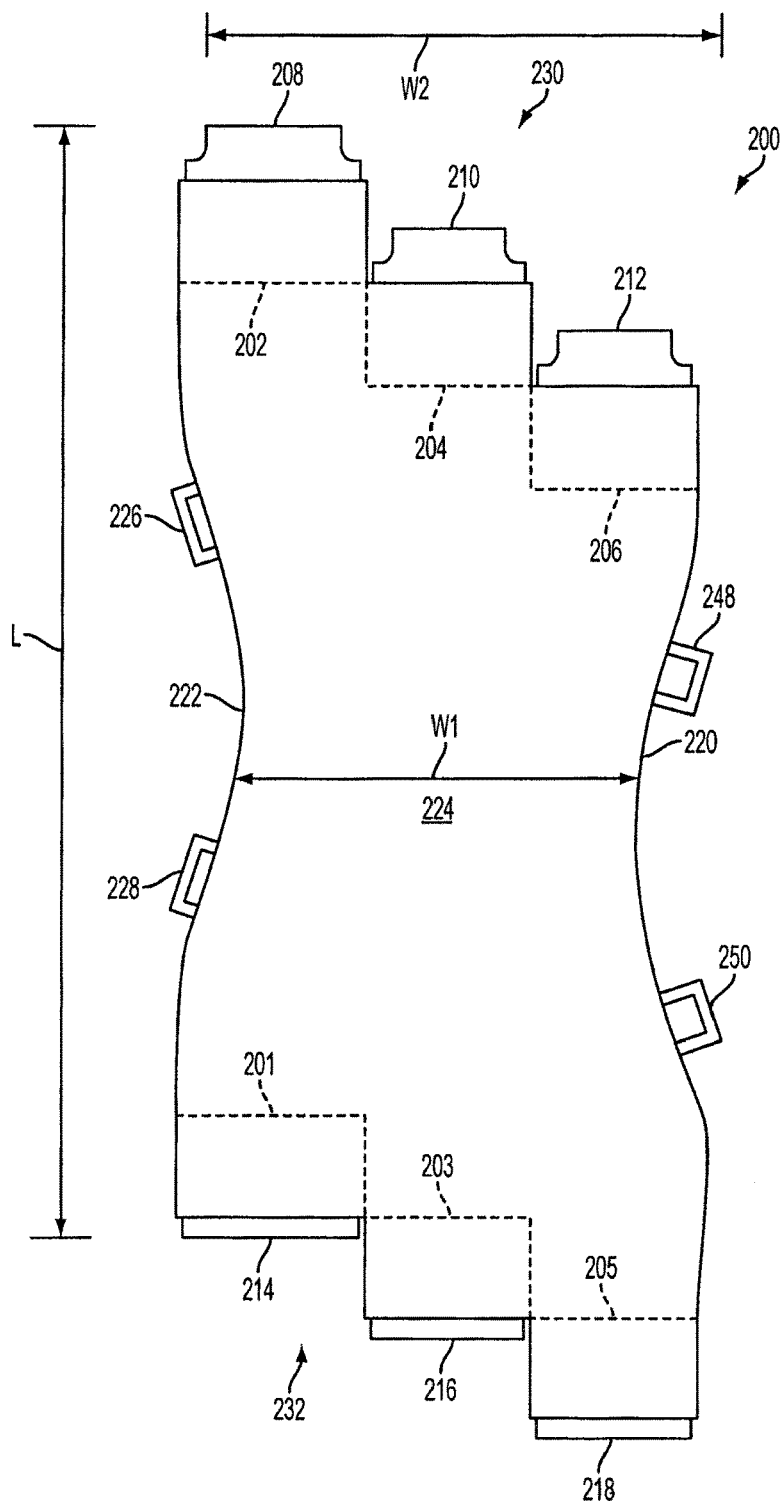
FIG. 2A is a view of a laid-open gastric skirt.

FIG. 2A is a view of a laid-open gastric skirt 200. The gastric skirt 200 may be formed as a sheet 224 prior to being wrapped around a patient's stomach. For illustrative purposes, the gastric skirt 200 has a left side 232, a right side 230, a bottom portion 220, and a top portion 222. Each connector 208, 210, and 212 may be offset or staggered relative to its adjacent connector. Similarly, each receiver 214, 216, and 218 may be offset or staggered relative to its adjacent receiver. In one embodiment, each offset may be approximately 1-3 centimeters. The bottom portion 220 and the top portion 222 may have an inward curved or concave edge. The gastric skirt 200 may have a length L of approximately 6-16 centimeters, a central width W1 of approximately 3-7 centimeters, and an outer width W2 of approximately 6-10 centimeters.

In a preferred embodiment, the length L is at least 8 centimeters, the central width W1 is at least 4 centimeters, and the outer width W2 is at least 7 centimeters.

The gastric skirt 200 may have a staggered step design and may be formed in the shape of a parallelogram when laid-open, where the opposing ends of the gastric skirt 200 interconnect in a stepped fashion when the gastric skirt 200 is folded. For example, step element 201 is staggered relative to immediately opposing step element 202. Likewise, step element 203 and step element 205 are staggered relative to their immediately opposing step elements 204 and 206, respectively. When the gastric skirt 200 is wrapped or folded into position around a patient's stomach 100, the opposing step elements interconnect with each other, forming the end at the greater curvature 112 and the gastric skirt 200 is formed into a conical cylindrical shape, which is described in more detail below.

Attached to each step element is a male connector or a female receiver or vice versa. In the exemplary embodiment, a male connector 208 is attached to a female receiver 214. When the gastric skirt 200 is folded into position, the male connector 208 couples with the female receiver 214. The male connectors 210 and 212 couple with the female receivers 216 and 218, respectively, when the gastric skirt 200 is wrapped or folded into position around the stomach. In other embodiments, the gastric skirt 200 may have one set of connectors (e.g., a single male connector 208 and a single female receiver 214) or two sets of connectors (e.g., 2 male connectors 208 and 210 and 2 female receivers 214 and 216). The connectors can be of various shapes and sizes, and are not limited to the connector design shown in FIG. 2A. Furthermore, the connectors can be positioned at various locations on the gastric skirt 200, and are not limited to being positioned at the left side 232 and the right side 230 of the gastric skirt 200.

The gastric skirt 200 has a bottom portion 220 that is inward curving. Opposite the bottom portion 220, the gastric skirt 200 has a top portion 222 that is inward curving. When the gastric skirt 200 is folded into position, the bottom and top portions 220 and 222 come into contact with the lesser curvature 110 and provide the gastric skirt 200 with a contoured, conical shape. The conical shape allows the gastric skirt 200 to properly fit around the stomach 100.

Furthermore, one or more optional connectors or wings 226 and 228 are attached to the top portion 222 of the gastric skirt 200 and one or more optional connectors or wings 248 and 250 are attached to the bottom portion 220 of the gastric skirt 200. The connectors or wings 226 and 228 may be used to attach the gastric skirt 200 to collar connector straps (shown in FIGS. 10A, 10B, and 11). The connectors or wings 248 and 250 may be used to attach the gastric skirt 200 to connector straps (shown in FIG. 11).

The body or sheet 224 of the gastric skirt 200 is relatively flexible, or semi-flexible, and may be made of an elastic polymer ("elastomer"), such as, but not limited to, silicone, polypropylene, polyethylene terephthalate, polytetrafluoroethylene, polyaryletherketone, nylon, fluorinated ethylene propylene, polybutester, or any combination thereof. Furthermore, the elastomer may be non-porous. Alternatively, the elastomer may be microporous or porous to allow for better expansibility and oxygenation and for tissue ingrowth to better hold the gastric skirt 200 in place.

In a preferred embodiment, the elastomer is silicone. Silicone provides an ample amount of rigidity, while still providing flexibility to accommodate changes in stomach shape and size during peristalsis. A silicone body may be preferred over a porous body, as larger pores may allow the stomach muscles or tissue to seep through and grow onto the outside of the body 224. This overgrowth of the stomach through the body 224 may make it difficult to remove the gastric skirt 200 from the patient if needed. Furthermore, the silicone allows some expandability of the stomach 100, which is the stomach's natural function. Thus, the gastric skirt 200 allows the stomach to accommodate some gases and larger pieces of food or meat.

Alternatively, more rigid materials, such as Teflon®, Dacron®, ePTFE or wire mesh may be used if they provide an adequate level of flexibility, and do not significantly irritate or erode the stomach surface. That is, the gastric skirt 200 should be relatively flexible, as a very rigid stomach wrap may cause discomfort to the patient, as well as injury to the stomach and other gastric organs. The gastric skirt 200 is tightly positioned around the tucked-in stomach so little to no open space is provided between the gastric skirt 200 and the outer surface of the stomach.

In another embodiment, the body 224 of the gastric skirt 200 may be made of a biodegradable and absorbable polymer or copolymer, such as, but not limited to, polyglycolic acid (PGA), polylactic acid (PLA), polycaprolactone, polyhydroxyalkanoate, various thermoplastic materials, or any combination thereof. Once placed around the stomach 100, the gastric skirt 200 stays in position for a predetermined amount of time. After the predetermined amount of time has elapsed, the gastric skirt 200 may be absorbed by the patient's bodily fluids, eliminating the need for a second procedure to remove the gastric skirt 100. In this particular embodiment, the entire gastric skirt 200, including the male connectors and the female receivers, are made of a biodegradable material.

The staggered step design allows the gastric skirt 200, including all of the connectors and receivers, to be rolled into a highly compact fashion. In one embodiment, the gastric skirt 200 can be placed around a patient's stomach using a routine laparoscopic procedure, referred to as a laparoscopy. During a laparoscopy, the gastric skirt 200 is inserted into the patient via a trocar through a hole made in the patient's abdomen. The staggered step design minimizes the diameter of the gastric skirt 200 when it is rolled for insertion through the trocar. That is, the connectors and receivers are not positioned on top of each other in the rolled position to minimize the thickness for insertion.

In another embodiment, male connectors are connected to their respective female receivers with an elastic material. For example, male connector 208 is connected to female receiver 214 with a strap made from an elastic material. The strap is positioned within an internal channel that runs lengthwise from the left side 232 to the right side 230 within the gastric skirt 200. The strap is preferably made of a more elastic material than the gastric skirt 200 so that the connectors can accommodate peristalsis and movement of the stomach. This embodiment allows stress to be placed on the strap rather than the gastric skirt 200, thereby preventing the gastric skirt 200 from being overstretched due to peristalsis.

Figure 2B:
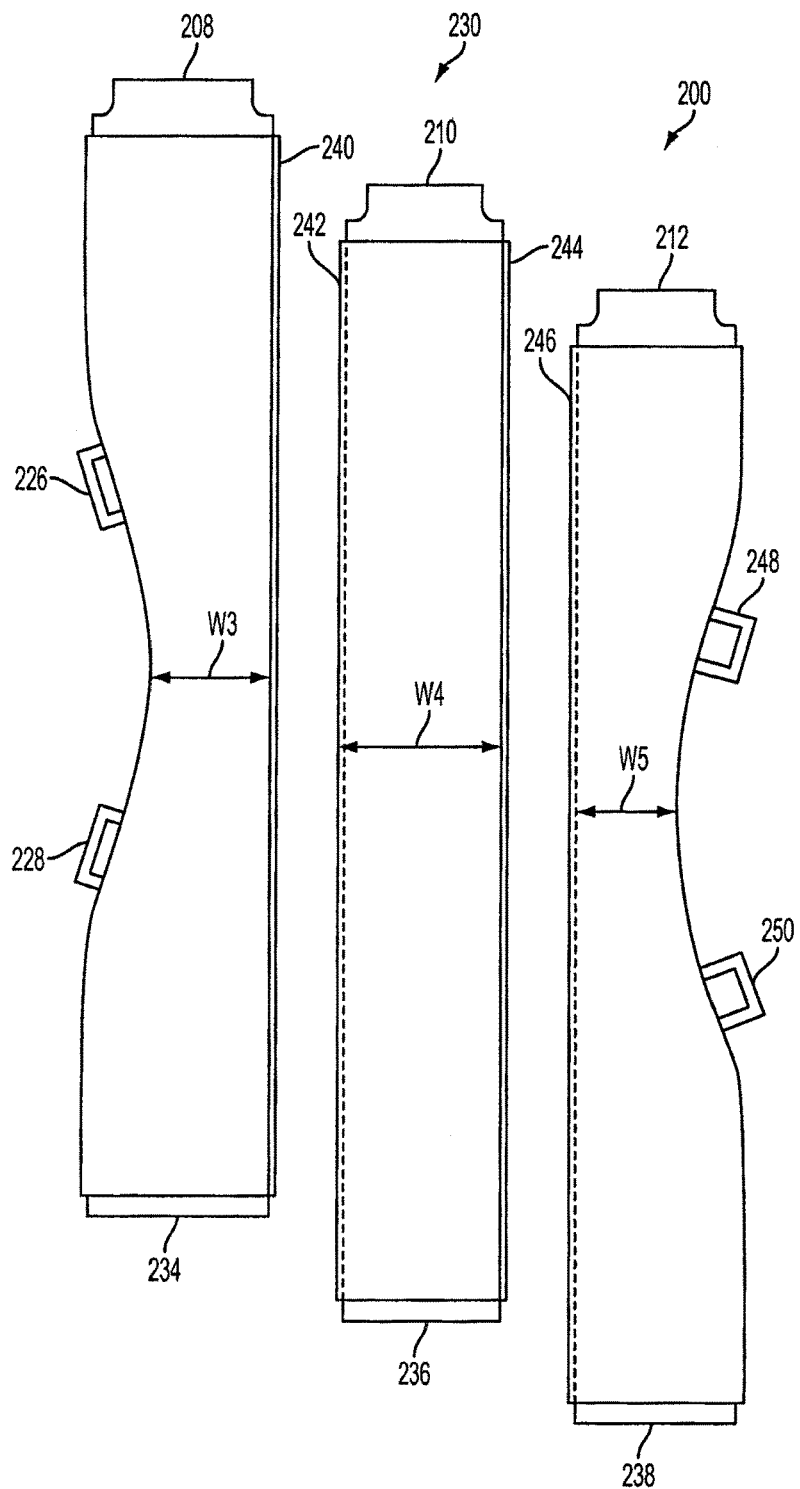
FIG. 2B is a view of a modular laid-open gastric skirt.

FIG. 2B is a view of a modular laid-open gastric skirt 200. The modular gastric skirt 200 may have two or more rectangular strips or modules 234, 236, and 238. Each strip may have a ridge 240 (and 244) and/or a groove 242 (and 246) for attachment to adjacent strips. The ridge 240 securely fits into the groove 242 along the length of each strip to prevent unwanted detachment of adjacent strips and any in-growth of tissue between adjacent strips. Some advantages of the strips include each strip can be inserted separately and the size of the gastric skirt 200 can be adjusted at the time of surgery to account for the amount of tucking, size and orientation of the stomach 100. The modular gastric skirt 200 may have a width W3 of approximately 1-3 centimeters, a width W4 of approximately 1-4 centimeters, and a width W5 of approximately 1-3 centimeters. The widths may vary depending on the size and amount of tucking needed. The modular gastric skirt 200 may have a length L of approximately 6-16 centimeters.

In an embodiment, the modular gastric skirt 200 may utilize only two of the rectangular strips or modules 234, 236, and 238. For example, module 234 can be connected to module 236 to form the modular gastric skirt 200. Alternatively, module 234 can be connected to module 238 to form the modular gastric skirt 200.

Figure 3:
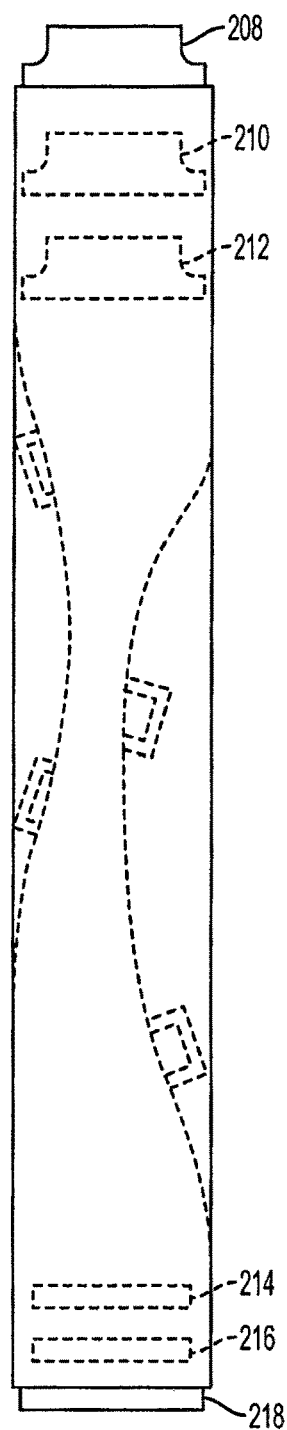
FIG. 3 is a view of a rolled gastric skirt.

FIG. 3 is a view of a rolled gastric skirt 300. The gastric skirt 300 is tightly rolled so that it can be inserted through a trocar as described above or other means. The staggered step design allows the male connectors 208, 210, and 212, and the female connectors 214, 216, and 218 to not overlap with each other when the gastric skirt 300 is rolled. By not overlapping, the male connectors 208, 210, and 212 and the female receivers 214, 216, and 218 are evenly flush with each other, so the diameter of the rolled gastric skirt 300 is minimized. Similarly, the connectors, the cardia collar and the antral collar may be passed through the trocar into the stomach for connection to the gastric skirt 200.

Figure 4:
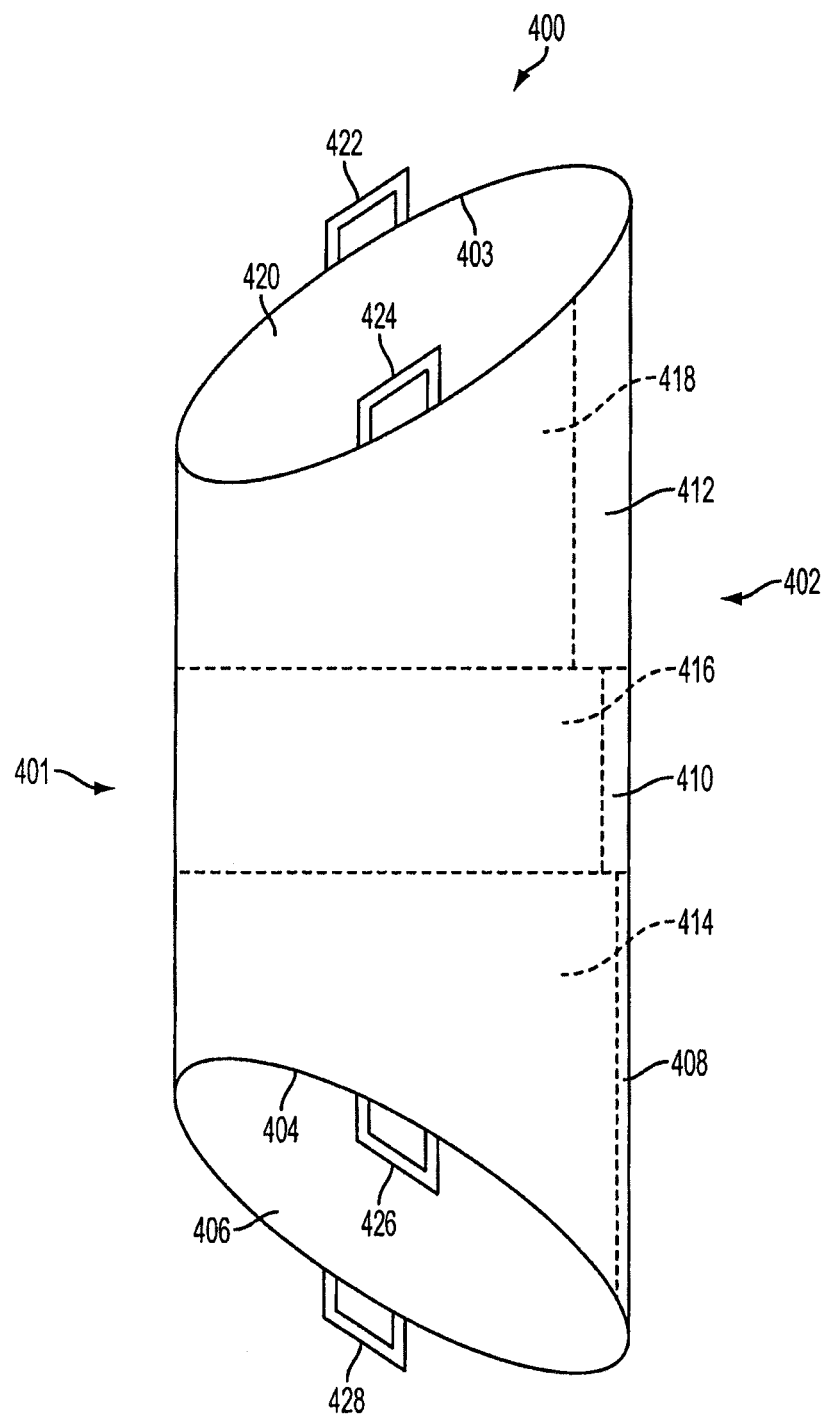
FIG. 4 is a view of a folded conical cylinder-shaped gastric skirt.

FIG. 4 is a view of a folded conical cylinder-shaped gastric skirt 400. As shown, step elements 412, 410, and 408 are each connected to their immediately opposing step elements 418, 416, and 414, respectively, to form a conical cylinder-shaped gastric skirt 400. In an embodiment, the outer or upper curvature 403 has a convex shape and is outwardly curving. The inner or lower curvature 404 has a concave shape and is inwardly curving. The conical cylinder shape allows the gastric skirt 400 to properly fit around and contact the stomach. The upper portion of the stomach 100 is covered by the gastric skirt 400 near the upper curvature 403, as the upper portion of the stomach has a larger diameter than the lower portion of the stomach. The lower portion of the stomach is covered by the gastric skirt 400 near the lower curvature 404.

The diameter of the upper curvature opening 420 (i.e., cardia end) and the lower curvature opening 406 (i.e., antral end) are similar. The gastric skirt 400 can be a "one-size fits all" design, where a single-sized gastric skirt 400 is used for all or most stomach sizes. To adjust to a "one-size fits all" gastric skirt 400, the stomach is tucked in per physician's preference and the gastric skirt 400 is simply tightened accordingly when it is being positioned around the stomach.

Furthermore, the one or more optional wings 422 and 424 are attached on the circumference of the upper curvature 403. The wings 422 and 424 are used to attach the gastric skirt 400 to collar connector straps (see also FIGS. 10A and 10B). Similarly, the circumference of the lower curvature 404 can also have one or more wings 426 and 428 attached. In another embodiment, the gastric skirt 400 can have no wings attached, or wings only on one side, either on the upper curvature 403 or the lower curvature 404.

In another embodiment, a healthcare professional can estimate or measure the size of the patient's stomach beforehand. Using this measurement, the gastric skirt 400 can be tailored to provide a customized fit (for example, 10-30% smaller in diameter than the measurement to accommodate the tuck). The prior measurement reduces the risk of overtucking or overstretching or damaging the gastric skirt 400 when it is being positioned around the stomach, and can allow for a smooth and even customized fit (see also FIGS. 5A, 5B, and 5C).

This conical cylinder design allows a single gastric skirt to properly hold various portions of the stomach, even though the stomach may vary in size throughout. The use of a single gastric skirt reduces the complexity of the system and reduces the possibility of complications which may arise due to uneven pressure resulting from multiple skirts around the stomach. Alternatively, multiple, separately-sized gastric skirts, such as, one for a larger portion of the stomach, and one for a smaller portion of the stomach, may be used.

Figure 5A:
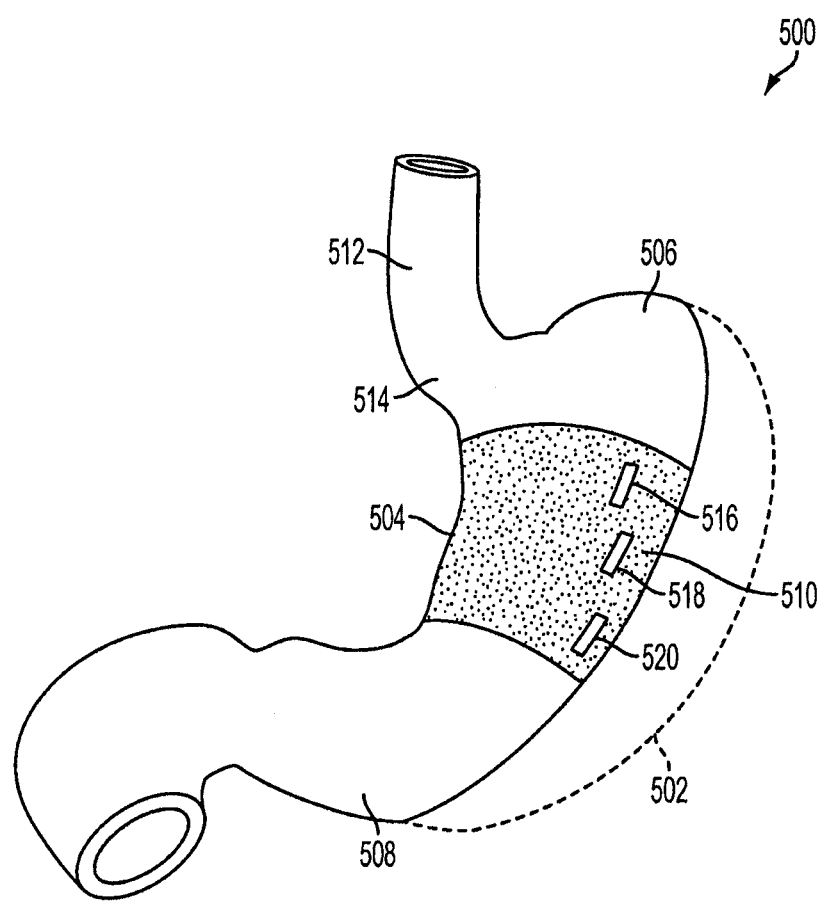
FIG. 5A is a view of a gastric skirt placed in position around a stomach.

FIG. 5A is a view of a gastric skirt 500 placed in position around a stomach. The gastric skirt 510 is designed to cover substantially all of the greater or outer curvature 502, and substantially all of the lesser or inner curvature 504. As shown in FIG. 5A, a portion of the fundus 506 and the antrum/pylorus 508 may be tucked or covered or restricted by the gastric skirt 510.

In another embodiment, the gastric skirt 510 can be designed to cover a smaller portion of the greater curvature 502 and/or a smaller portion of the lesser curvature 504, instead of covering the entire respective surfaces. Furthermore, the gastric skirt 510 can be designed to cover other surfaces of the stomach in addition to the greater curvature 502 and/or the lesser curvature 504. For example, the gastric skirt 510 may have a larger surface area and cover the fundus 506 and/or the antrum/pylorus 508, or portions thereof, in addition to portions of the greater curvature 502 and/or the lesser curvature 504.

Unlike conventional gastric-restraint devices, such as the LAP-BAND®, the gastric skirt 510 is not placed between the cardia 514 and the fundus 506 forming a pouch. Furthermore, the gastric skirt 510 is not placed around the esophagus 512. As described above, the gastric skirt 510 is instead fitted or positioned around the body of the stomach 500 (i.e., around surfaces of the greater curvature 502 and the lesser curvature 504 of the stomach 500).

Figure 5B:
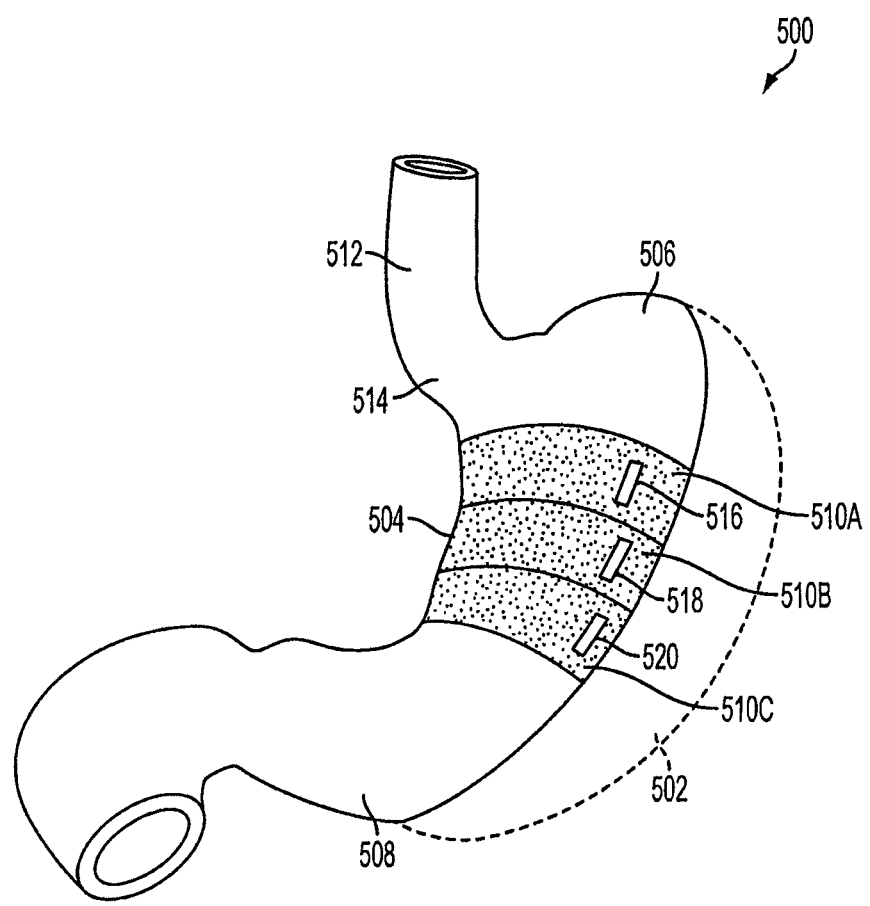
FIG. 5B is a view of a modular gastric skirt placed in position around a stomach.

FIG. 5B is a view of a modular gastric skirt placed in position around a stomach 500. The modular skirt 510 is shown as three strips 510A, 510B, and 510C connected to one another. The male and female connectors are shown as 516, 518, and 520, respectively.

Figure 5C:
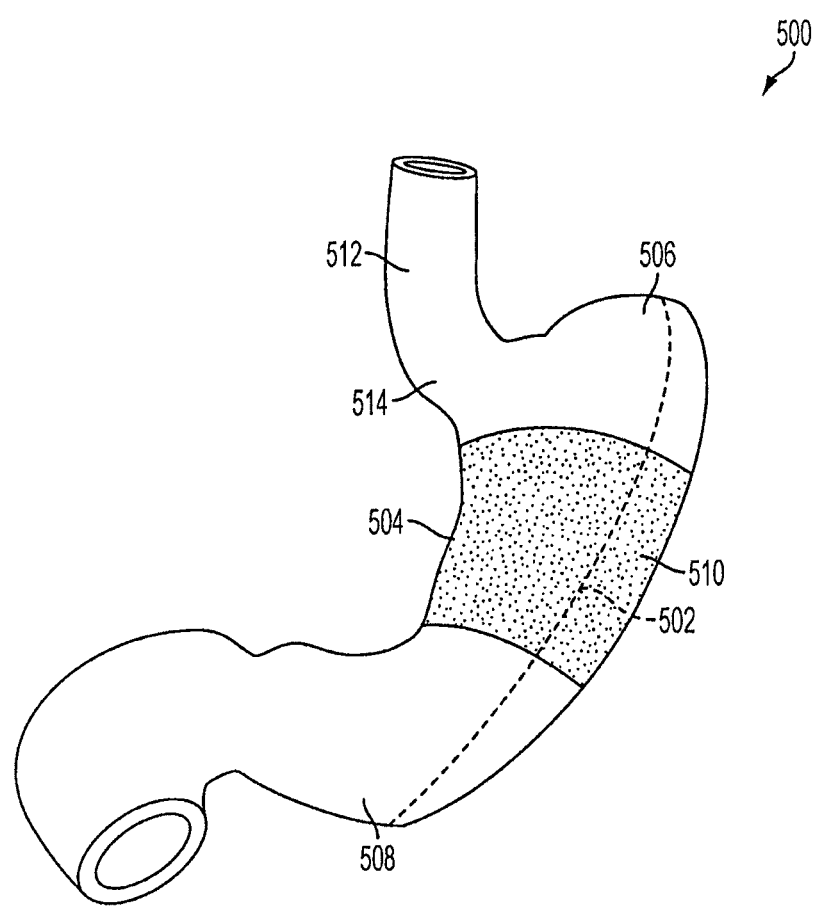
FIG. 5C is a view of a gastric skirt placed in position around a stomach that shows a tucked-in portion of the stomach.

FIG. 5C is a view of a gastric skirt 510 placed in position around a stomach 500 that shows a tucked-in portion of the stomach. In this example, the greater curvature 502 is tucked into the body of the stomach 500 and the gastric skirt 510 is placed around the tucked stomach to secure the tucked portion in place. The tucked portion is pushed into the body of the stomach, thus reducing the internal volume of the stomach.

Figure 6:
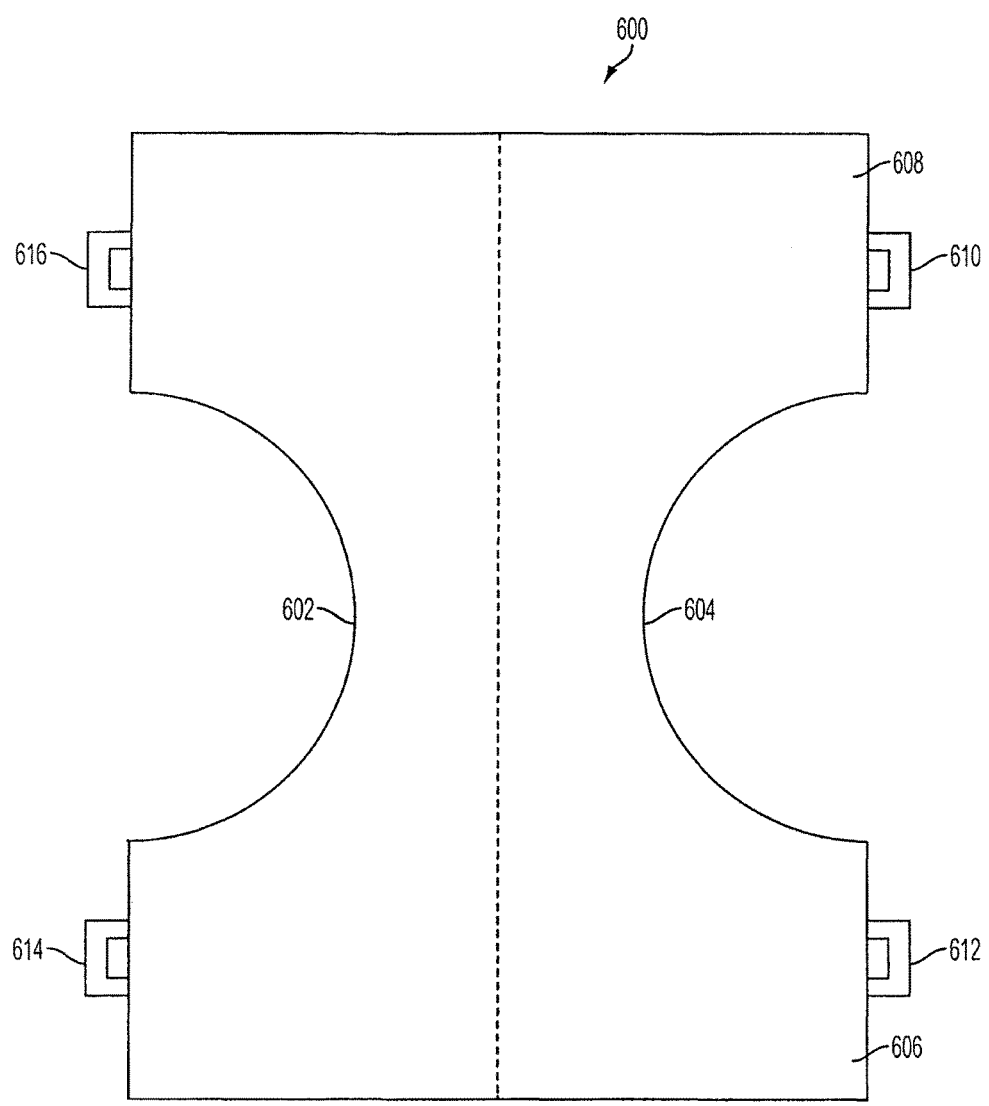
FIG. 6 is a view of a laid-open butterfly-shaped gastric skirt.

FIG. 6 is a view of a laid-open butterfly-shaped gastric skirt 600. The gastric skirt 600 has an indentation 602 on one side and an indentation 604 on the opposing side. The proximal end 606 and the distal end 608 can include connectors and receivers, respectively, so that when the gastric skirt 600 is folded, the proximal end 606 and the distal end 608 can be connected together.

Indentations 602 and 604 can be any shape such as an ellipse, oval, hourglass, or semicircular shape as shown in FIG. 6. For example, each of the indentations 602 and 604 can be formed in the shape of a square, a triangle, an oval, a semi-circle, an ellipse, a wave, a curve, or any other shape that creates an indentation. The size of each indentation 602 and 604 can be varied in order to provide an optimal fit around the stomach. Indentations 602 and 604 do not necessarily have to be the same shape or size as one another.

Furthermore, optional wing 610 is attached on one substantially horizontal portion adjacent to indentation 604, and optional wing 612 is attached on the other substantially horizontal portion adjacent to indentation 604. The wings 610 and 612 are used to attach the gastric skirt 600 to collar connector straps (shown in FIGS. 10A, 10B, and 11). Similarly, the side of the gastric skirt 600 with indentation 602 has wings 614 and 616 attached. In another embodiment, the gastric skirt 600 can have no wings attached, or wings only on one side. The dashed line indicates that the gastric skirt 600 can have two or more modular pieces connected to one another similar to that shown in FIG. 2B.

Figure 7:
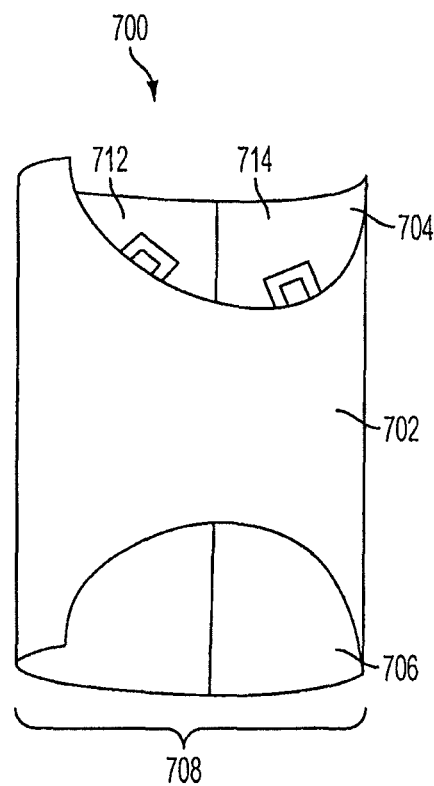
FIG. 7 is a view of a folded butterfly-shaped gastric skirt.

FIG. 7 is a view of a folded butterfly or step ladder-shaped gastric skirt 700. Once the distal end 712 and the proximal end 714 are connected together by coupling the connectors and receivers, a narrow surface 702 fits the lesser curvature of the stomach and is formed on one side of the gastric skirt 700 between indentation 704 and indentation 706. On the side opposite to the narrow surface 702 is the wide surface 708 which fits the greater curvature of the stomach.

In this embodiment, the narrow surface 702 of the butterfly-shaped gastric skirt 700 can be used to cover the lesser curvature of the stomach. Likewise, the broad surface 708 can be used to cover the greater curvature of the stomach.

In another embodiment, instead of having connectors and receivers to couple the gastric skirt 700, the distal end 712 and the proximal end 714 can be sutured or stapled together.

Figure 8A:
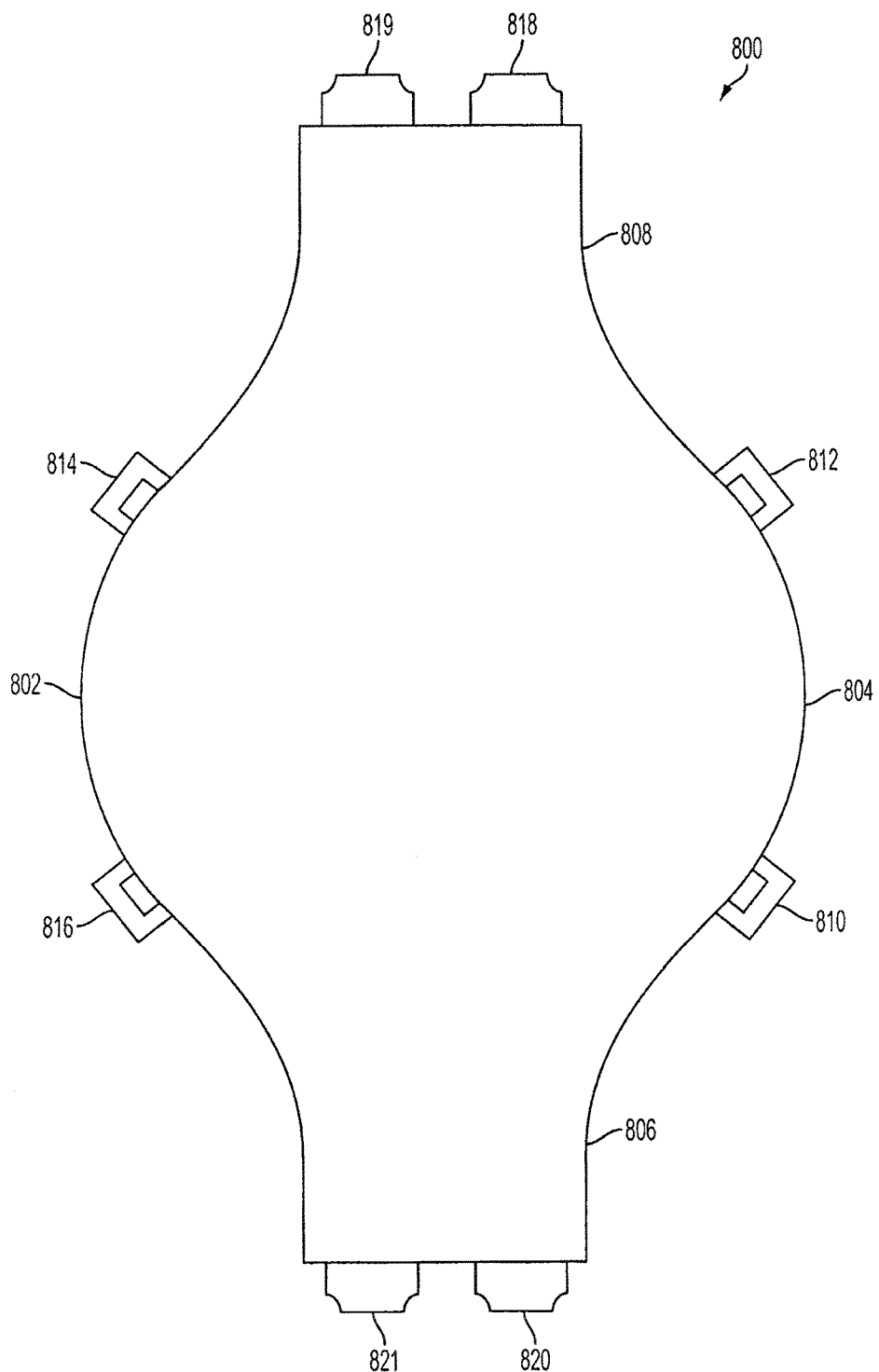
FIG. 8A is a view of a laid-open oval or pear-shaped skirt.

FIG. 8A is a view of a laid-open oval or pear-shaped skirt 800. In this embodiment, the gastric skirt 800 has a protrusion 802 on one side and a protrusion 804 on the opposing side. The proximal end 806 includes female connectors 820 and 821, and the distal end 808 includes male connectors 818 and 819. Therefore, when the gastric skirt 800 is folded, the proximal end 806 and the distal end 808 can be connected by securing the male connectors 818 and 819 into the female connector 820 and 821, respectively. In an embodiment, the width of the proximal end 806 and the distal end 808 is from about 4 centimeters to about 6 centimeters and the width between the protrusion 802 and the protrusion 804 is from about 8 centimeters to about 14 centimeters.

Outward protrusions 802 and 804 can be any shape, and not limited to, an oval, pear or semicircular shape as shown in FIG. 8A. For example, each of the outward protrusions 802 and 804 can be formed in the shape of a square, a triangle, or any other shape. The size of each outward protrusion 802 and 804 can also be varied in order to provide an optimal fit around the stomach. Furthermore, the outward protrusions 802 and 804 do not necessarily have to be the same shape or size as one another. Optional wings 810 and 812 may be attached to outward protrusion 804, and optional wings 814 and 816 may be attached to outward protrusion 802. In another embodiment, the gastric skirt 800 can have no wings attached, or wings only on one side.

Figure 8B:
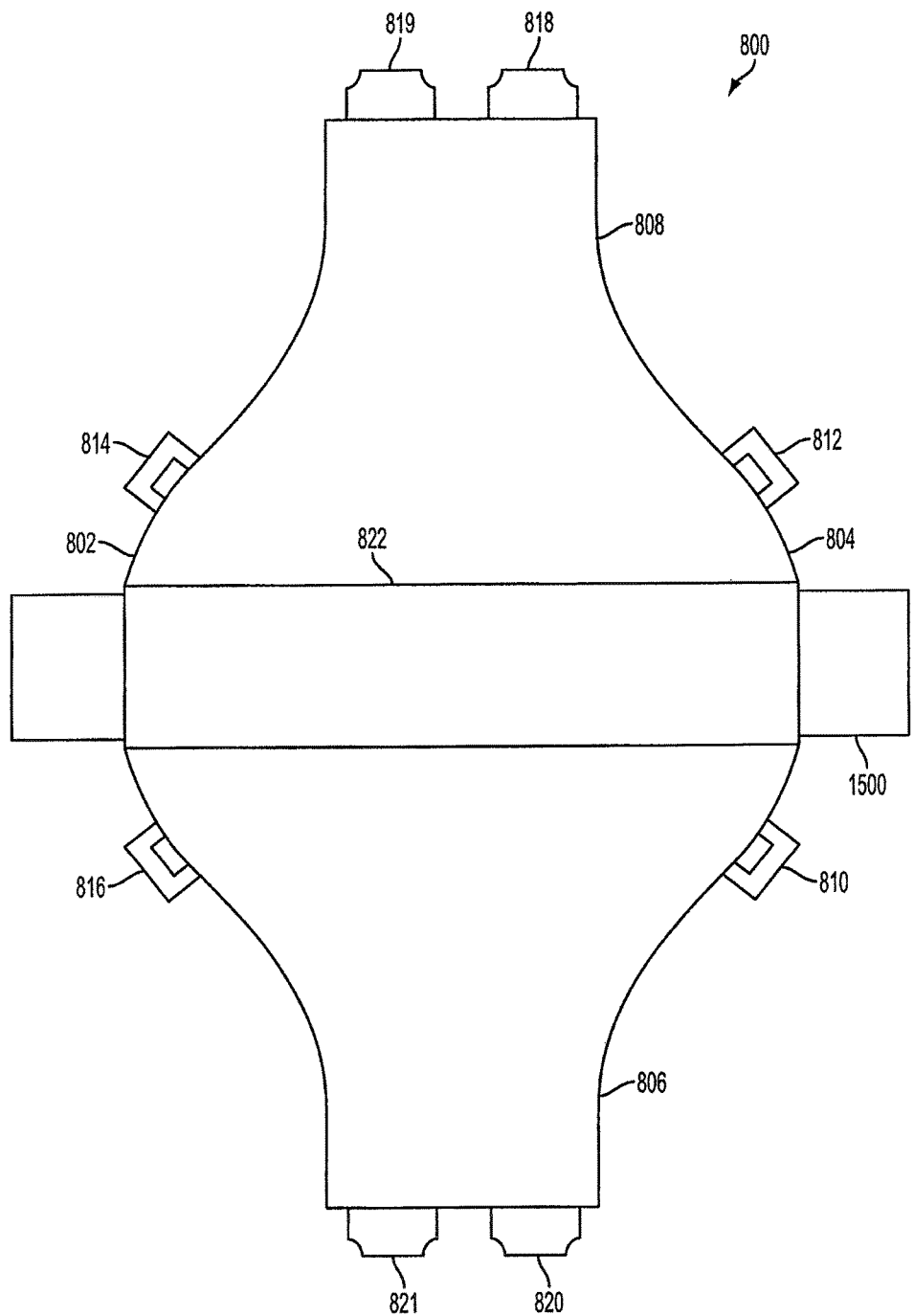
FIG. 8B is a view of a laid-open oval or pear-shaped skirt having a pouch that holds a balloon.

FIG. 8B is a view of a laid-open oval or pear-shaped skirt 800 having a pouch 822 that holds a balloon 1500. When the skirt 800 is wrapped around the stomach, the balloon 1500 can be secured in the pouch 822 or be inserted into the pouch 822 to keep the tucked-in portion within the stomach.

Figure 8C:
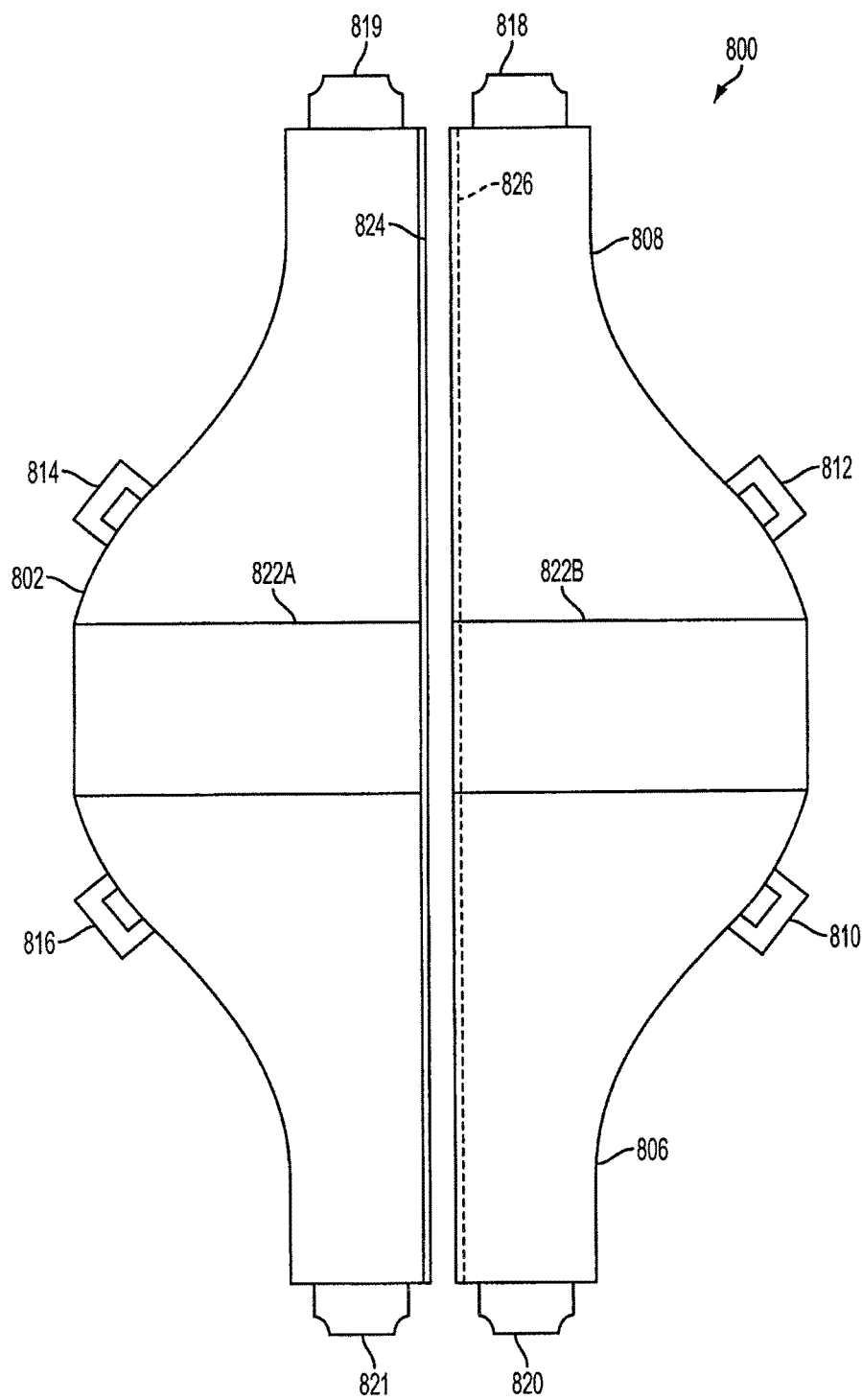
FIG. 8C is a view of a modular laid-open oval or pear-shaped skirt having a pouch that holds a balloon.

FIG. 8C is a view of a modular laid-open oval or pear-shaped skirt 800 having a pouch 822A and 822B that holds a balloon. The modular gastric skirt 800 may have two or more strips or modules. Each strip may have a ridge 824 and/or a groove 826 for attachment to adjacent strips. The ridge 824 securely fits into the groove 826 along the length of each strip to prevent unwanted detachment of adjacent strips and any in-growth of tissue between adjacent strips. The pouch 822 comprises two pieces 822A and 822B since the skirt 800 is modular.

FIG. 9A is a view of a folded gastric skirt 900 with locking clips. The gastric skirt 900 includes a proximal end 903 and a distal end 905. When the gastric skirt 900 is folded so that the proximal end 903 and the distal end 905 connect, a hollow shaped gastric skirt 900 is formed with a skirt body 902. Each locking clip comprises a male connector 904, 906, or 908, and a corresponding female receiver 914, 912, or 910, respectively. A right wing 916 and a left wing 918 are placed on opposite sides of one end of the skirt body 902. The wings 916 and 918 are used to connect the gastric skirt 900 to a collar (see also FIG. 11).

FIG. 9B is a view of a locking clip for the gastric skirt 900 shown in FIG. 9A. The locking clip 920 comprises the male connector 908, which includes a connector strap pin 922. The locking clip 920 also comprises the female connector 910. To engage the locking clip 920, the connector strap pin 922 interlocks with an opening in the female connector 910. Once the male connector 908 and the female connector 910 are engaged, the locking clip 920 holds a portion of the skirt body together. Furthermore, the male connector 908 includes a lower portion 926 which extends outwards. The female connector 910 includes an upper portion 924 which also extends outwards. When the male connector 908 and the female connector 910 are engaged, the lower portion 926 rests underneath the upper portion 924.

Figure 10A:
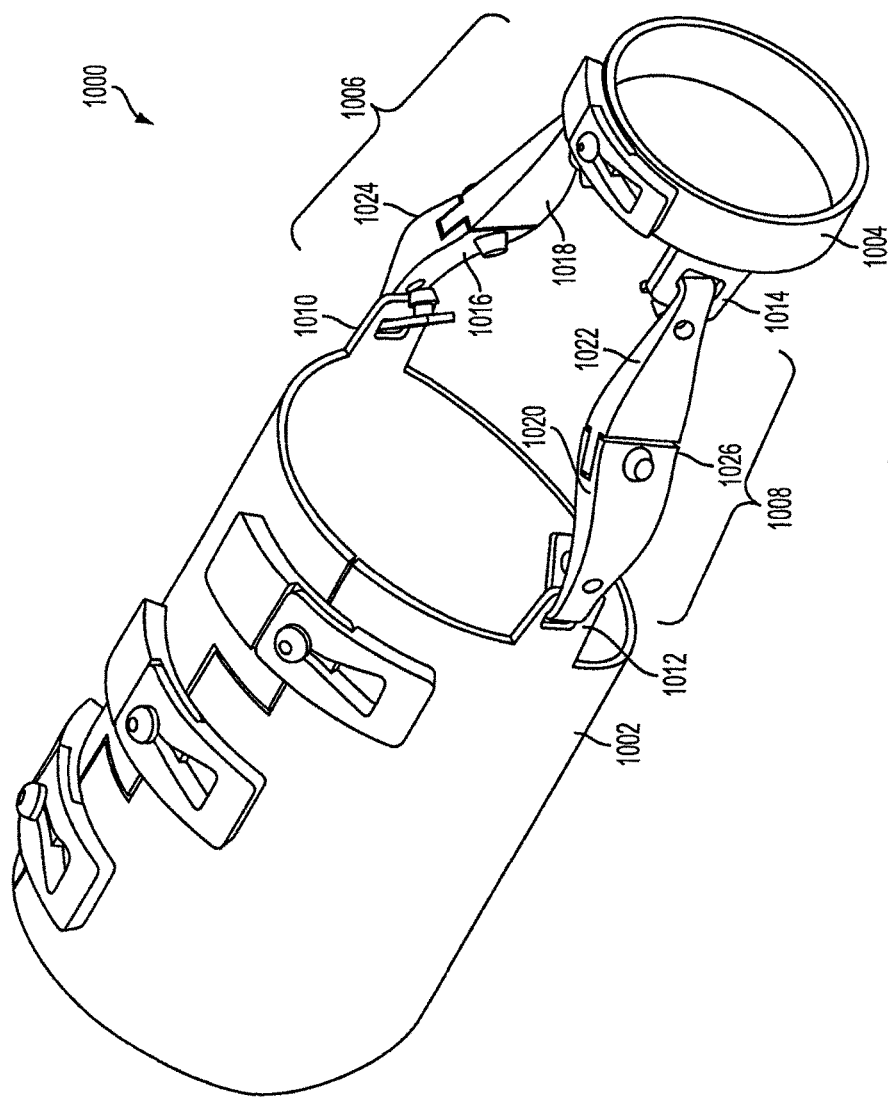
FIG. 10A is a view of a gastric skirt with a harness system.

FIG. 10A is a view of a gastric skirt 1002 with a harness system 1000. The harness system 1000 may include a gastric skirt 1002, an upper collar 1004, and connector straps 1006 and 1008. The gastric skirt 1002 is placed around the body of the stomach as previously described in FIG. 5A. In another embodiment, a lower collar (not pictured) is also included, allowing the upper collar 1004 and the lower collar to work in conjunction to hold the gastric skirt 1002 in position.

The upper collar 1004 is connected to the gastric skirt 1002 via the connector strap 1006 and the connector strap 1008, which are both, for example, connecting straps. The connector strap 1006 includes a skirt hook 1016 and a collar hook 1018. Likewise, the connector strap 1008 includes a skirt hook 1020 and a collar hook 1022. Regarding the connector strap 1008, the skirt hook 1020 connects to the gastric skirt 1002 at a wing 1012. The collar hook 1022 connects to the collar 1004 at a wing 1014. Regarding the connector strap 1006, the skirt hook 1016 connects to the gastric skirt 1002 at a wing 1010. The collar hook 1019 connects to the collar at a wing (not shown) located at a substantially parallel location as wing 1014 on the opposite side of collar 1004.

The connector strap 1006 has a flexible connector strap 1024 to accommodate angulations to various anatomical differences where the skirt hook 1016 and the collar hook 1018 connect with each other. Likewise, the connector strap 1008 has a flexible connector strap 1026 where the skirt hook 1020 and the collar hook 1022 connect with each other. The flexible connector straps 1024 and 1026 help to accommodate any angulations of the stomach in relation to the lower esophagus and the fundus or the stomach and the pylorus, as well as help to accommodate the angles and contractility or peristaltic movements of the stomach. In an embodiment, the connector straps 1024 and 1026 can bend from 1 degree to 90 degrees in any direction, and in a preferred embodiment, the connector straps 1024 and 1026 can bend from 10 degrees to 60 degrees in any direction to accommodate movements of the stomach.

Figure 10B:
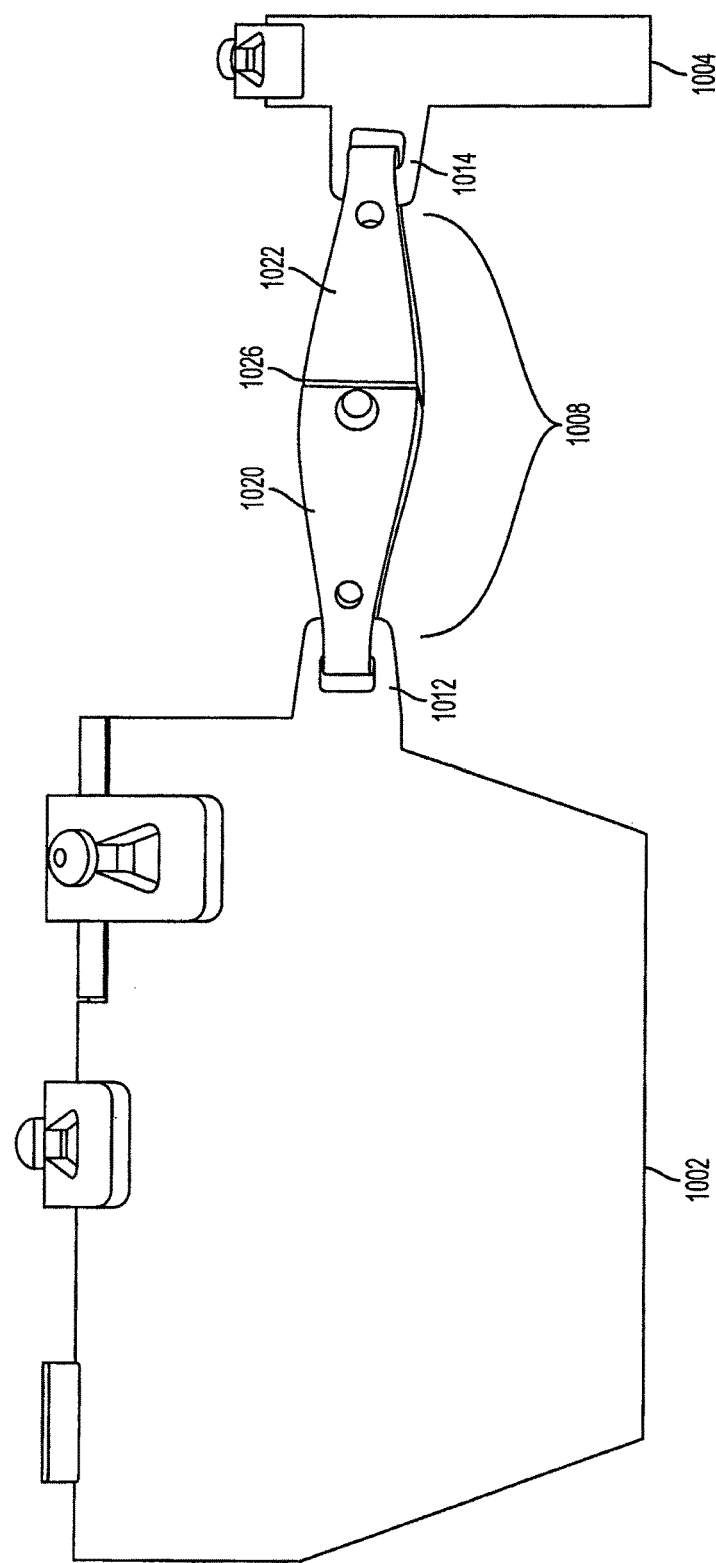
FIG. 10B is a side-view of a gastric skirt with a harness system.

FIG. 10B is a side-view of the gastric skirt 1002 with a harness system 1000. In an embodiment, the gastric skirt 1002, the upper collar 1004, the lower collar (not shown), the connector strap 1008, and the connector strap 1006, all have the same thickness and are all made of the same material. In an embodiment, this thickness is up to $1/35,000$th of an inch.

Figure 11:
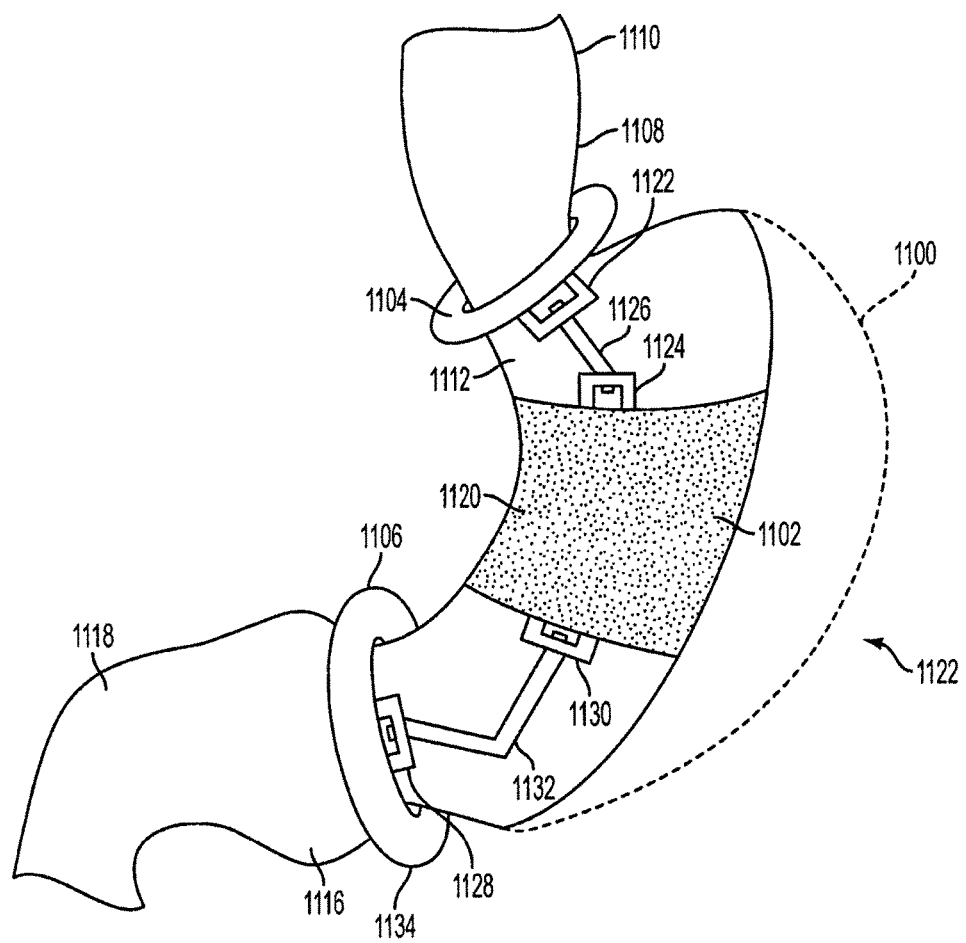
FIG. 11 is a view of a gastric wrap with a harness system in position around a stomach.

FIG. 11 is a view of a gastric skirt 1102 with a harness system in position around a stomach 1100. The gastric skirt 1102 is placed along the greater curvature 1122 and the lesser curvature 1120 of the stomach 1100. An upper collar 1104, also known as the cardia collar, is placed around the lower end of esophagus 1108 at a position near or adjacent to the cardia receiver 1112. The upper or cardia collar 1104 is large enough in diameter to encircle the lower esophagus 1108, but small enough so that it cannot encircle the larger diameter portion of the esophagus 1110. The upper collar 1104 is connected to the gastric skirt 1102 via a connector strap 1126. The connector strap 1126 is attached to the upper or cardia collar 1104 at a wing 1122, and the connector strap 1126 is attached to the gastric skirt 1102 at a wing 1124. This design prevents the upper collar 1104 from moving very high up the esophagus 1110, helps to hold the gastric skirt 1102 in place, and may help in reducing gastro esophageal reflux ("gastric reflux") or achalasia or dysphagia after the procedure.

The lower collar 1106, also known as the antral collar, is placed around a lower portion of the stomach near the angular receiver 1134 at the pylorus 1116, also known as the pyloric antrum receiver. The lower collar 1106 is large enough in diameter to encircle part of the lower portion of the stomach near the pylorus 1116, but small enough so that it cannot encircle the larger diameter portion of the small intestine 1118. The lower collar 1106 is connected to the gastric skirt 1102 via connector strap 1132. The connector strap 1132 is attached to the lower collar 1106 at a wing 1128, and connector strap 1132 is attached to the gastric skirt 1102 at a wing 1130. This design prevents the lower collar 1106 from moving down into the small intestine 1118, and helps to hold the gastric skirt 1102 in place. Furthermore, the lower collar 1106 may assist in slowing the gastric emptying from the stomach into the small intestine 1118. The lower collar 1106 may also assist in anchoring the gastric skirt 1102 in place.

In another embodiment, only the upper collar 1104 is attached to the gastric skirt 1102, and a lower collar 1106 is not present. As the volume of the fundus 1114 fills with food, the fundus 1114 stretches and expands, preventing the gastric skirt 1102 from sliding upwards. Thus, the lower collar 1106 may not necessarily be required in all patients to help hold the gastric skirt 1102 in place around the stomach 1100. Alternatively, in another embodiment, only the lower collar 1106 is attached to the gastric skirt 1102 and an upper collar 1104 is not present.

The gastric skirt 1102 and harness system are modular, and provides patients with at least three different options. In the first option, only the gastric skirt 1102 is utilized, without the collars 1104 and 1106 and the connector straps 1126 and 1132. In this embodiment, the healthcare professional may decide to not include the collars 1104 and 1106 if there is not a high risk of gastric reflux or achalasia, or if there is not a high risk that the gastric skirt 1102 may be displaced.

In the second option, the gastric skirt 1102 is utilized along with the collar 1104, but without the collar 1106 and without the connector straps 1126 and 1132. In this embodiment, the gastric skirt 1102 and the collar 1104 are not connected to each other. The healthcare professional may decide on this option if there is a risk of gastric reflux, achalasia, dysphagia but not a high risk that the gastric skirt 1002 or the collar 1104 may be displaced.

In the third option, the gastric skirt 1102 is utilized with the collars 1104 and 1106 and the connector straps 1126 and 1132. The healthcare professional may decide on this option if there is a risk of gastric reflux, or dysphagia and a risk of that the gastric skirt 1102 or collars 1104 and 1106 may be displaced. In this option, both the upper collar 1104 and the lower collar 1106 do not need be utilized, and only one of the collars 1104 or 1106 can be used. The upper collar 1104 not only serves to hold the gastric skirt 1102 in place, but is also a mechanism to help reduce gastric reflux and dysphagia.

The modular design allows the healthcare professional to decide which components of the gastric skirt system will be utilized, as well as the order of insertion of the various components.

In an embodiment, the upper collar 1104 and the lower collar 1106 each have a diameter from about 4 centimeters to about 6 centimeters. The upper collar 1104 can have a larger diameter up to about 11 centimeters in cases where the patient suffers from esophageal achalasia. In an embodiment, the length of the upper collar 1104 and the lower collar 1106 is up to about 4 centimeters.

The length of connector straps 1126 and 1132 can be varied to accommodate various stomach sizes. In a preferred embodiment, connector strap 1126 and connector strap 1132 have a length of about 5 centimeters.

The gastric skirt 1102 can have a length of about 6 centimeters to about 14 centimeters. In a preferred embodiment, the length of the gastric skirt 1102 is from about 8 centimeters to about 12 centimeters. The width of the greater curvature side of the gastric skirt 1102 is from about 7 centimeters to about 10 centimeters, and the width of the lesser curvature side of the gastric skirt 1102 is from about 3 centimeters to about 5 centimeters.

Some patients who undergo various gastric banding procedures experience gastric reflux, and it is believed that gastric banding procedures may cause or aggravate gastric reflux. Gastric reflux occurs when irritating stomach contents, such as acid, accumulate in the stomach outside of the lower esophagus entrance, and eventually, leak or regurgitate back into the esophagus. This leakage, over time, causes the lower esophagus to lose its tone, leaving the lower esophagus entrance poorly controlled, tortuous, unconstructed or floppy.

The upper collar 1104 may be approximately the same size as the lower esophagus or may be slightly larger. Once in position, the upper collar 1104 applies support by forming a significant wrap around the lower end of the esophagus 1108 or the cardia. The upper collar 1104 restricts the lower end of the esophagus opening 1108 and attempts to minimize regurgitation, thereby reducing gastric reflux.

Figure 12:
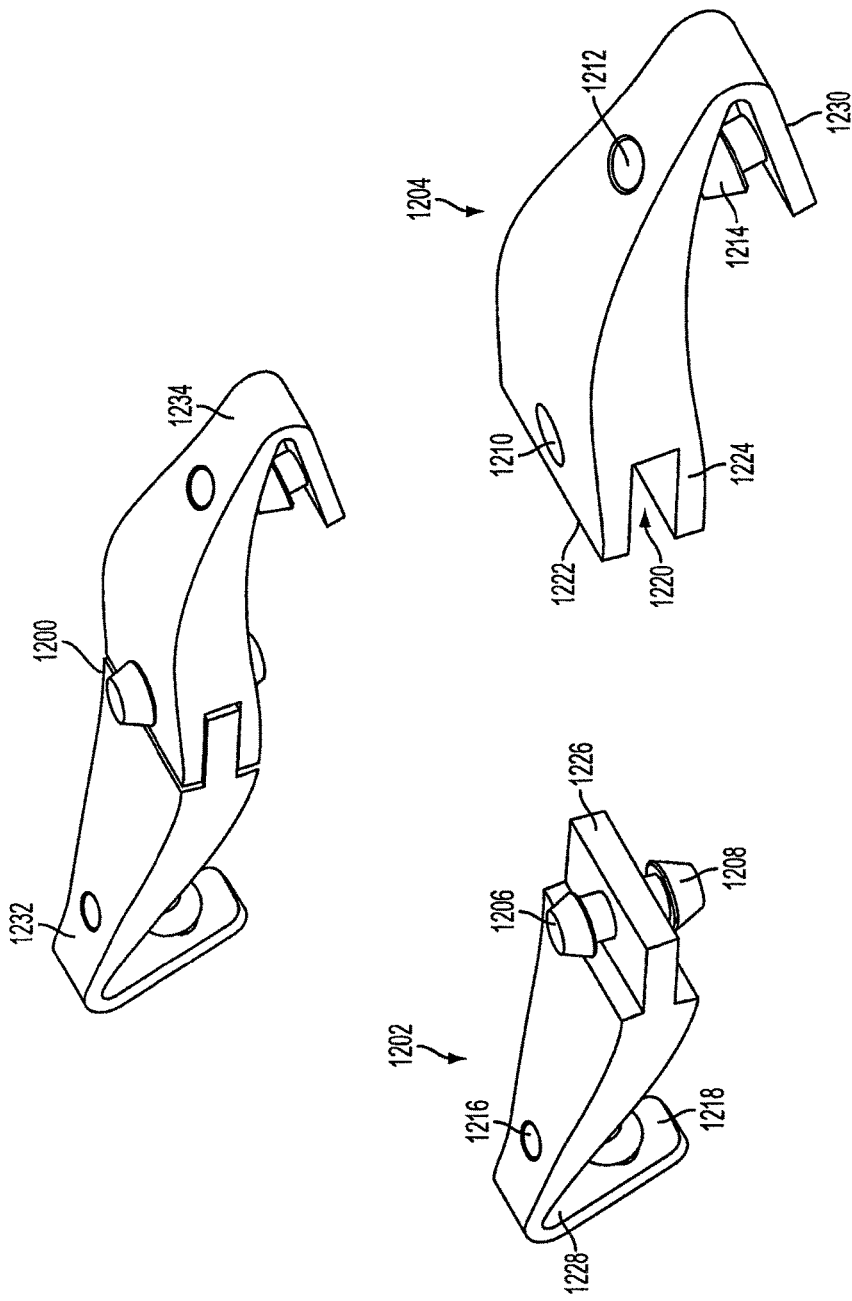
FIG. 12 is a view of an exemplary connector.

FIG. 12 is a view of an exemplary connector strap. The connector strap 1200 has a lower portion 1232 and an upper portion 1234. The lower portion 1232 corresponds to the skirt hook 1202. The upper portion 1234 corresponds to the collar hook 1204. The connector strap 1200 has a skirt hook 1202 and a collar hook 1204. The skirt hook 1202 includes connector strap pin 1206, connector strap pin 1208, and extending portion 1226. The collar hook 1204 includes a hole 1210 through ridge 1222 and a second hole (not shown) through ridge 1224. The collar hook 1204 also includes a cavity 1220. The connector strap pins 1206 and 1208 are smaller in diameter than the diameters of hole 1210 and the second hole through ridge 1224. This design allows increased flexibility as the connector strap pins 1206 and 1208 have space to re-position with their respective holes when the connector strap 1200 is rotated or shifted.

To connect the skirt hook 1202 and the collar hook 1204 together, connector strap pin 1206 is inserted into hole 1210, and connector strap pin 1208 is inserted into the second hole through ridge 1224. The extending portion 1226 is inserted into the cavity 1220. Once the skirt hook 1202 and the collar hook 1204 are connected, the connector strap 1200 is formed.

The skirt hook 1202 also includes hole 1216 and connector strap pin 1218. To attach the connector strap 1200 to a wing (not shown) on the gastric skirt (not shown), the wing is placed inside the connector strap cavity 1228 so that connector strap pin 1218 is inserted through the wing. To secure the wing to the skirt hook 1202, the connector strap pin 1218 is pushed through the hole 1216. The connector strap pin 1218 has a triangular shape, with a narrow top and a wide base. The diameter of the base of the connector strap pin 1218 is larger than the diameter of hole 1216. This design allows the connector strap pin 1218 to be securely fastened once it is inserted through hole 1216. Likewise, the collar hook 1204 includes a hole 1212, a connector strap pin 1214, and a connector strap cavity 1230 to secure the collar hook 1204 to a wing on the collar (not shown).

In an embodiment, the connector strap 1200 is made of an elastomer, such as silicone. However, the connector can be made from other types of elastomers or thermoplastic polymers, ePTFE, Dacron®, or any combination thereof.

Figure 13A:
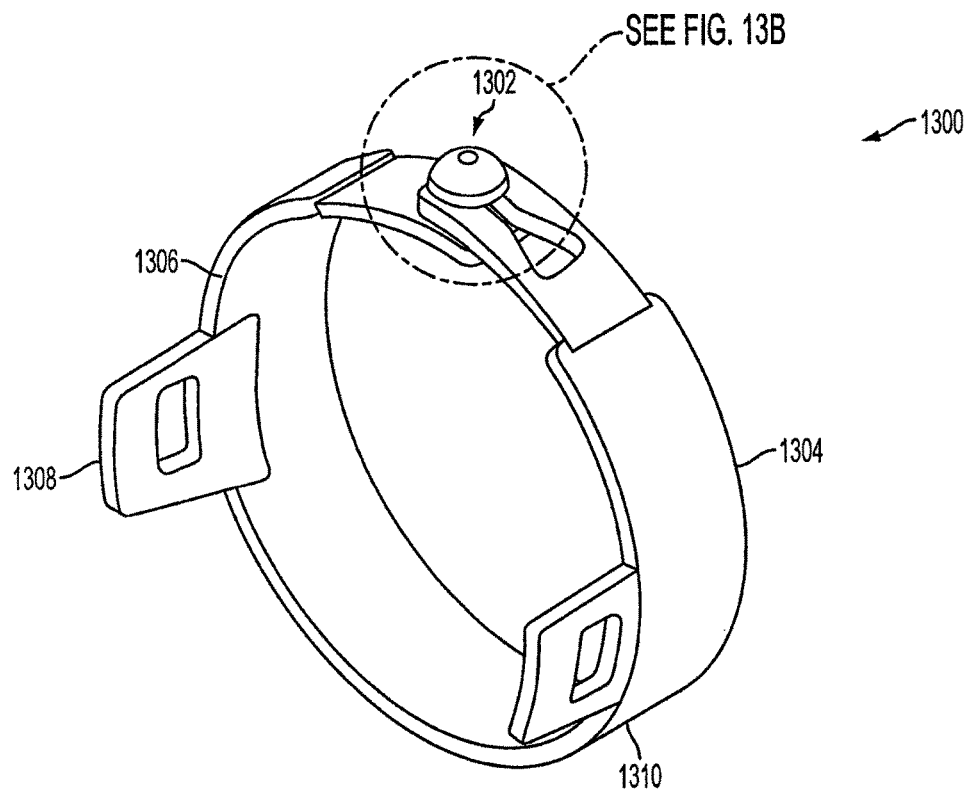
FIG. 13A is a view of a collar with wings.

FIG. 13A is a view of a collar. The collar 1300 includes a locking clip 1302. The collar 1300 has a distal end 1304 and a proximal end 1306. The distal end 1304 and the proximal end 1306 are connected by the locking clip 1302. The collar 1300 further includes a first wing 1308 and a second wing 1310 that are used to secure the collar 1300 to the gastric skirt connector strap (not shown).

In order to place the collar 1300 around the lower esophagus or cardia, the locking clip 1302 is not engaged, so that the distal end 1304 and the proximal end 1306 are laid open. The collar 1300 is then fitted around a portion of the lower esophagus as described above. Once the collar 1300 is in place, the locking clip 1302 is engaged by connecting the distal end 1304 and the proximal end 1306 together.

Figure 13B:
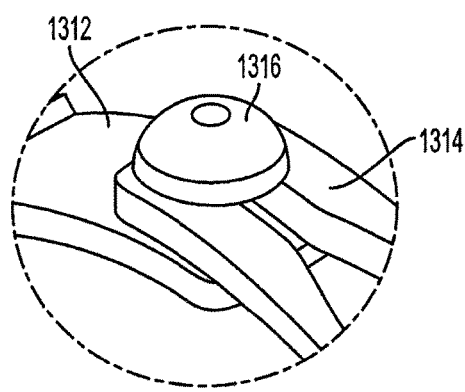
FIG. 13B is a view of a locking clip for a collar.

FIG. 13B is a view of a locking clip for a collar 1300. The male connector 1312 includes a connector strap pin 1316 which interlocks with an opening in the female connector 1314. Once the male connector 1312 and the female connector 1314 are engaged, the locking clip holds the collar in position.

Figure 13D:
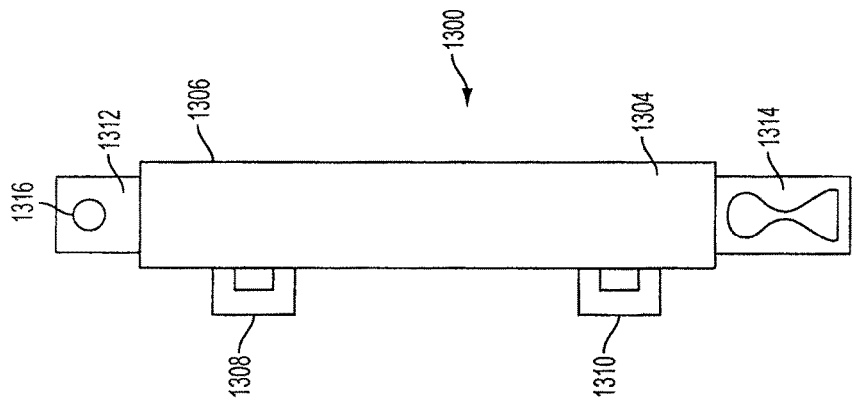
FIG. 13D is a view of a laid-open collar.
Figure 13C:
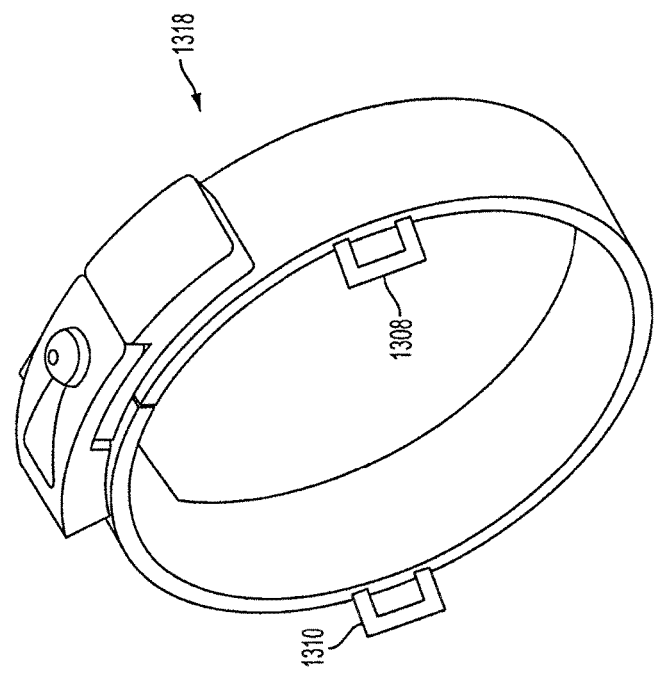
FIG. 13C is a view of a collar without wings.

FIG. 13C is a view of a collar 1300 without wings. The collar 1318 is used when a collar is not required to be connected to the gastric skirt (not shown), such as in surgical option one discussed above.

The locking clip 1302 can be any type of locking, coupling, or clasping mechanism, and is not limited to the male connector 1312 and female connector 1314 designs shown in FIGS. 13A-D. For example, the male connector may be an insertable clip, and the female connector can include an opening to receive and secure the insertable clip. In another embodiment, the clip can slide in and out of the body of the skirt, and can have an elastic component that stretches to accommodate the size and shape of the stomach.

In an embodiment, the collar 1300 and locking clip 1302 are made from a composition of silicone and PTFE/ePTFE. However, the collar 1300 and locking clip 1302 can be made from other elastomers or thermoplastic polymers, or any combination thereof.

In another embodiment, the distal end 1304 and proximal end 1306 can be sutured or stapled together at the time of positioning by the healthcare professional.

In yet another embodiment, the collar 1300 can be shaped as a semicircular ring, or in a "C" shape, and be made of a memory-retaining material. Once the collar 1300 is placed around a portion of the lower esophagus, it retains its shape. Thus, a locking clip is not required.

FIG. 13D is a view of a laid-open collar 1300. The collar 1300 is in a strap form when the male connector 1312 and the female connector 1314 are not connected.

As described above and shown in FIG. 1B, a portion of the stomach is tucked inwards prior to application of the gastric skirt around the stomach.

Figure 14:
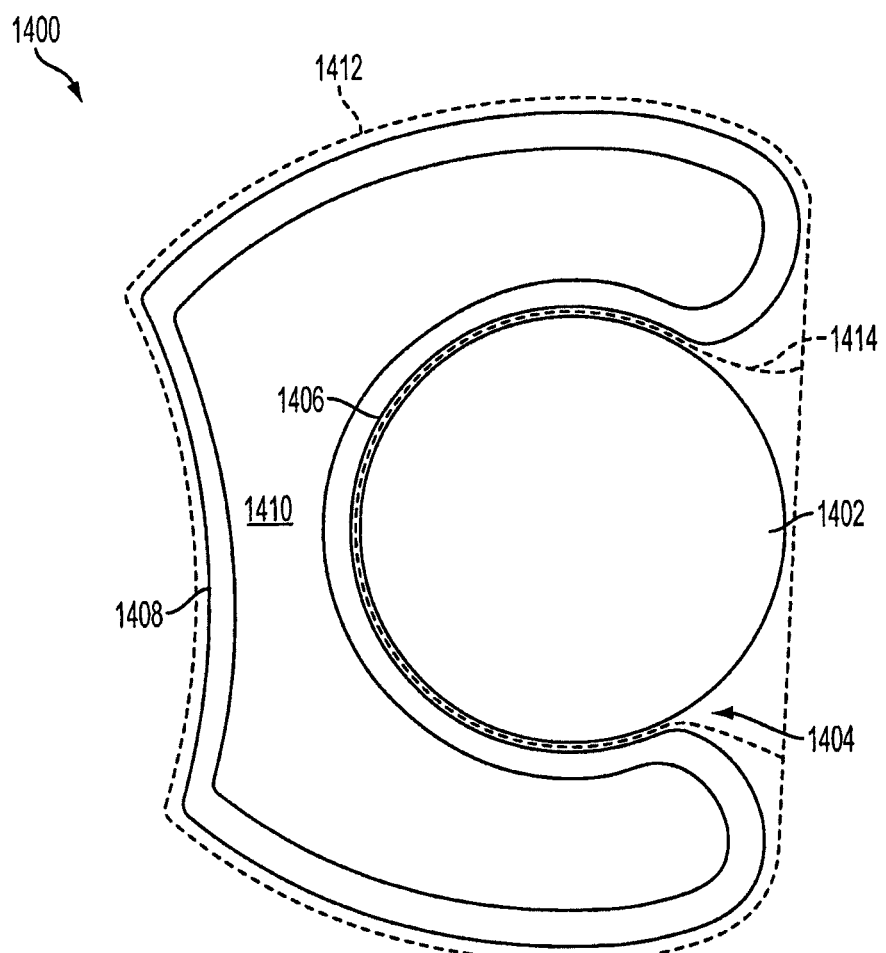
FIG. 14 is a cross-sectional view of a stomach and a balloon positioned within a greater curvature of the stomach when the greater curvature is tucked into the stomach.

FIG. 14 is a cross-sectional view of a stomach 1400 and a balloon 1402 positioned within a greater curvature 1406 of the stomach 1400 when the greater curvature 1406 is tucked into the stomach 1400. In an embodiment, after the greater curvature 1406 of the stomach 1400 is tucked inwards, a cavity 1404 is formed as a result of the tucking procedure and a balloon 1402 is placed within the cavity 1404, which can be left open, and a gastric skirt 1412 is tightly positioned around the stomach 1400 to hold the balloon 1402 in place within the cavity 1404. Hence, the balloon 1402 is placed within the tucked-in portion of the stomach 1400. Alternatively, the balloon 1402 may be placed within a pouch 1414 that is attached to the gastric skirt 1412. The greater curvature 1406 of the stomach 1400 is pushed inwards to reduce the inner volume 1410 of the stomach 1400. The balloon 1402 applies pressure against the greater curvature 1406 of the stomach 1400 and helps to maintain the shape of the cavity 1404. Following the placement of the balloon 1402, the gastric skirt 1412 is placed around the stomach 1400 as described above. In this embodiment, when the gastric skirt 1412 is positioned around the stomach 1400, the connectors as shown in FIG. 5B connect with one another along the lesser curvature 1408 of the stomach 1400.

As described above, the greater curvature 1406 of the stomach 1400 is the preferred tucking portion. However, the tucked-in portion of the stomach 1400 may be a portion of the lesser curvature 1408, or any portion of the stomach 1400 not along either the greater curvature 1406 or the lesser curvature 1408. If the tucked-in portion of the stomach 1400 is along the lesser curvature 1408, then the connectors as shown in FIG. 5B connect with one another along the greater curvature 1406 of the stomach 1400.

Figure 15A:
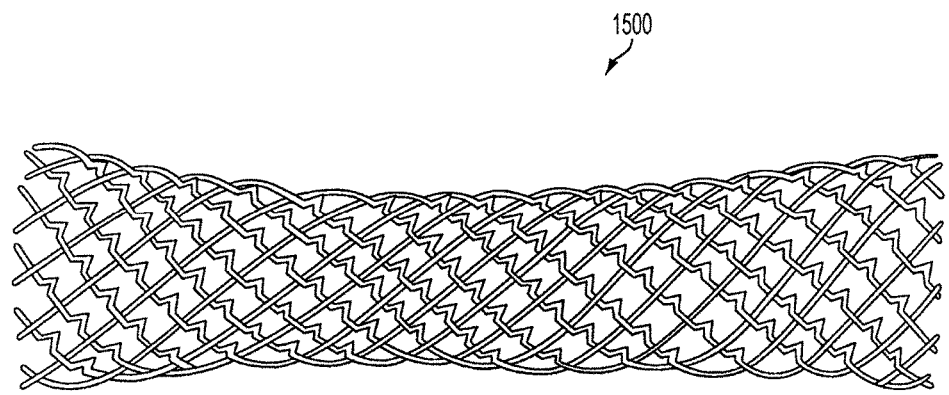
FIG. 15A is a view of the balloon of FIG. 14.

FIG. 15A is a view of the balloon of FIG. 14. The balloon 1500 can be a sealed or open ended stent, cylindrical air filled or saline filled device with an ePTFE, Dacron®, or silicon coating or covering. The balloon 1500 is preferably made of an alloy of nickel and titanium (Nitinol) or stainless steel wire cage which provides the balloon 1500 with a self-expanding memory. The unique characteristic of this alloy, known generally as "Nitinol," is that it has a thermally triggered shape memory. This allows the balloon cage to be crimped per a desired length, width, and volume based on the balloon size required per patient's stomach dimensions, and then the balloon 1500 is crimped into a sheath so that it can fit through a trocar (not shown). The balloon 1500 regains its desired shape when deployed at room temperature, such as the temperature of the human body or outer stomach lining.

The semi-rigid or rigid Nitinol or stainless steel wire frame is covered with ePTFE, silicone, Dacron® or any other elastomer or thermoplastic elastomer, nitinol cage. The balloon 1500 provides support to the outer lining of the stomach when the balloon 1500 is placed in position within the cavity 1404 of FIG. 14. The desired shape of the balloon 1500 is retained even under pressure from the stomach lining or the gastric skirt (not shown) since Nitinol or stainless steel or titanium wire cage is rigid and has memory. After the balloon 1500 is placed in position, the gastric skirt is placed around the stomach as described above.

In one embodiment, the self-expanding nitinol cage or stainless steel wire cage balloon 1500 is covered with silicone, and is formed in the shape of a cylindrical balloon, and can have open or closed ends. In another embodiment, the self-expanding nitinol balloon 1500 is covered with ePTFE, and can have open or closed ends.

Figure 15B:
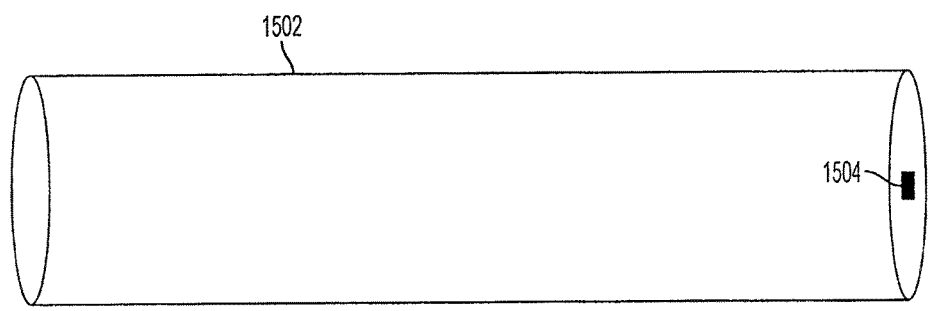
FIG. 15B is a view of a sealed balloon with a port.

FIG. 15B is a view of a balloon 1502 with a port 1504. The balloon 1502 is made entirely of silicone, other elastomers, thermoplastic polymers, or any combination thereof, and may be filled with air or liquid (e.g., saline) and methylene blue and has a closed end and a port 1504 to inject air, liquid or methylene blue. The methylene blue is used to detect leaks of the balloon 1502.

The balloon 1500 has a length of about 7 centimeters to about 10 centimeters. In an embodiment, the diameter of the balloon 1500 is from about 1 centimeter to about 3 centimeters. However, the diameter of the balloon 1500 can be adjusted by the healthcare professional based on the amount of stomach that is tucked-in.

Figure 16:
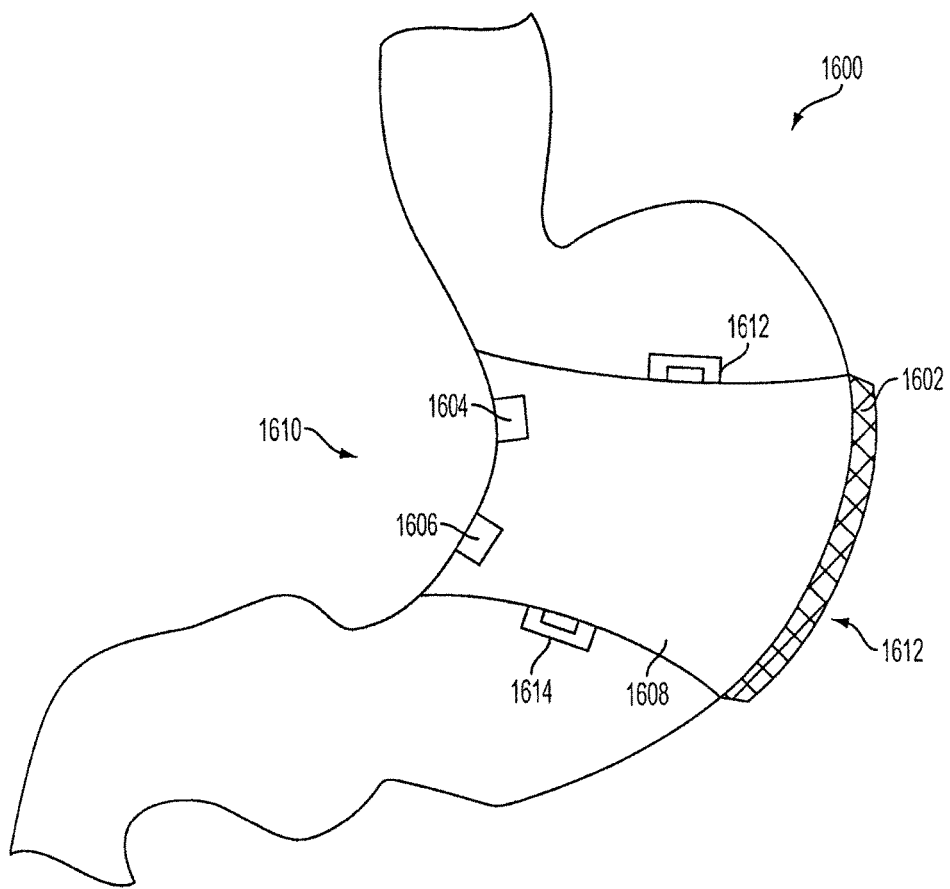
FIG. 16 is a view of the gastric wrap of FIG. 6 and the balloon in position around a stomach.

FIG. 16 is a view of the gastric skirt of FIG. 6 and the balloon in position around a stomach. As seen in FIG. 16, connectors 1604 and 1606 are positioned on the lesser curvature side 1610 of the stomach 1600. Balloon 1602 is positioned on the greater curvature side 1612 of the stomach 1600. In this embodiment, the connectors 1604 and 1606 are not on the greater curvature side 1612 so that there is room for the balloon 1602 to be retained and held in place by the gastric skirt 1608 within the tucked-in portion (not shown) of the stomach.

Furthermore, optional wings 1612 and 1614 are attached to the gastric skirt 1608 to attach the gastric skirt 1608 to collar connector straps (not shown).

Figure 17:
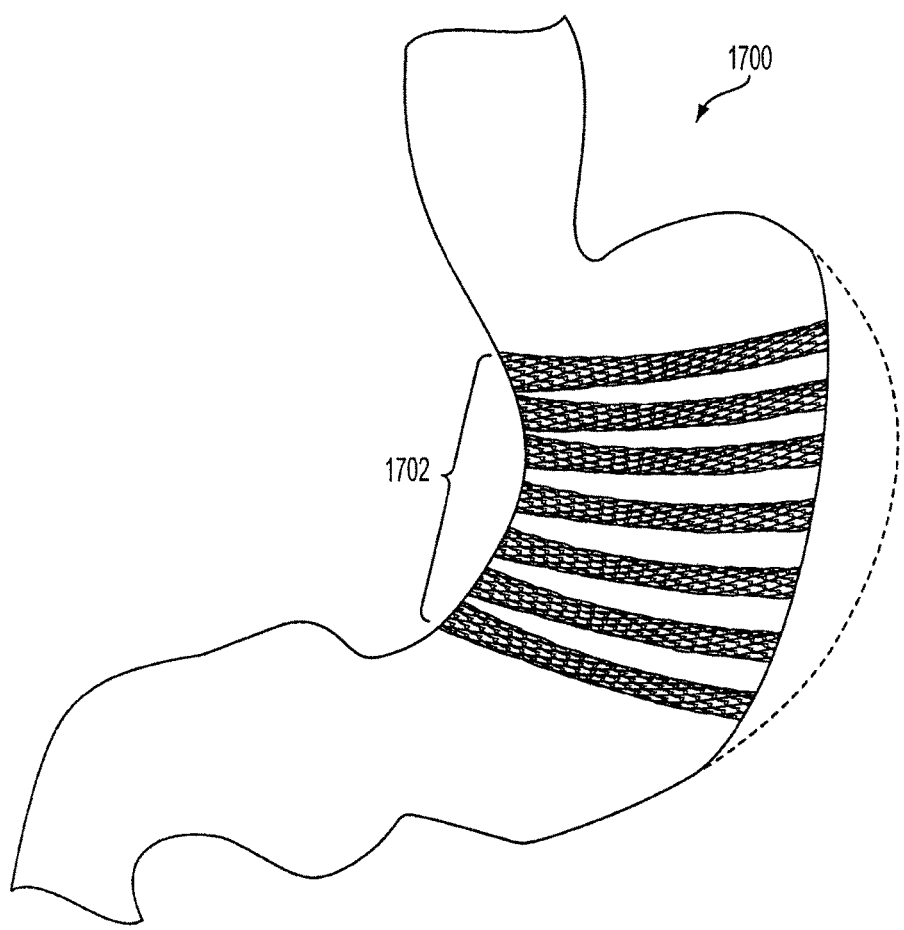
FIG. 17 is a view of one or more ropes wrapped around a tucked-in stomach.

FIG. 17 is a view of one or more ropes 1702 wrapped around a tucked-in stomach 1700. The ropes 1702 may be made of a biodegradable material or a woven silicon material or any other material described herein. The stomach 1700 is tucked-in and then the ropes 1702 are wrapped around the stomach 1700. Each rope 1702 can be a silicone rope, a mesh made of biodegradable elastomer, a metal, an alloy, a silicone or thermo-elastic material to harness the stomach or to create the pouch proximally or distal to the body of the stomach or to produce the same effect as the gastric skirt by tucking the stomach.

Figure 18:
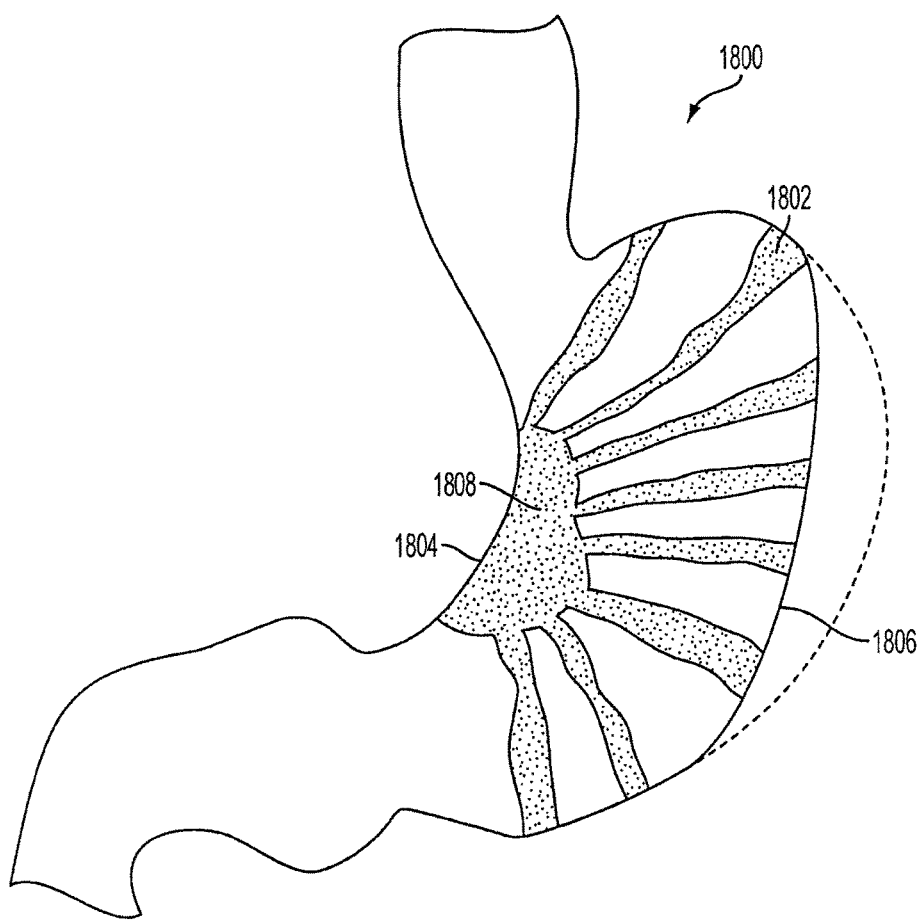
FIG. 18 is a view of one or more tentacles wrapped around a tucked-in stomach where the tentacles can be independently pulled and locked in place using a ring and clip system or a tie lock.

FIG. 18 is a view of one or more tentacles 1802 wrapped around a tucked-in stomach 1800 where the tentacles 1802 can be independently pulled and locked in place using a ring and clip system 1808 or a tie lock (not shown). Each tentacle 1802 can be independently tighten and loosened to control the tension. Each tentacle 1802 can be pulled through a ring or hole and the clip can lock the tentacle in place. The tentacles 1802 can be wrapped around the greater curvature 1806 and the lesser curvature 1804 of the stomach 1800. The tentacles 1802 can be any shape, such as straight or curved, and are not limited to the design shown in FIG. 18. Furthermore, the tentacles 1802 can be made of an expandable material originating from the body at the lesser curvature 1804 or the greater curvature 1806.

Figure 19:
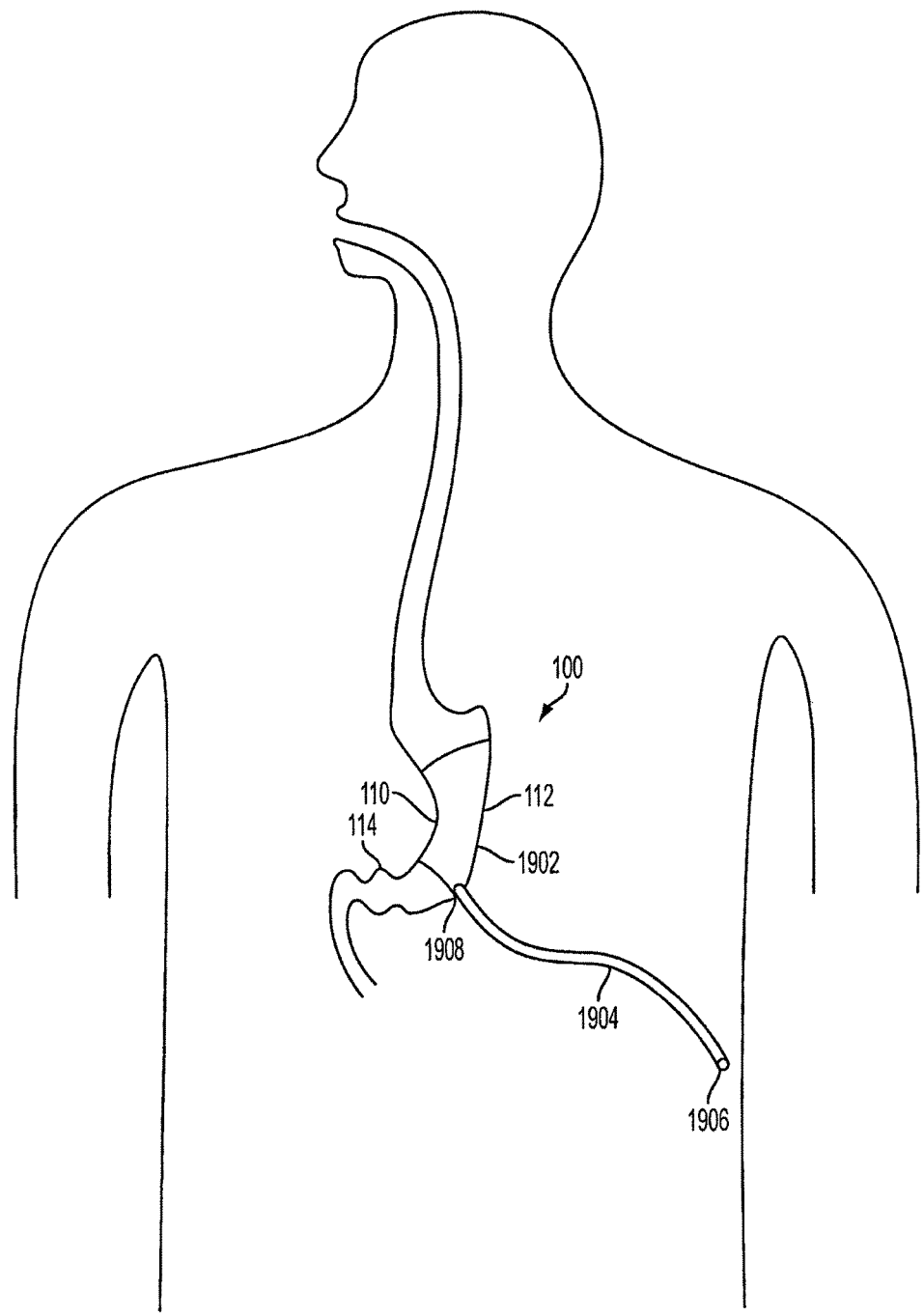
FIG. 19 is a view of an inflatable gastric skirt positioned around a stomach.

FIG. 19 is a view of an inflatable gastric skirt 1902 positioned around a stomach. In an embodiment, the gastric skirt 1902 is positioned around the stomach along the lesser curvature 110 and the greater curvature 112, similar to the gastric skirt 200 described above. The gastric skirt 1902 includes one or more finable or inflatable chambers that are attached to an interior surface of the gastric skirt 1902.

In an embodiment, the gastric skirt 1902 is inflated via a tube 1904 that is connected to the one or more inflatable chambers. The tube 1904 includes an inlet 1906 that can be located slightly beneath the skin of the patient. The tube 1904 also includes an outlet 1908 which is connected to the one or more inflatable chambers 2008 (see also FIG. 20). In an embodiment, the inlet 1906 can be sutured or stapled beneath the skin so that it is accessible via an incision.

In another embodiment, the inlet 1906 can include an RFID tag with an antenna to assist a healthcare professional in locating the inlet 1906 for subsequent adjustments. An external RFID locator or reader, such as in a handheld device, can be used to locate the inlet 1906 so that a syringe can be inserted directly into an access cavity of the inlet 1906.

Figure 20:
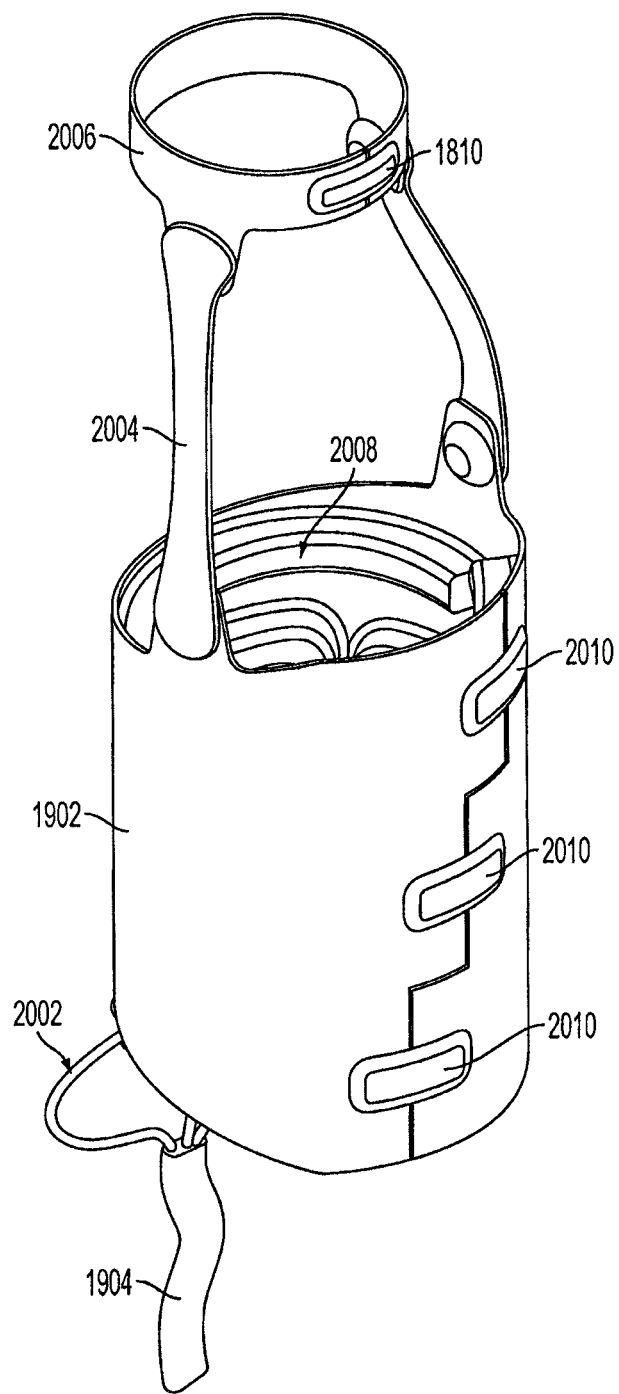
FIG. 20 is a view of an inflatable gastric skirt and a triple-lumen tube.

FIG. 20 is a view of an inflatable gastric skirt and a triple-lumen tube 1904. In an embodiment, the tube 1904 includes three separate lumens 2002, with each lumen connected to a separate inflatable chamber 2008. In another embodiment, the tube 1904 can include a single lumen or a double lumen. In yet another embodiment, the tube 1904 can include four or more lumens, with each lumen connected to a separate inflatable chamber that can be filled with a fluid.

In an embodiment, the gastric skirt 1902 can be positioned around the stomach and secured into place via clips 2010. In an embodiment, the gastric skirt 1902 is configured to cover at least 14 square centimeters of the outer surface of the stomach 100. Thus, the gastric skirt 1902 has a surface area of at least 14 square centimeters. Once in place, the gastric skirt 1902 can be further tightened around the stomach by inflating, filling, or expanding the chambers 2008. Upon inflation of the inflatable chambers 2008, the gastric skirt 1902 applies constriction pressure around or to the stomach. The level of inflation can be determined based on a desired stomach constriction level.

In an embodiment, the gastric skirt 1902 includes an inflatable collar 2006 configured to surround the lower esophageal/cardia portion of the stomach. The inflatable collar 2006 is coupled to the gastric skirt 1902 via two or more connector straps 2004. The inflatable collar 2006 provides a harness and adds stability to the gastric skirt 1902 after the gastric skirt 1902 has been positioned around the stomach.

Figure 48A:
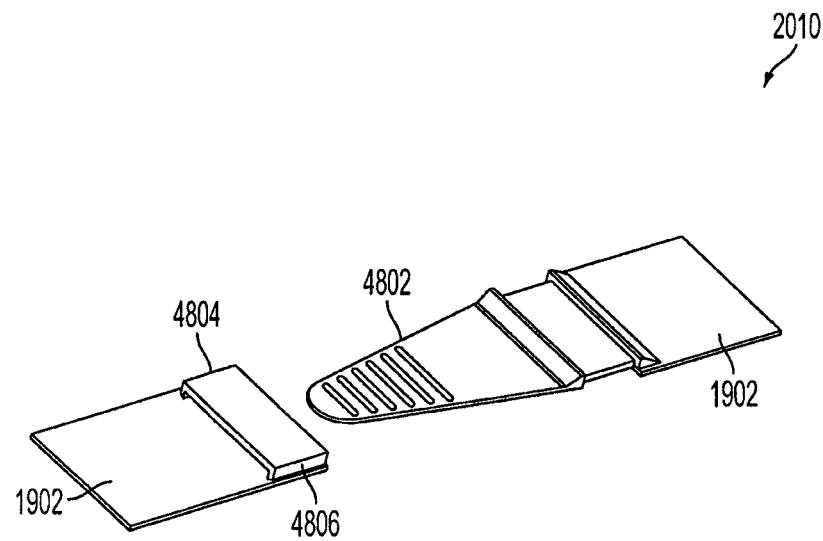
FIG. 48A is a view of unconnected clip members.
Figure 48B:
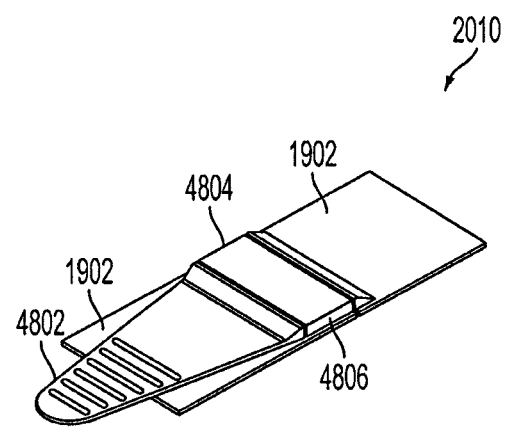
FIG. 48B is a view of connected clip members.

Referring to FIGS. 48A-B, the clips 2010 can each include a male tooth 4802 and a female receiver 4804 configured to engage the male tooth 4802. Upon insertion of the male tooth 4802 into the female receiver 4804, the male tooth 4802 releasbly locks with the female receiver 4804 as shown in FIG. 48B. The clips 2010 may include a release tab 4806 which releases the male tooth 4802 from the female receiver 4804 upon the application of pressure to the release tab 4806. Further, the locking mechanism can have a "pop-fit" design that provides a tactile indication that the gastric skirt 1902 is secured in place. The locking mechanism of the gastric skirt 1902 is not limited to the clips 2010 shown in FIGS. 48A-B, but can be any type of connecting mechanism which can securely connect the two opposite ends of the gastric skirt 1902 around the stomach.

In another embodiment, the gastric skirt 1902 does not have connectors, but the ends of the gastric skirt 1902 are attached to one another by staples, sutures, or heat fusion after the gastric skirt 1902 is positioned around the stomach 100.

Figure 21:
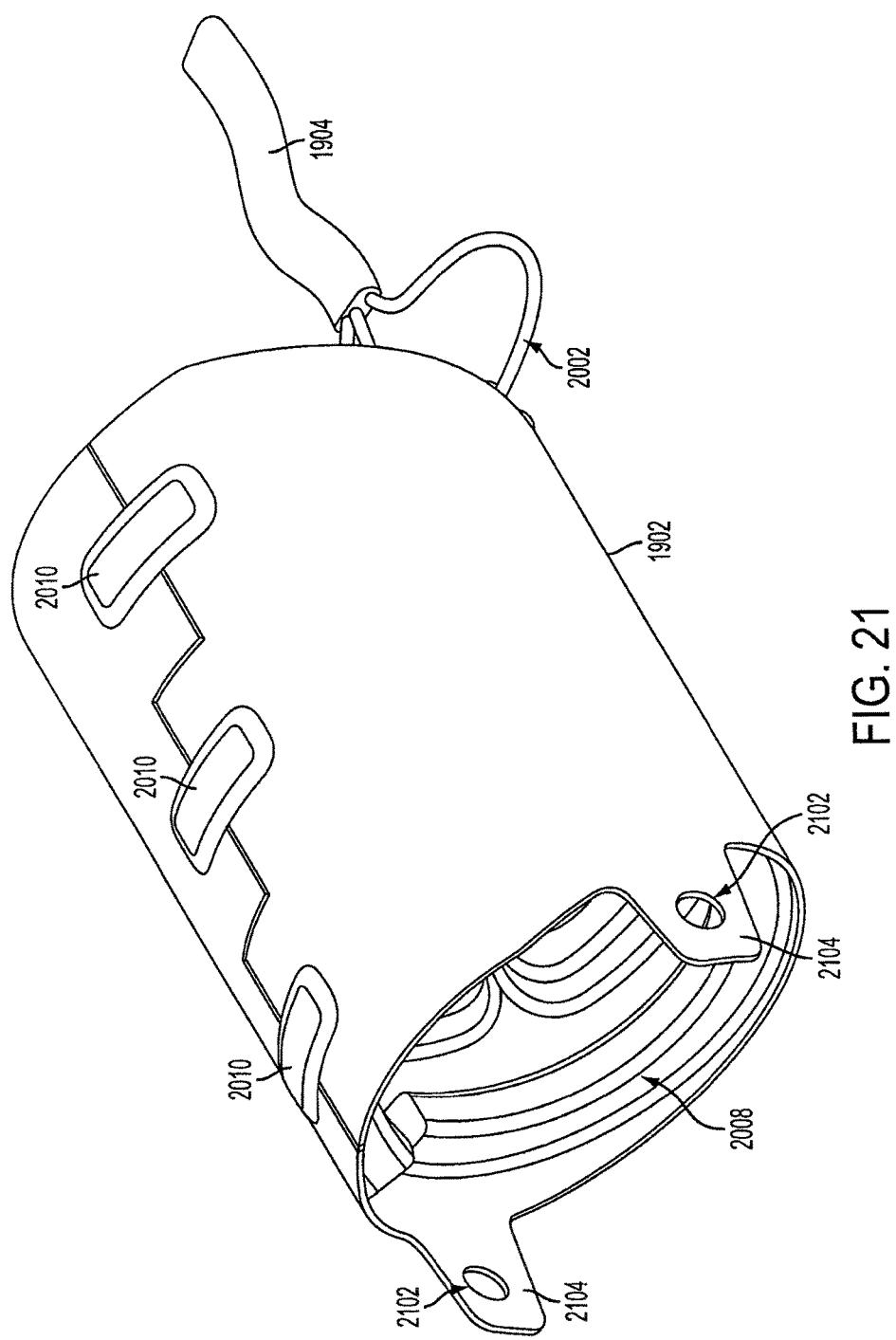
FIG. 21 is a view of an inflatable gastric skirt without a harness system.

FIG. 21 is a view of an inflatable gastric skirt without a harness system. The gastric skirt 1902 includes connector holes 2102 where the connector straps 2004 (not shown) are attached. The connector holes 2102 and corresponding tabs 2104 are optional depending on whether the harness system is being used. In an embodiment, the gastric skirt 1902 is a standalone device without the harness system, and can be positioned around the stomach without the collar 2006 and the connector straps 2004.

Figure 22B:
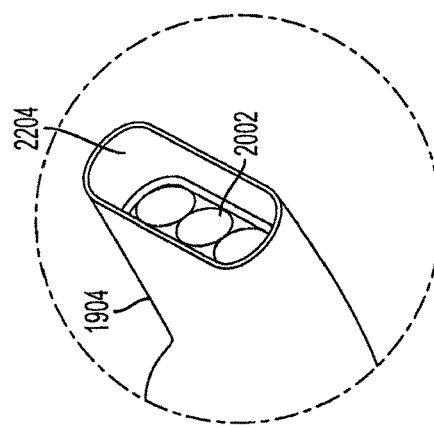
FIG. 22B is a view of a cavity of a triple-lumen tube.
Figure 22A:
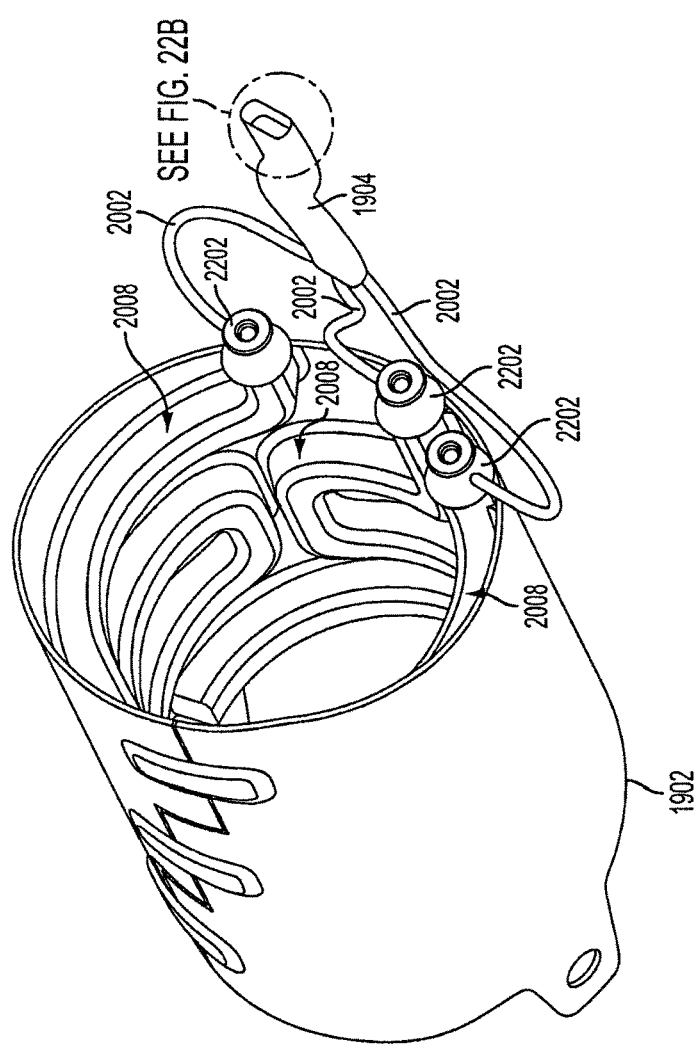
FIG. 22A is a view of a gastric skirt having one or more inflatable chambers.

FIG. 22A is a view of a gastric skirt 1902 having one or more inflatable chambers 2008. In an embodiment, each of the lumens 2002 is connected to a valve 2202. Each valve 2002 is connected to a separate inflatable chamber. In another embodiment, a single valve is located on the tube 1904 near the inlet 1906, and controls delivery to all of the chambers 2008. Each lumen 2002 can also be directly connected to a separate inflatable chamber 2008 without a valve 2002.

FIG. 22B is a view of a cavity 2204 of a triple-lumen tube 1904. The tube 1904 has a cavity 2204 that contains three separate lumens 2002. Each of the lumens 2002 is connected via a valve 2002 to a separate inflatable chamber, as shown in FIG. 22A. In an embodiment, each of the lumens 2002 has a separate inlet so that a different fluid can be administered through each of the lumens 2002. In another embodiment, the tube 1904 can include switches which allow an operator to close or open certain lumens 2002. Thus, a single inlet can be used to administer the fluid; however, a switch or valve can be used to close the second and third lumens, while allowing the fluid to pass through the first lumen and into the first chamber.

Figure 23:
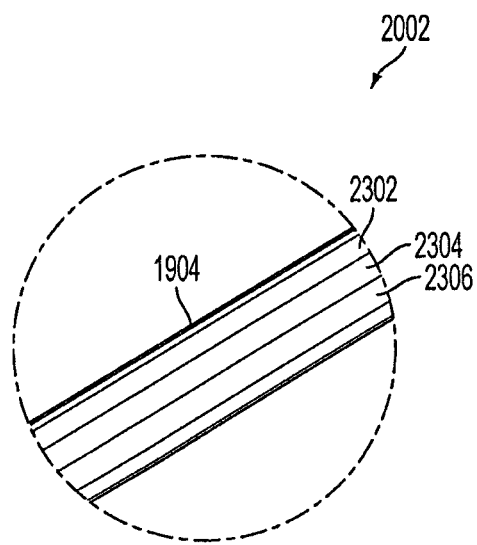
FIG. 23 is a view of the interior of a triple-lumen tube.

FIG. 23 is a view of the interior of a triple-lumen tube. The tube 1904 includes three separate lumens, a first lumen 2302, a second lumen 2304, and a third lumen 2306. Surrounding the lumens 2002 is the tube 1904. The tube 1904 and the lumens 2002 are relatively flexible and may be made of a non-porous elastomer, such as, but not limited to, silicone, polypropylene, polyethylene terephthalate, polytetrafluoroethylene, polyaryletherketone, nylon, fluorinated ethylene propylene, polybutester, or any combination thereof. In an embodiment, the tube 1904 and the lumens 2002 are made of the same material. In an alternative embodiment, the tube 1904 and the lumens 2002 are made of different materials.

Figure 24:
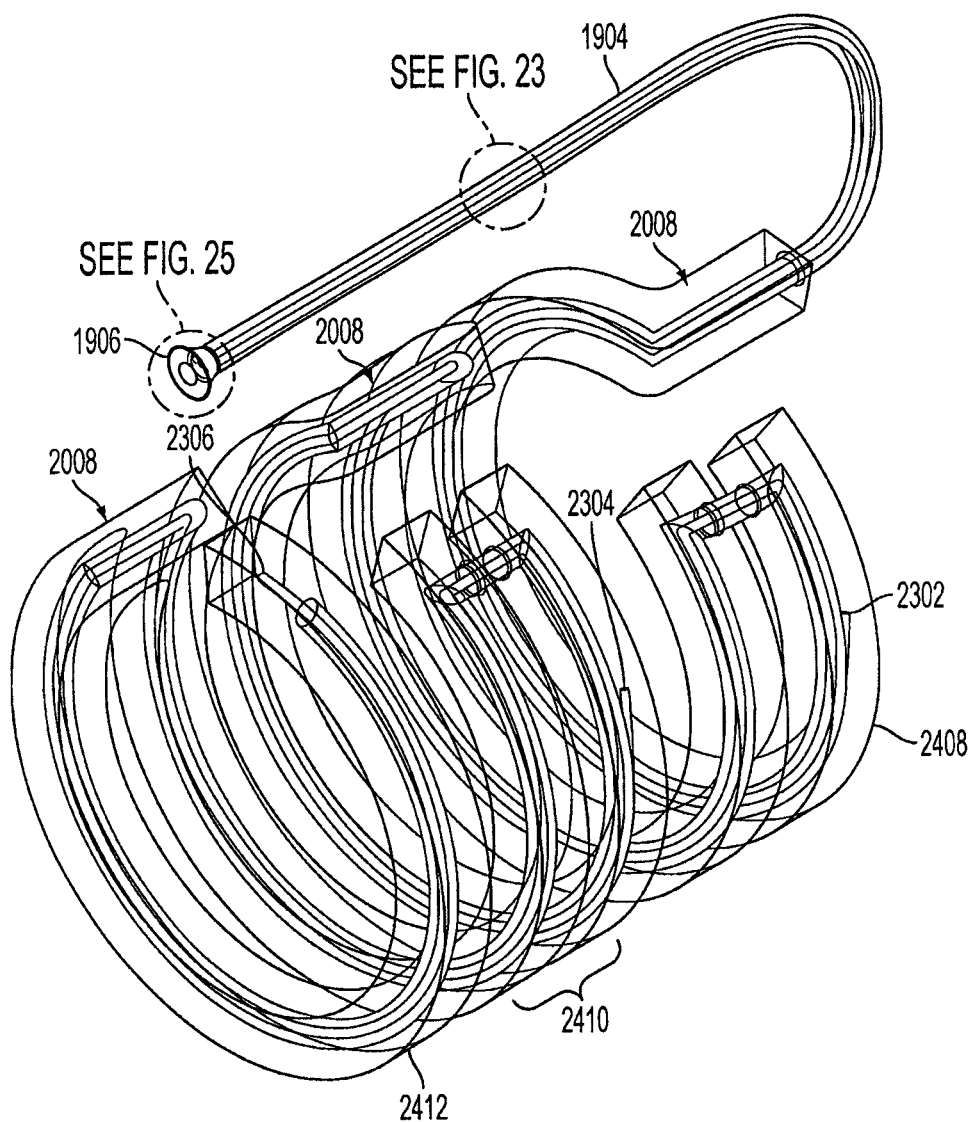
FIG. 24 is an interior view of an inflatable gastric skirt.

FIG. 24 is an interior view of an inflatable gastric skirt. In an embodiment, the tube 1904 has a staggered lumen design, so that each of the three lumens has a different length. The first lumen 2302 outputs into the first chamber 2408, the second lumen 2304 outputs into the second chamber 2410, and the third lumen 2306 outputs into the third chamber 2412. In an embodiment, the third lumen 2306 is longer than the second lumen 2304, and the second lumen 2304 is longer than the first lumen 2302, thus creating a staggered lumen design within the tube 1904. In another embodiment, each of the lumens 2002 in the tube 1904 has approximately the same length, and each lumen directly connects to its respective chamber.

In an embodiment, the chambers 2008 are relatively flexible or semi-flexible and may be made of a non-porous elastomer such as, but not limited to, silicone, polypropylene, polyethylene terephthalate, polytetrafluoroethylene, polyaryletherketone, nylon, fluorinated ethylene propylene, polybutester, or any combination thereof. In an embodiment, certain chambers can be selectively filled with fluid. For example, fluid can be administered to only the first chamber 2408 and the third chamber 2412, leaving the second chamber 2410 unfilled or deflated. In another embodiment, each of the chambers 2008 can be inflated to different fluid amounts resulting in different pressure levels within each chamber.

The fluid administered into each chamber 2008 can include saline, air, water, gel, gas, or any other biocompatible fluid or viscous solid. In a preferred embodiment, the fluid is concentrated saline. In another embodiment, the fluid includes methylene blue. Different fluids can be administered through each lumen, thus allowing each chamber to be filled with a different amount and/or type of fluid. For example, the fluid administered through the first lumen 2302 and the second lumen 2304 can be saline, and the fluid administered through the third lumen 2306 can be a gas.

Figure 25:
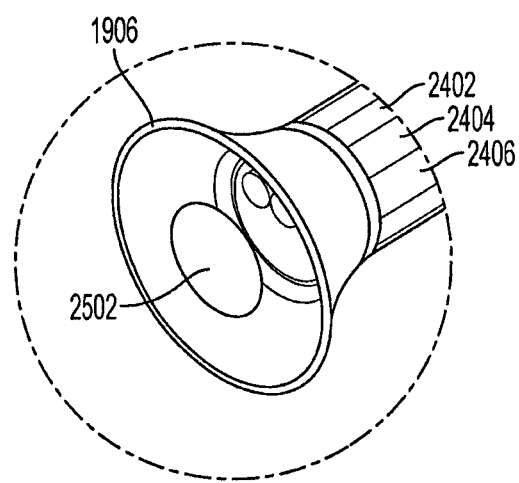
FIG. 25 is a view of a triple-lumen port inlet.

FIG. 25 is a view of a triple-lumen inlet port. The inlet 1906 includes an access hole 2502 or a septum 2502 that covers all the lumen openings. A needle may be used to pierce the septum 2502 and allow a healthcare professional to fill fluid into the lumens 2302, 2304, and 2306. The septum 2502 may have a visible marker on top to indicate where the needle should be positioned for filling each of the lumens. The septum 2502 may automatically be sealed when the needle is removed to prevent fluid for exiting the lumens. In one embodiment, the inlet 1906 is made of a semi-rigid elastomer.

Figure 26:
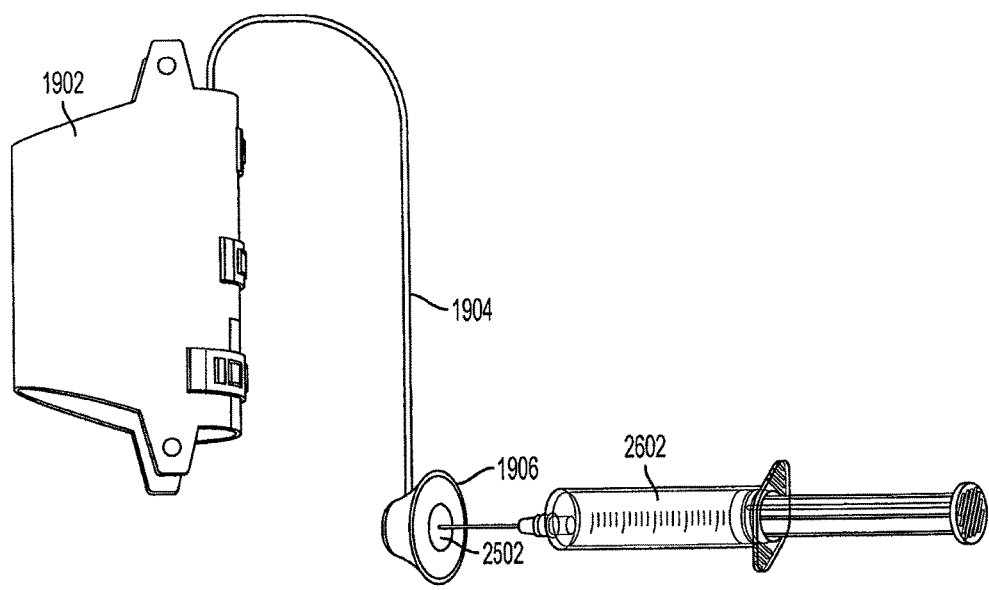
FIG. 26 is view of an inflatable gastric skirt and an inflation device.

FIG. 26 is a view of an inflatable gastric skirt and an inflation device. In an embodiment, to inflate the gastric skirt, a non-coring needle and syringe 2602 can be used to administer fluid to the access hole or septum 2502. To deflate the chambers 2008, the inlet 1906 is connected to a suction device 2602 which pulls the fluid out from the chambers 2008 or the needle 2602 can be reinserted through the septum 2502 which is used to remove the fluid from the lumens, which results in fluid being removed from the chambers 2008. The suction device 2602 can be, for example, a syringe, a vacuum, or any other means to withdraw inflation fluid from the chambers 2008. In another embodiment, the inlet 1906 can be connected to an automated system for inflation and deflation of the chambers, so that manual adjustment of the gastric skirt 1902 is not required.

In an embodiment, the inlet 1906 includes a reservoir which holds fluid. For example, the reservoir can be pre-filled during insertion of the gastric skirt 1902 around the stomach. The reservoir can automatically administer fluid to the lumens 2002 over a pre-determined time period. In another embodiment, the reservoir can include dual tanks, one tank to deliver fluid to the chamber, and another tank to remove fluid from the chamber. The dual tanks can automatically inflate or deflate the chambers 2008 based on fluid pressure changes resulting from movement of the patient and the stomach.

The gastric skirt 1902 can have a microprocessor and sensors attached thereto to determine the fluid pressure and free volume within each chamber. Upon receipt of the fluid pressure and free volume data, the microprocessor can be used to activate fluid transfer between the different chambers in order to compensate for fluid displacement due to patient and stomach movements. The fluid transfer can ensure that a desired amount of pressure is constantly being applied from each chamber to the stomach. In another embodiment, the microprocessor can control the reservoir, and administer or draw fluid based on the sensor readings.

The gastric skirt 1902 may include at least one pressure sensor located within the tube 1904 and at least one pressure sensors located within the chambers 2008 to measure fluid movement and fluid pressure within the chambers 2008. A receiver located within the gastric skirt 1902 can transmit data to a remote controller, such as, for example, an external handheld computer, desktop computer, monitoring system, or an online web-based monitoring portal.

In an embodiment, the remote controller includes microprocessors to analyze the data for pressure variations and determine optimal fill volumes for the chambers 2008. This analysis can assist a healthcare professional in adjusting the inflation levels in the chambers 2008. Alternatively, the data can be used by the remote controller to automatically adjust the fluid levels based on pre-determined constriction pressures. In an embodiment, each of the different chambers can have a separate pressure sensor, allowing monitoring and adjustment of fluid within each individual chamber.

Each chamber can have multiple entry points for the lumens, so that a blockage in one portion of a lumen or a chamber will not prevent the chamber from being filled with fluid. For example, the first lumen 2302 can have multiple branches which allow inflation fluid into the first chamber 2408. Thus, if one of the branches is blocked or obstructed, the other branches on the first lumen 2302 will continue to fill the first chamber 2408.

In another embodiment, the reservoir can be controlled via an implantable pump that is powered by an implantable energy source, such as batteries or capacitors. Alternatively, the pump can be powered by a passive device located outside the body via energy transferred through, for example, radio frequency, induction, or electromagnetic energy.

In another embodiment, the tube 1904 is removable. After the gastric skirt 1902 has been placed around the stomach, and adjusted to provide a desired constriction pressure, the healthcare professional can remove the tube 1904. In this embodiment, the gastric skirt 1902 is designed to be inflated and adjusted only at the time of insertion. Following the initial inflation and adjustment, the outlet 1908 can be detached from the gastric skirt 1902, and the tube 1904 can be removed from the body. In order to inflate or deflate the gastric skirt 1902 after the initial surgery to insert the gastric skirt 1902, the outlet 1908 of the tube 1904 needs to be re-attached to the gastric skirt 1902 via a surgical procedure.

Figure 27:
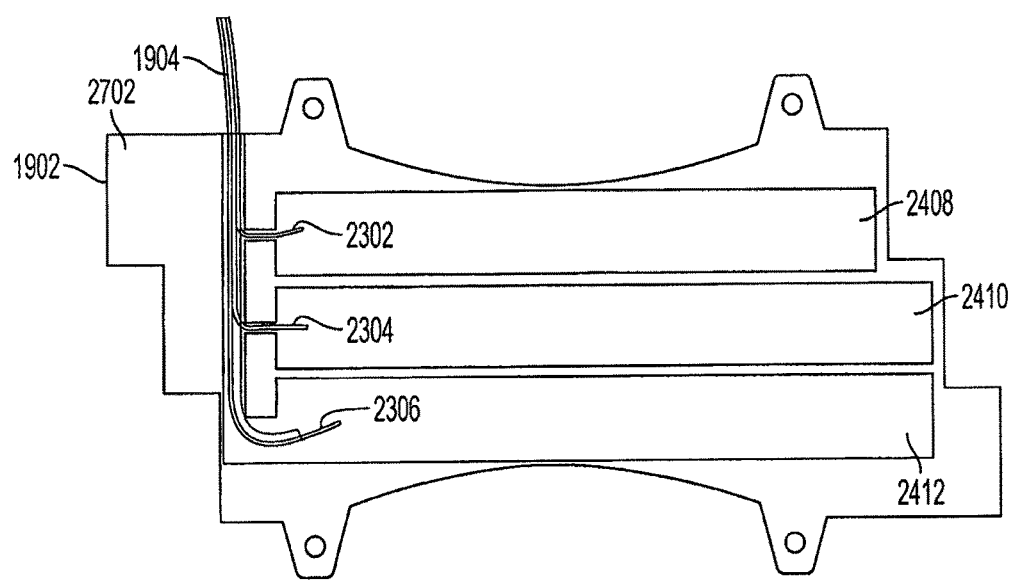
FIG. 27 is a view of a laid-open inflatable gastric skirt.

FIG. 27 is a view of a laid-open inflatable gastric skirt. In an embodiment, the chambers 2408, 2410 and 2412 are attached to or integrated with an interior portion 2702 of the gastric skirt 1902. The first lumen 2302 has an output into the first chamber 2408, the second lumen 2304 has an output into the second chamber 2410, and the third lumen 2306 has an output into the third chamber 2412. In another embodiment, a single lumen can be utilized instead of multiple lumens. The single lumen can have outlets branching into each of the chambers 2408, 2410 and 2412.

Figure 28:
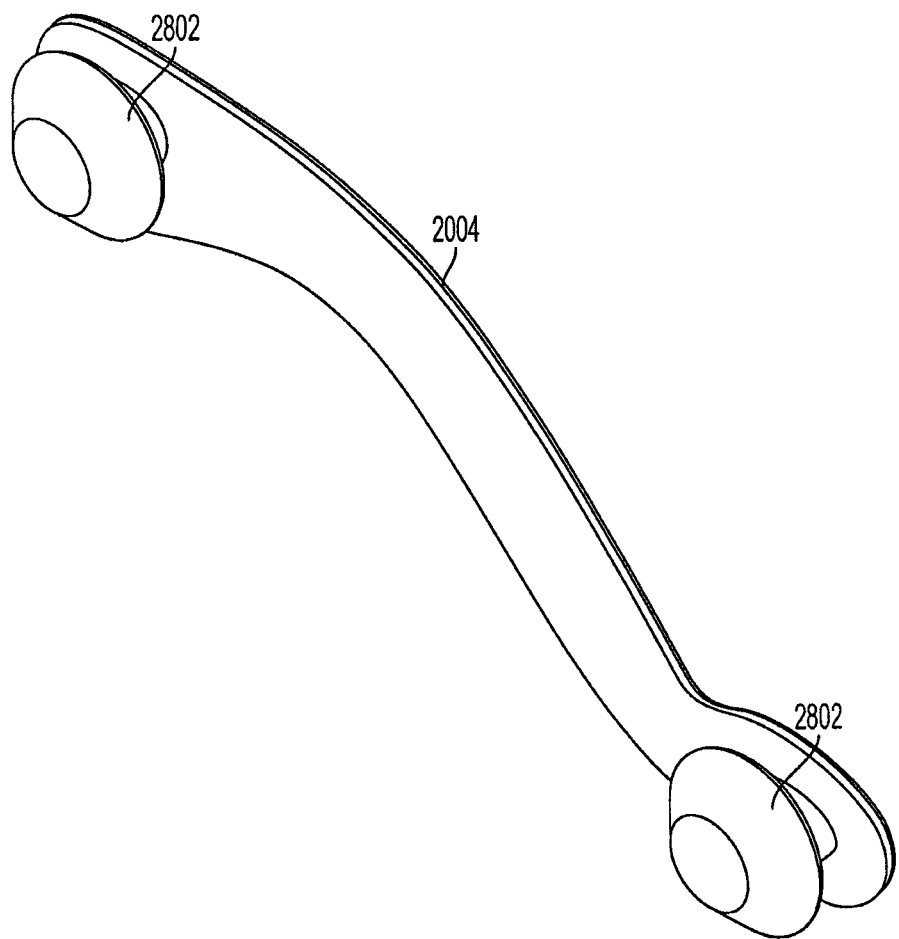
FIG. 28 is a view of a connector strap.

FIG. 28 is a view of a connector strap. The connector strap 2004 has buttons 2802 that are used to secure the connector strap 2004 to the upper collar 2006 and the gastric skirt 1902. The buttons 2802 are configured to snap into the connector holes 2102 on the gastric skirt 1902 and corresponding connector holes on the upper collar 2006. The connector strap 2004 is relatively flexible or semi-flexible and may be made of a non-porous elastomer, such as, but not limited to, silicone, polypropylene, polyethylene terephthalate, polytetrafluoroethylene, polyaryletherketone, nylon, fluorinated ethylene propylene, polybutester, or any combination thereof. The connection means between the upper collar 2006 and the gastric skirt 1902 is not limited to the connector strap 2004, and can be any type of connector which allows a limited movement of the upper collar 2006 irrespective of the movement of the gastric skirt 1902.

Figure 29:
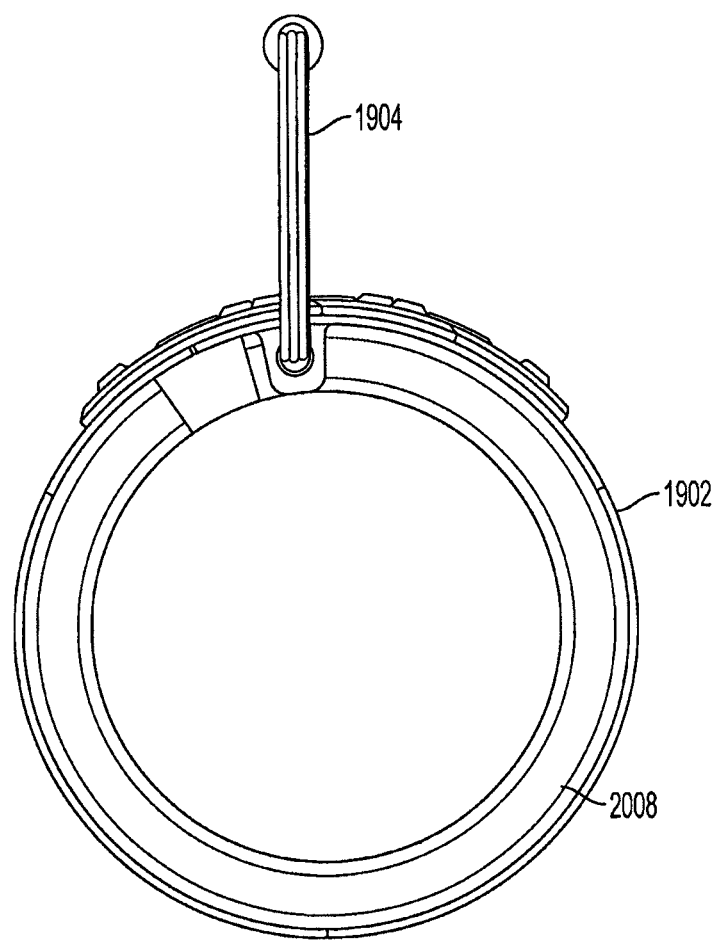
FIG. 29 is a lateral view of an inflatable gastric skirt.

FIG. 29 is a lateral view of the inflatable gastric skirt. In an embodiment, the chambers 2008 can have a thickness of 0.05 millimeters to 0.5 millimeters in a collapsed state. In an inflated state, the chambers can have a thickness of 0.5 millimeters to 1.5 centimeters. The thickness of the chambers 2008 can be varied based on a desired constriction pressure. Furthermore, each of the different chambers 2008 can be inflated to a different thickness or filled to provide a different level of rigidity.

Figure 30:
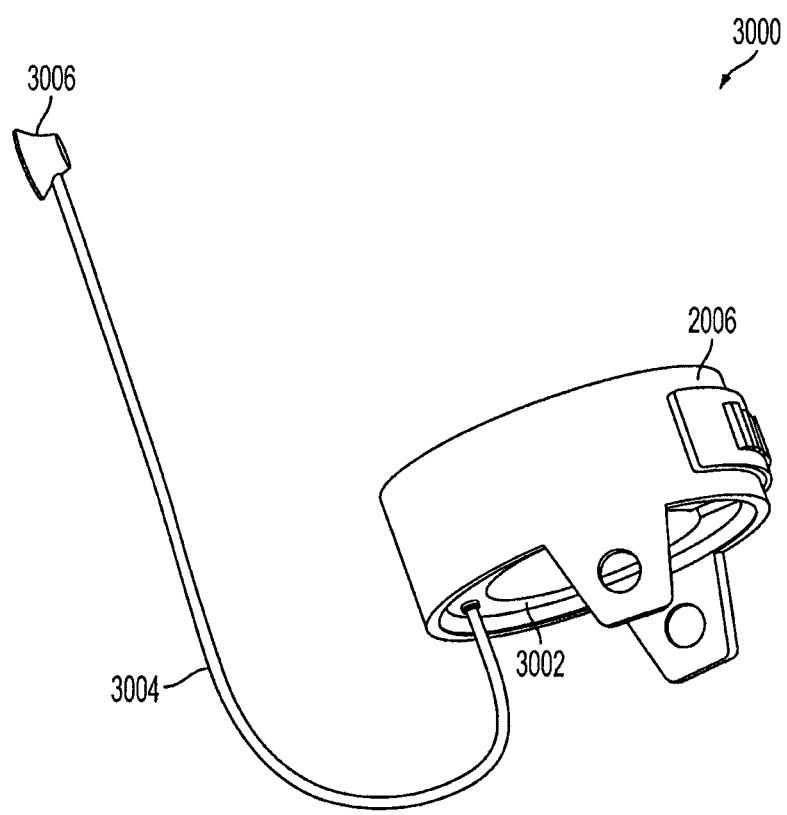
FIG. 30 is a view of an inflatable collar.

FIG. 30 is a view of an inflatable collar. In an embodiment, an inflatable collar 3002 can be utilized for a harness system. The inflatable collar 3000 has a chamber 3002 and a tube 3004. In an embodiment, the inflatable collar 3000 has multiple chambers similar to the chambers 2008 described above for the gastric skirt 1902. The tube 3004 can have a single lumen or multiple lumens similar to the tube 1904.

The inflatable collar 3002 can be used to apply pressure to the antral portion and/or to the lower esophageal/cardia portion of the stomach.

Figure 31:
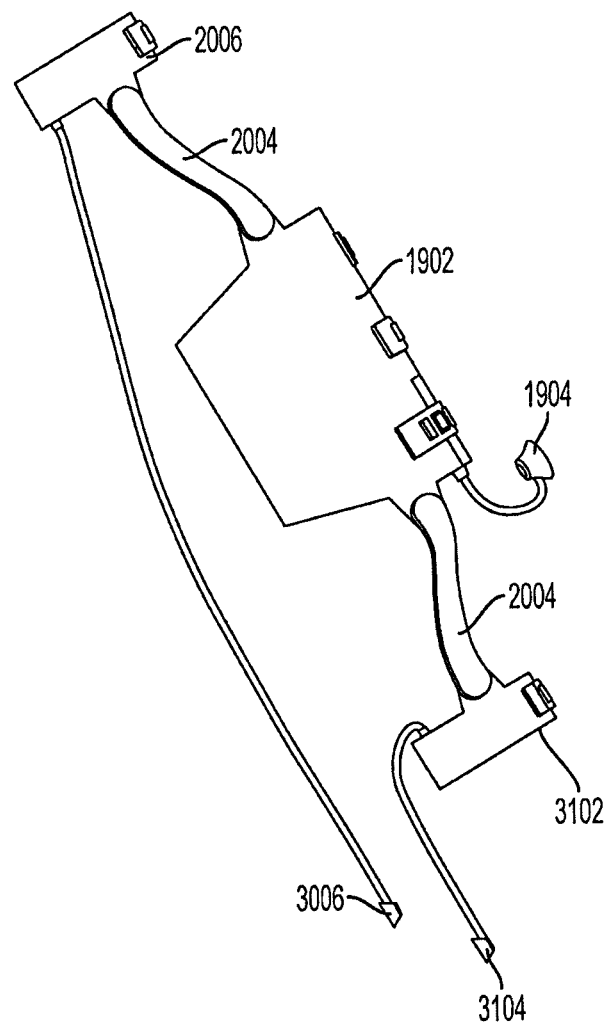
FIG. 31 is a view of an inflatable gastric skirt with dual inflatable collars.

FIG. 31 is a view of an inflatable gastric skirt with dual inflatable collars. In an embodiment, the lower collar 3102, also known as the antral collar, is placed around a lower portion of the stomach near the angular receiver at the pylorus, also known as the pyloric antrum receiver. In an embodiment, the lower collar 3102 is large enough in diameter to encircle part of the lower portion of the stomach near the pylorus, but small enough so that it cannot encircle the larger diameter portion of the small intestine. The lower collar 3102 is connected to the gastric skirt 1902 via the connector straps 2004. This system prevents the lower collar 3102 from moving down into the small intestine, and helps to anchor the gastric skirt 1902 in place. Furthermore, the lower collar 3102 may assist in slowing the gastric emptying from the stomach into the small intestine.

In an embodiment, the lower collar 3102 and the upper collar 3000 are both inflatable. The lower collar has a port 3104, and the upper collar has a separate port 3006. These ports operate in a similar fashion to the port 1906 that is used to inflate the chambers of the gastric skirt 1902. In another embodiment, the tube 1904 can be connected to the gastric skirt 1902, the lower collar 3102, and the upper collar 3000, so that a single tube 1904 is used to fill or inflate all of the chambers.

Figure 32:
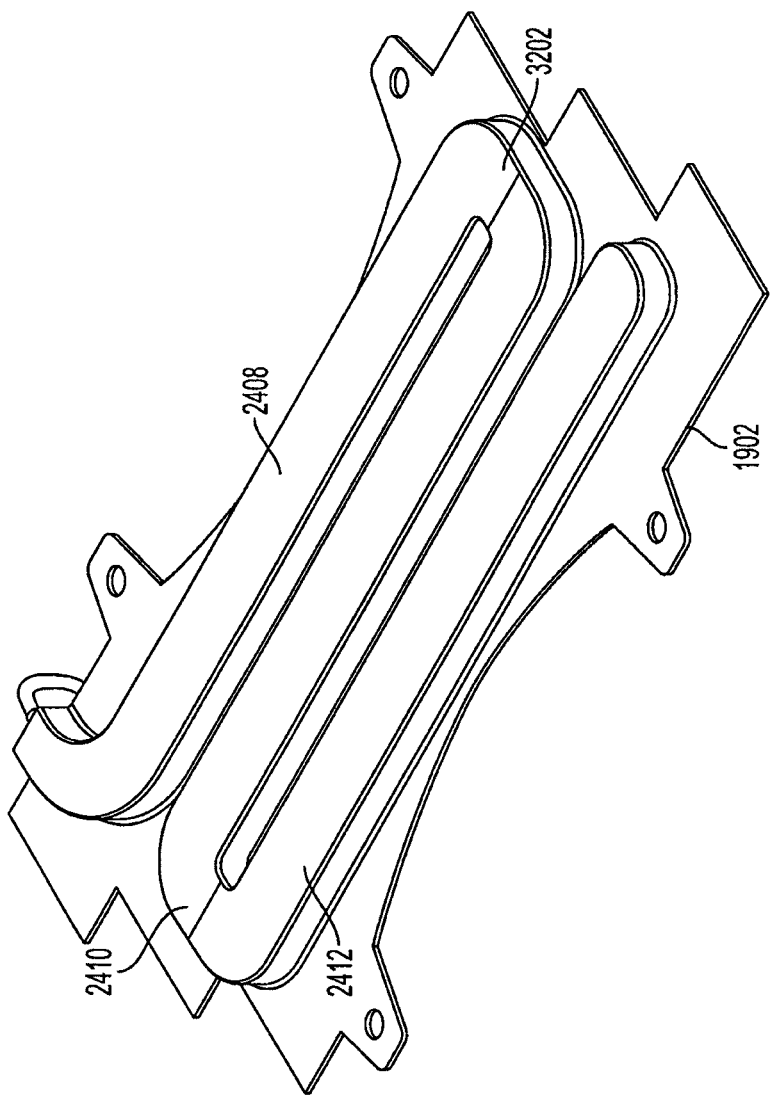
FIG. 32 is a view of the internal surface of an inflatable gastric skirt.

FIG. 32 is a view of an internal surface of an inflatable gastric skirt. In an embodiment, the first chamber 2408, the second chamber 2410, and the third chamber 2412 may be enclosed within a covering 3202. The lumens 2002 are enclosed within the covering 3202 in a staggered fashion as described above. In an alternative embodiment, a single inflatable chamber is utilized, and can be inflated using a single-lumen port.

Figure 33:
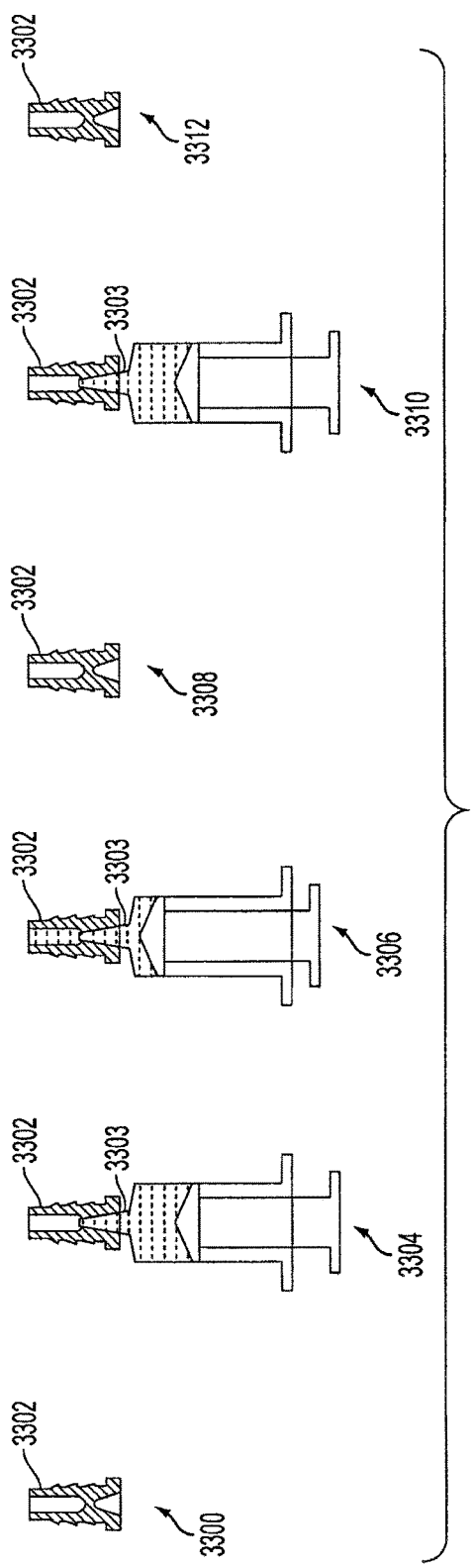
FIG. 33 is a view of a valve and the steps of inflation and deflation.

FIG. 33 is a view of a valve and the steps of inflation and deflation. In an embodiment, the valve 3302 is fitted at the inlet 1906 of the tube 1904. The valve 3302 has a slitted diaphragm to allow a syringe nozzle to enter. In step 3300, the valve is in a closed position. In step 3304, a syringe nozzle 3303 is inserted through the slitted diaphragm of the valve 3302. The slitted diaphragm opens up and allows fluid to be inserted through the syringe nozzle 3303. In step 3306, the fluid is inserted through the open valve 3302. In step 3308, the syringe nozzle 3303 is removed from the valve 3302, and the slitted diaphragm of the valve 3302 returns to a closed position.

In an embodiment, to deflate or remove fluid from the chambers, the syringe nozzle 3303 is inserted into the slitted diaphragm of the valve 3302 as shown in step 3310. The syringe nozzle 3303 is used to aspirate the inflation fluid from the lumens and chamber, thereby deflating or removing fluid from the chambers. In step 3312, the syringe nozzle 3303 is removed from the valve 3302 and the slitted diaphragm returns to a closed position. In another embodiment, the inlet 1906 can have a similar design as the valve described in FIG. 33.

Figure 34:
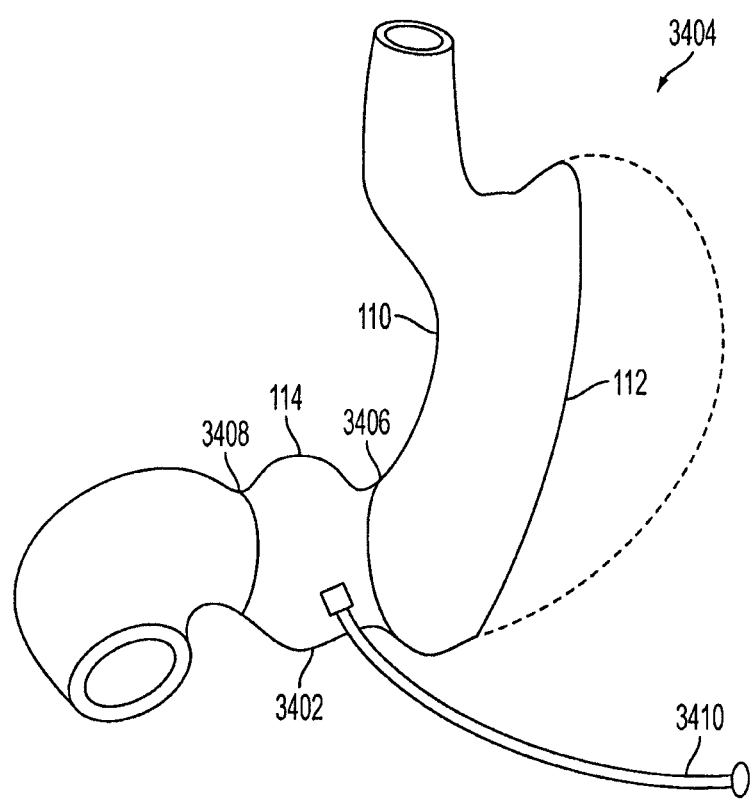
FIG. 34 is a view of an inflatable antral skirt.

FIG. 34 is a view of an inflatable antral skirt. In an embodiment, the antral skirt 3402 can be positioned around the pyloric antrum 114, which is located between the pyloric sphincter 3408 and the angular receiver 3406 in the lower part of the stomach 3404. In an embodiment, the antral skirt 3402 is designed to be placed around a stomach that has undergone a VSG procedure, which is also known as sleeve gastrectomy, vertical gastrectomy, greater curvature gastrectomy, parietal gastrectomy, gastric reduction, longitudinal gastrectomy, or vertical gastroplasty. In the VSG procedure, the stomach 3404 is restricted by stapling and dividing it vertically and removing more than 85% of its surface area. As shown in FIG. 34, the greater curvature 112 of the stomach 3404 is taken in closer to the lesser curvature 110, creating a sleeve-shaped stomach 3404. In an embodiment, the antral skirt 3402 is configured to cover at least 14 square centimeters of the outer surface of the pyloric antrum 114. Thus, the antral skirt 3402 has a surface area of at least 14 square centimeters. In an embodiment, the antral skirt 3402 has a length of at least 10 centimeters and a width of at least 4 centimeters. In one embodiment, the thickness of the antral skirt 3402 is up to about 1/35,000th of an inch.

In an embodiment, the antral skirt 3402 is inflatable or fillable with fluid through a tube 3410, which operates similar to the tube 1904 described above for the gastric skirt 1902. The antral skirt 3402 can be inflated and deflated to provide a desired constriction level around the pyloric antrum 114. In another embodiment, the antral skirt 3402 can be applied around the pyloric antrum 114 of a stomach that has not undergone a VSG procedure. In yet another embodiment, the antral skirt 3402 can be applied in conjunction with a gastric skirt or other type of gastric constriction device that is placed around the body or fundus of the stomach.

Inflation of the antral skirt 3402 constricts the pyloric antrum 114. The pyloric antrum 114 is a portion of the stomach where food and particles are collected and pumped into the lower intestine. The pyloric antrum 114 also contains receptors that provide indications of fullness to the brain. When food is pumped into the pyloric antrum 114 from the stomach, the pyloric antrum 114 expands, and receptors provide an indication that the stomach is full. This results in a pumping action by the pyloric antrum 114 to empty the stomach contents into the intestine. The antral skirt 3402 provides a constant restriction to the pyloric antrum, which leads to early gastric emptying. This mechanism is described in more detail by the disclosure below.

The antral skirt 3402 is relatively flexible or semi-flexible and may be made of a non-porous elastomer, such as, but not limited to, silicone, polypropylene, polyethylene terephthalate, polytetrafluoroethylene, polyaryletherketone, nylon, fluorinated ethylene propylene, polybutester, or any combination thereof. In another embodiment, the antral skirt 3402 can be made of a biodegradable mesh.

Figure 35:
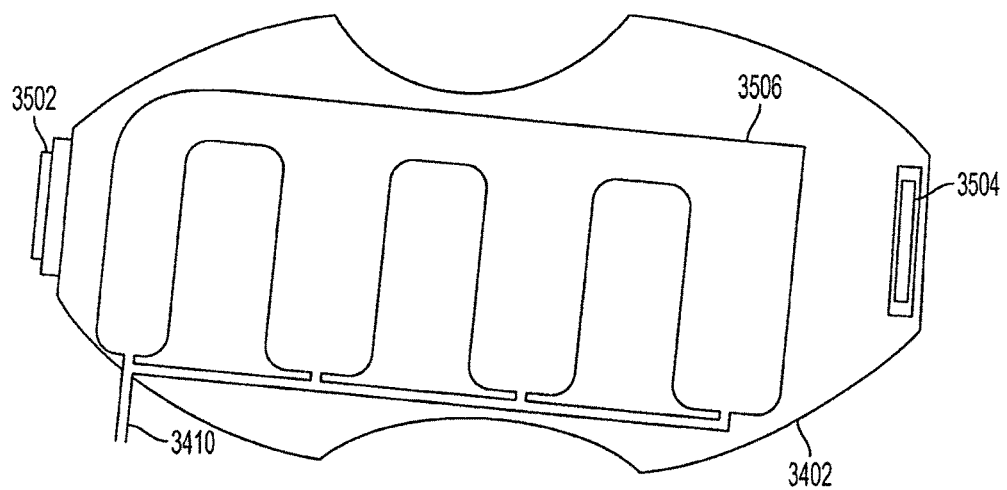
FIG. 35 is a laid-open view of an inflatable antral skirt.

FIG. 35 is a laid-open view of an inflatable antral skirt. In an embodiment, the antral skirt 3402 includes an inflatable chamber 3506. The antral skirt 3402 may or may not include an inflatable chamber 3506. The inflatable chamber 3506 can be inflated or filled with inflation fluid through the tube 3410. The antral skirt 3402 includes a male connector 3502 and an opposing female connector 3504. When then antral skirt 3402 is positioned around the pyloric antrum, the male connector 3502 and the female connector 3504 interlock to securely hold the antral skirt 3402 in place. The connection means is not limited to the embodiment shown in FIG. 35, and the antral skirt 3402 can be securely held in place by clips, straps, sutures, stitching, staples, other types of connectors, and/or other attachment means.

Figure 36:
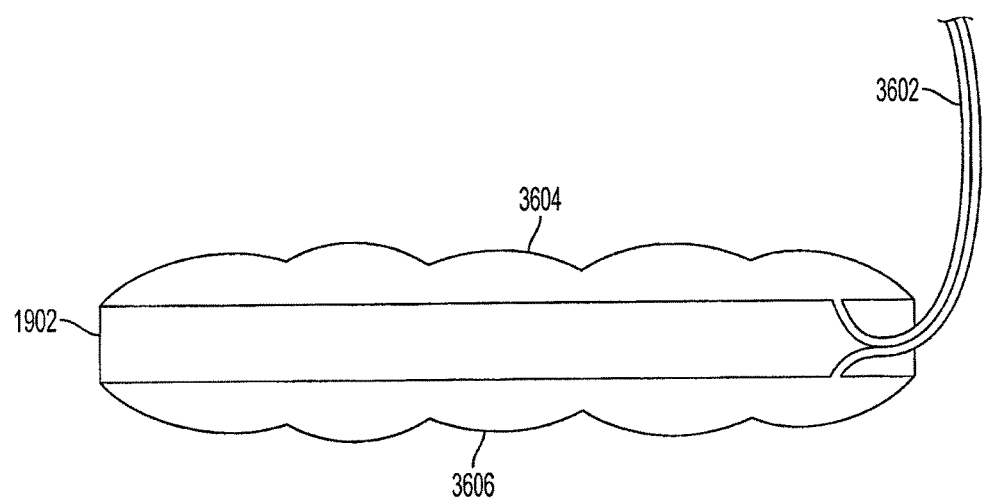
FIG. 36 is a view of a double-side inflatable gastric skirt.

FIG. 36 is a view of a double-side inflatable gastric skirt. In an embodiment, the gastric skirt 1902 includes a top inflatable layer 3604 attached to an exterior surface of the gastric skirt 1902 and a bottom inflatable layer 3606 attached to an interior surface of the gastric skirt 1902. The top inflatable layer 3604 provides cushions from pressure exerted onto the stomach from other body organs that are adjacent to the stomach. The bottom inflatable layer 3606 provides constriction pressure on the stomach as described above. A double-lumen port 3602 provides separate inflation fluid to each of the inflatable layers. In an embodiment, the top inflatable layer 3604 and bottom inflatable layer 3606 can include multiple inflatable or fillable chambers. Each of the lumens in the double-lumen port 3602 can each contain multiple lumens to deliver different fluids to each of the multiple chambers within each inflatable layer.

Figure 37:
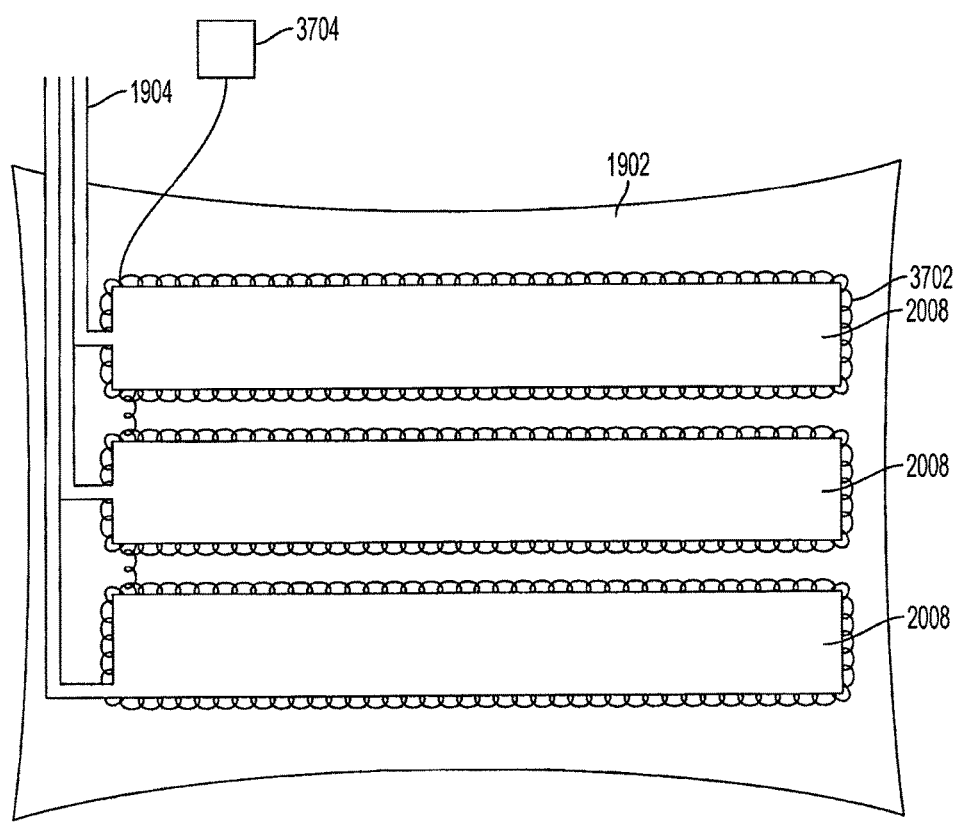
FIG. 37 is a view of an inflatable gastric skirt with radio frequency coils.

FIG. 37 is a view of an inflatable gastric skirt with radio-frequency (RF) coils. In an embodiment, each of the inflatable chambers 2008 has a RF coil 3702 surrounding the exterior of the chamber 2008. The RF coils 3702 are activated when a RF receiver 3704, either coupled to the gastric skirt 1902, or embedded within the gastric skirt 1902, receives an activation signal from an energy device, such as an RF generator, controller or transmitter. In an embodiment, the energy device is located outside of the patient's body and transmits wireless energy signals to the RF receiver 3704. The RF receiver 3704 can be used to store energy or the energy signals. In another embodiment, the energy device can be located inside the patient's body. In an embodiment, the RF coils 3702 provide RF energy, such as heat and ultrasonic energy, to the exterior stomach wall, and create scarring in the shape of the RF coils 3702 in the exterior stomach wall. The scarred tissue reduces the stomach volume.

In an embodiment, immediately after the tissue scarring process in completed the chambers 2008 can be filled with a cooled fluid, such as cooled saline. The cooled fluid may assist in better healing of the scarred tissue. Furthermore, once the chambers 2008 are inflated, they inflate into the space created by the scarred tissue, providing localized cushioning of the scarred regions. When the chambers 2008 expand or fill into the scarred tissue region that has been indented into the exterior stomach wall, the gastric skirt 1902 is secured into its intended site.

In an embodiment, the RF coils 3702 may be covered with a sleeve or pouch made from Teflon®, Dacron®, ePTFE, or any combination thereof. The sleeve is glued or sutured to the gastric skirt 1902 and/or the chambers 2008. In another embodiment, the sleeve is molded with the gastric skirt 1902 and/the chambers 2008 to form a single molded structure.

Figure 38:
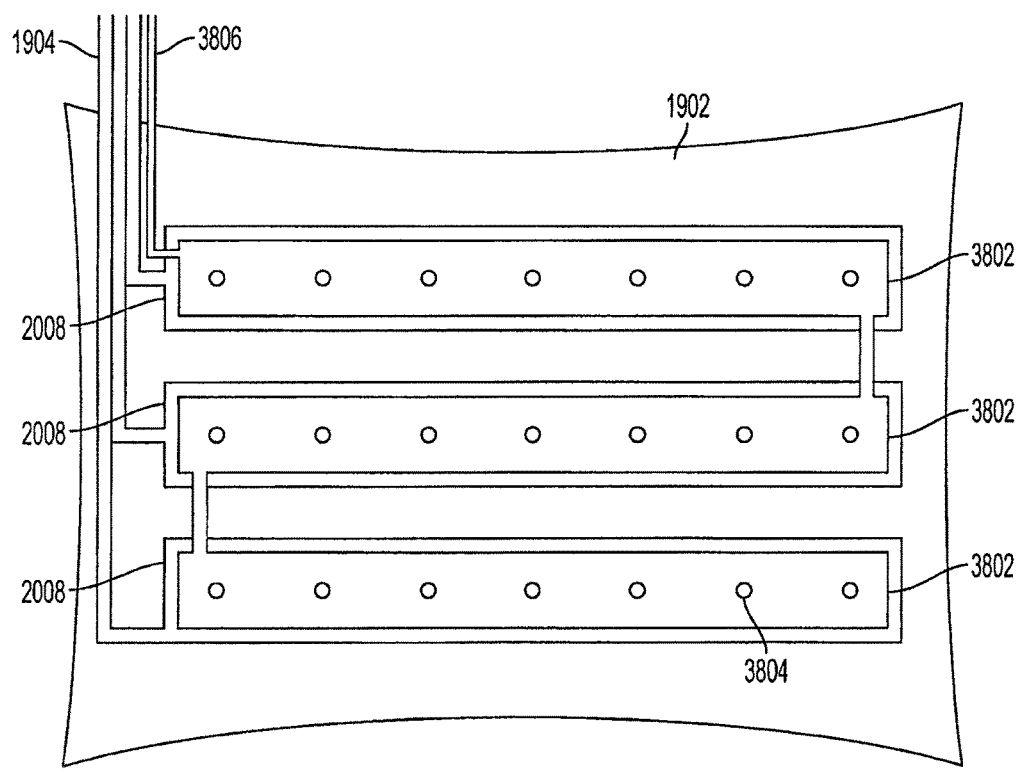
FIG. 38 is a view of an inflatable gastric skirt with steam ablation holes.

FIG. 38 is a view of an inflatable gastric skirt with steam ablation holes. Each of the inflatable chambers 2008 are covered with a thin ablation layer 3802, which contain an ablation device, and have top holes 3804 to allow thermal energy in the form of steam to pass through and ablate the exterior stomach wall. Steam is delivered to the ablation layers 3802 via a steam receiver 3806. In an embodiment, the steam can be delivered through the tube 1904 prior to delivery of fluid to the chambers 2008. In another embodiment, thermal steam ablation can be used in conjunction with laser ablation to provide scarring of the stomach tissue.

Figure 39:
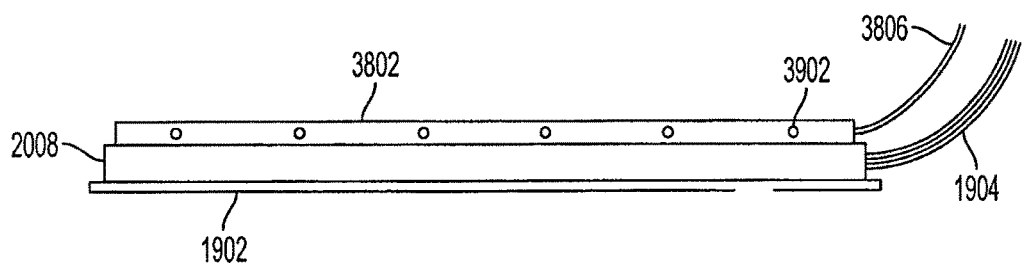
FIG. 39 is a lateral view of an inflatable gastric skirt with steam ablation holes.

FIG. 39 is a lateral view of an inflatable gastric skirt with steam ablation holes. The gastric skirt 1902 includes ablation layers 3802 on top of each of the chambers 2008. The ablation layers 3802 include side holes 3902. The top holes 3802 and the side holes 3902 allows steam ablation to create an indentation within the exterior stomach wall so that the stomach can accommodate the chambers 2008.

Figure 40:
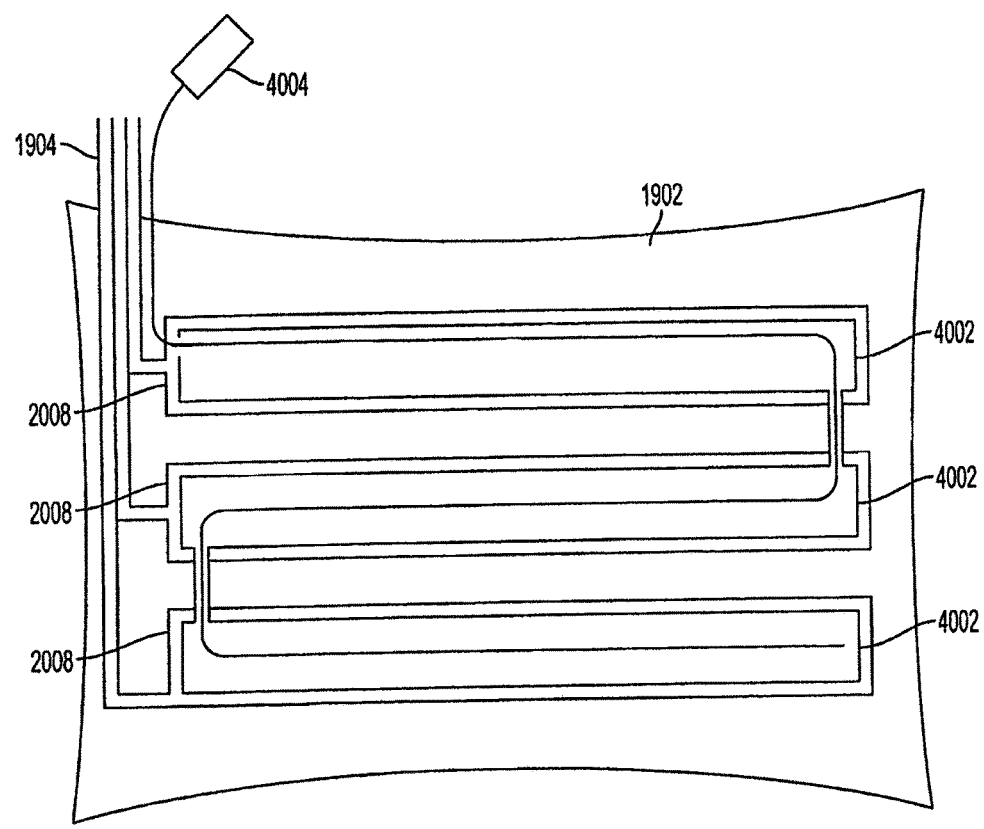
FIG. 40 is a view of an inflatable gastric skirt with an ultrasound probe.

FIG. 40 is a view of an inflatable gastric skirt with an ultrasound probe. The gastric skirt 1902 includes ultrasound layers 4002 on top of each of the chambers 2008. The ultrasound layers include an ultrasound receiver 4004 which delivers ultrasound waves to the exterior stomach wall. The ultrasound energy, such as ultrasonic waves, creates indentations within the exterior stomach wall so that the stomach can accommodate the chambers 2008. In an embodiment, the ultrasound receiver 4004 can be embedded within the gastric skirt 1902 and activated by a receiver or controller located outside of the patient's body.

In another embodiment, laser energy, heat, microwave radiation, high-intensity light, or other tissue scarring mechanisms can be used to deliver energy to scar the exterior stomach wall. In each of these embodiments, an implanted receiver and an external energy source, such as a generator located outside of the body, can be used to activate the tissue ablation device.

In another embodiment, the energy source is implanted with the body, and can be embedded within the gastric skirt 1902, embedded within the ablation layers, or located adjacent to the gastric skirt 1902.

In an embodiment, the ablation device can be activated by a remote or external controller, such as for example, an external handheld computer, desktop computer, monitoring system, or an online web-based monitoring portal. The remote controller ablation energy to be delivered remotely after the gastric skirt implantation surgery has been completed. The remote controller activates the transmission of energy from an external energy source to the transmitter, which in turn delivers energy to the ablation layer. The ablation device then emits the energy toward the outer surface of the stomach in order to ablate stomach tissue. In an embodiment, the energy emission to the stomach tissue can last from 0.5 seconds to 20 seconds, depending on a desired level of ablation or scarring.

In another embodiment, the ablation device is positioned on the exterior surface of the gastric skirt 1902. In this embodiment, the ablation device, such as an ultrasound probe, transmits ultrasound energy signals towards the outer surface of the stomach through the gastric skirt 1902.

In another embodiment, the gastric skirt 1902 is comprised of an interior elastomeric sheet and an exterior elastomeric sheet. The ablation device is sandwiched between the first elastomeric sheet and the second elastomeric sheet. In yet another embodiment, the ablation device is integral to an elastomeric casing, and is contained within the elastomeric casing.

Figure 41:
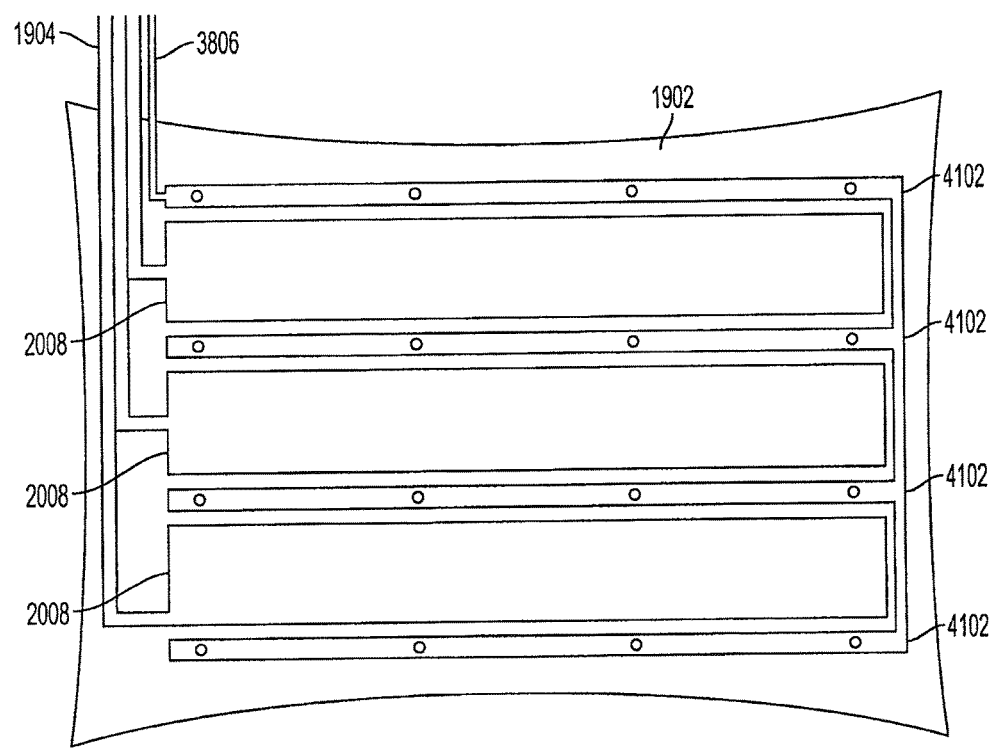
FIG. 41 is a view of an inflatable gastric skirt with alternating ablation and inflation chambers.

FIG. 41 is a view of an inflatable gastric skirt with alternating ablation layers and inflation chambers. In an embodiment, the thermal ablation layers 4102 are positioned in an alternating fashion with the chambers 2008. The thermal ablation layers 4102 are positioned between the chambers 2008, so that the inner surface of the gastric skirt 1902 has a smooth and even surface. In another embodiment, the ablation layers can be an ultrasound probe or RF coils positioned between the chambers 2008 in an alternating fashion as described above.

In another embodiment, different ablation layers can be activated to selectively scar different portions of the exterior stomach wall. For example, in the gastric skirt shown in FIG. 40, only two of the four ablation layers can be activated based on a desired area and amount of scarring. Furthermore, different ablation layers can be activated at different times so that a large portion of the stomach is not undergoing scarring at once, and the scarring procedure can be spread out over time.

In yet another embodiment, the chambers can be semiporous, allowing for fluid to leak onto the exterior stomach wall. The inflation fluid can be a neurotoxin, such as botulinum toxin types A, B, $C_1$, D, E, F and G. When the neurotoxin is administered at the site where the inflatable chambers contact the stomach, the site administered takes a relaxed muscle tone. The inflatable chambers would then fall into these regions with the relaxed muscle tone, securing the gastric skirt 1902 in its intended site.

In an alternative embodiment, the gastric skirt does not include inflatable or fillable chambers. Instead, the gastric skirt includes only an ablation or tissue scarring mechanism, such as, for example, RF coils, thermal ablation layers, or ultrasound layers, to deliver energy to the exterior tissue, surface, wall or lining of the stomach. In this embodiment, the gastric skirt can be applied around a portion of the stomach in order to ablate the stomach and reduce the internal volume of the stomach. The gastric skirt can provide a barrier between the scarred exterior stomach wall and other body organs. This allows the scarred tissue to heal faster and with a minimal risk of infections or complications, as opposed to normal scarring procedures where the scarred tissue is left exposed during healing.

In an embodiment, the antral skirt 3402 can include an ablation device, such as, for example, RF coils, thermal ablation layers, or ultrasound layers, in conjunction with fillable or inflatable chambers. The antral skirt 3402 can provide constriction as well as ablation or scarring to the pyloric antrum 114.

Figure 42:
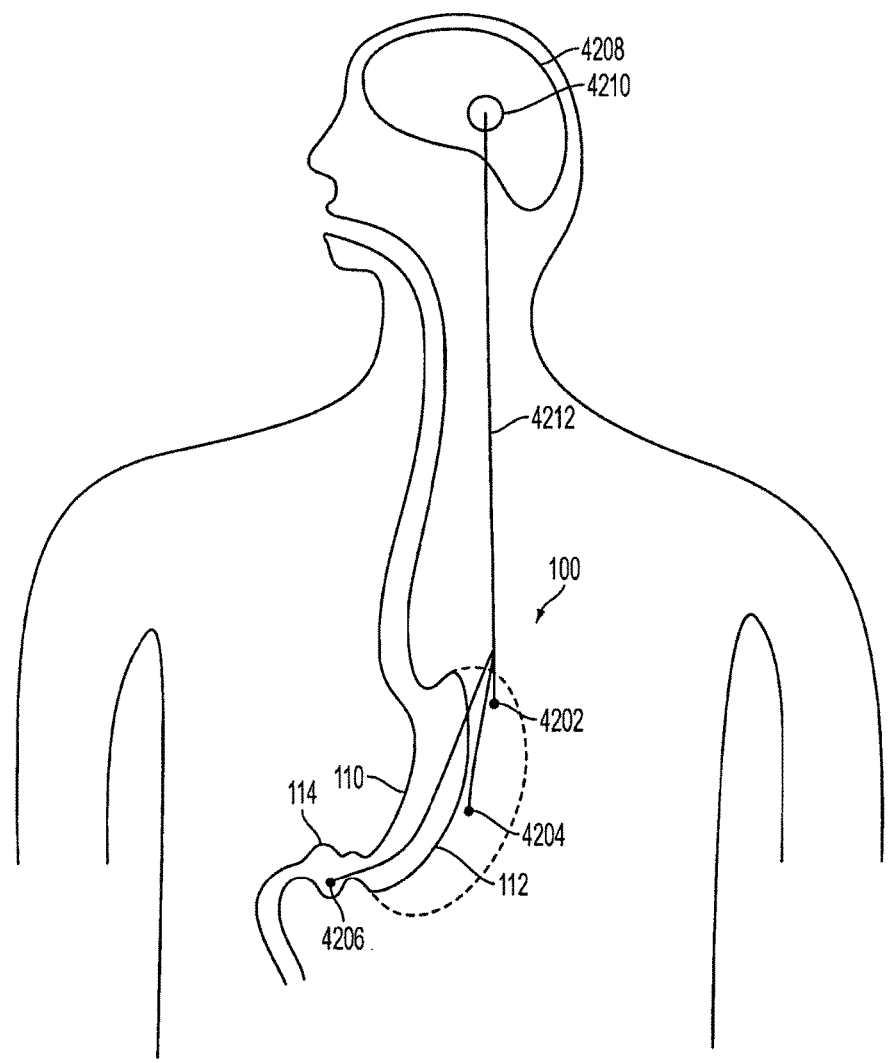
FIG. 42 is a view of a physiological connection between stomach receptors and a brain.

FIG. 42 is a view of a physiological connection between stomach receptors and a brain. After a VSG procedure, many of the cardia stretch receptors 4202 and the stomach body stretch receptors 4204 are removed. However, the pyloric antrum 114 is not modified by the VSG procedure, and the antral stretch receptors 4204 in the pyloric antrum 114 remain intact. Upon being filled with food and stomach contents, the pyloric antrum 114 expands, and the stretch receptors 4206 in the pyloric antrum 114 send neurological signals to the hypothalamus 4210 in the brain 4208, indicating the stomach is full. Upon receipt of these signals, the hypothalamus 4210 sends a signal via the afferent vagal nerve 4212 to the pyloric antrum 114 to pump out the food into the intestines.

The antral skirt 3402 provides a constant pressure around the pyloric antrum 114, so that when pyloric antrum 114 even slightly expands, the antral stretch receptors 4206 are constrained from further expansion. Upon being prevented from further expansion, the antral stretch receptors 4206 send a signal to the brain 4208, and in turn, the pyloric antrum 114 is caused to pump out food contents. The combination of the antral skirt 3402 and the antral stretch receptors 4206 create an equal and opposite reaction, causing a continual gastric emptying by the pyloric antrum 114. Thus, the invention takes advantage of the antral stretch receptors 4206 that remain after a VSG procedure in order to provide an indication of fullness to the brain 4208 and cause rapid and early gastric emptying.

Figure 43:
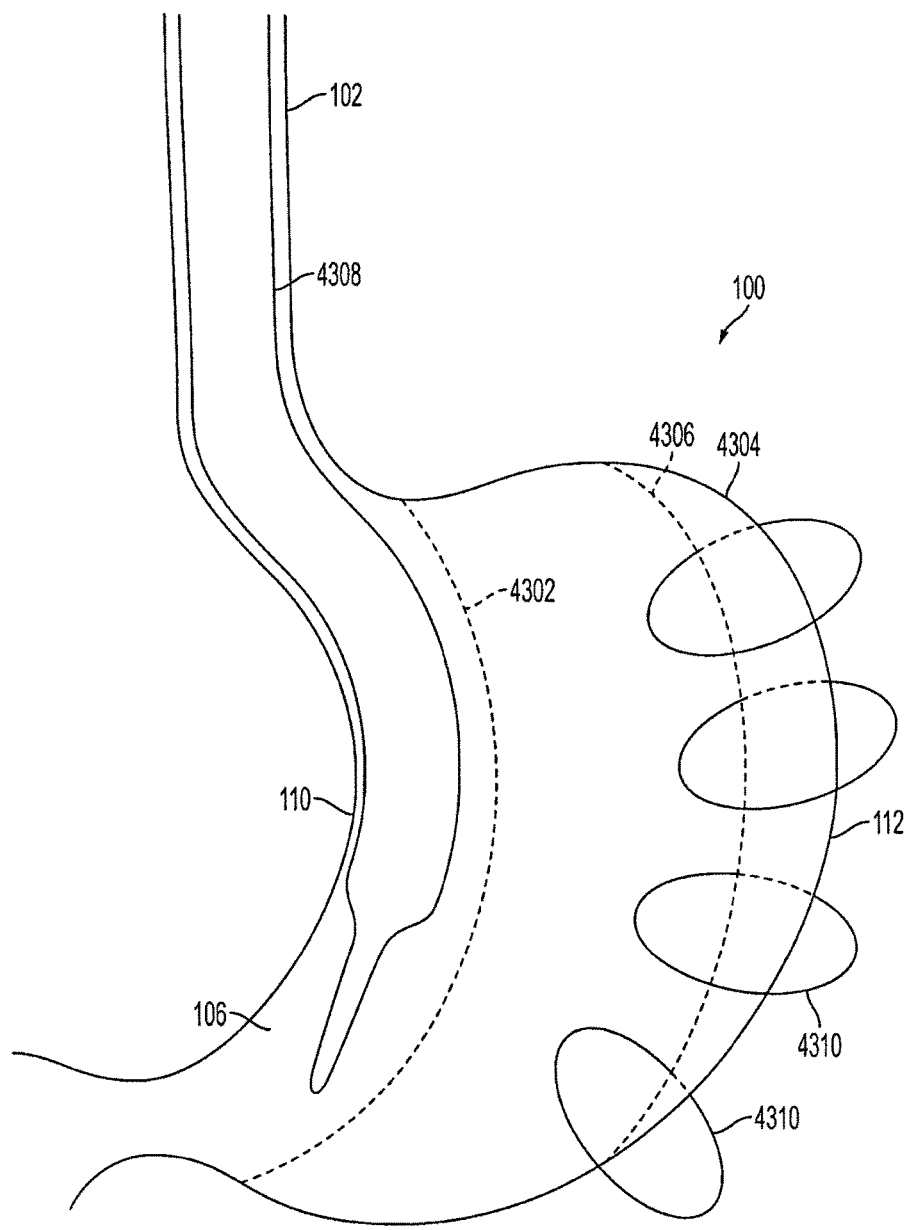
FIG. 43 is a view of a stomach prior to ligation.

FIG. 43 is a view of a stomach prior to ligation. In an embodiment, the gastric skirt 1902 is designed to accommodate a stomach that has undergone tucking and ligation procedures. Prior to placing the gastric skirt 1902 around the stomach 100, a linear portion of the greater curvature 112 is tucked inwards into the stomach 100 and towards the lesser curvature 110. As shown above in FIG. 1B, the inner lining 120 is depressed within the stomach 100 as a result of the tucking procedure, and the tucked-in portion 4302 occupies space within the body of the stomach 106. After the tucking procedure, a first untucked stomach portion 4304 and a second untucked stomach portion 4306. Thus, the internal volume of the stomach 100 is substantially decreased.

In an embodiment, in order to assist the healthcare provider in determining how far to tuck in the stomach, a bougie 4308 is endoscopically inserted through the esophagus 102 and into the stomach body 106 (Step 4702). The bougie 4308 is inserted adjacent to or along the lesser curvature 110. Next, a portion of the stomach 100 is tucked or pushed inwards towards the lesser curvature 110 until the bougie 4308 is reached (Step 4704). The bougie 4308 prevents the tucked-in portion 4302 from completely blocking off the stomach body 106, and allows for a channel to remain in the stomach body 106 after the stomach ligation procedure is completed. In another embodiment, a guidewire dilator, balloon dilator, or any other mechanism can be used to assist the healthcare professional in tucking in the stomach 100 without closing off the stomach body 106.

After the stomach 100 has been tucked-in, a ligation procedure is performed (Step 4706). The first untucked stomach portion 4304 and the second untucked stomach portion 4306 are ligated by inserting a ligature, such as bioabsorbable surgical staples, sutures, stitches, thread, wired and/or clamps, using a ligation device. Thus procedure closes off any space which was created by the tucked-in portion 4302 between the first untucked stomach portion 4304 and the second untucked stomach portion 4306. In another embodiment, the ligation procedure can be performed using bioabsorbable staples or stitches. The ligation procedure can be conducted either laparoscopically or during an open-surgical procedure. After the ligation procedure is completed, the bougie 4308 is removed from the stomach 100 (Step 4708) using the endoscopic device. In an embodiment, the stomach 100 is then covered with the gastric skirt 1902 (Step 4710), and the gastric skirt 1902 is filled or inflated to provide a desired level of constriction around the stomach (Step 4712).

Figure 44:
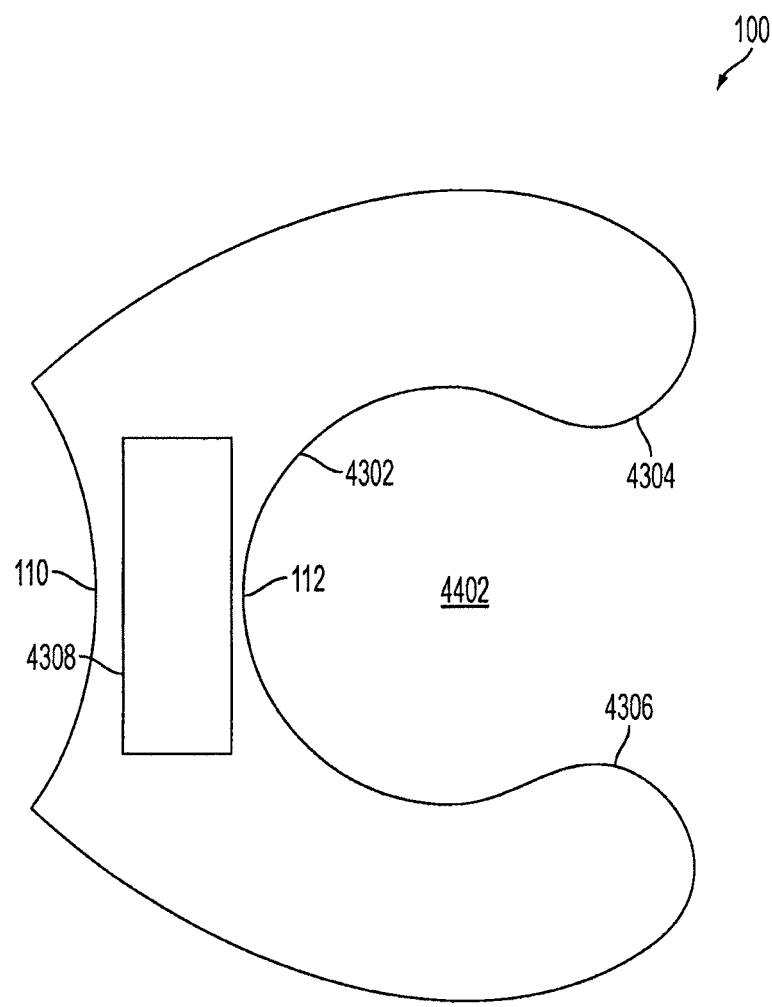
FIG. 44 is a lateral view of a tucked-in stomach prior to ligation.

FIG. 44 is a lateral view of a tucked-in stomach prior to ligation. The greater curvature 112 is tucked-in towards the lesser curvature 110, until the greater curvature 112 comes into contact with the bougie 4308. The tucked-in portion 4302 leaves the first untucked stomach portion 4304, the second untucked stomach portion 4306, and a cavity 4402 between the first untucked stomach portion 4304 and the second untucked stomach portion 4306.

Figure 45:
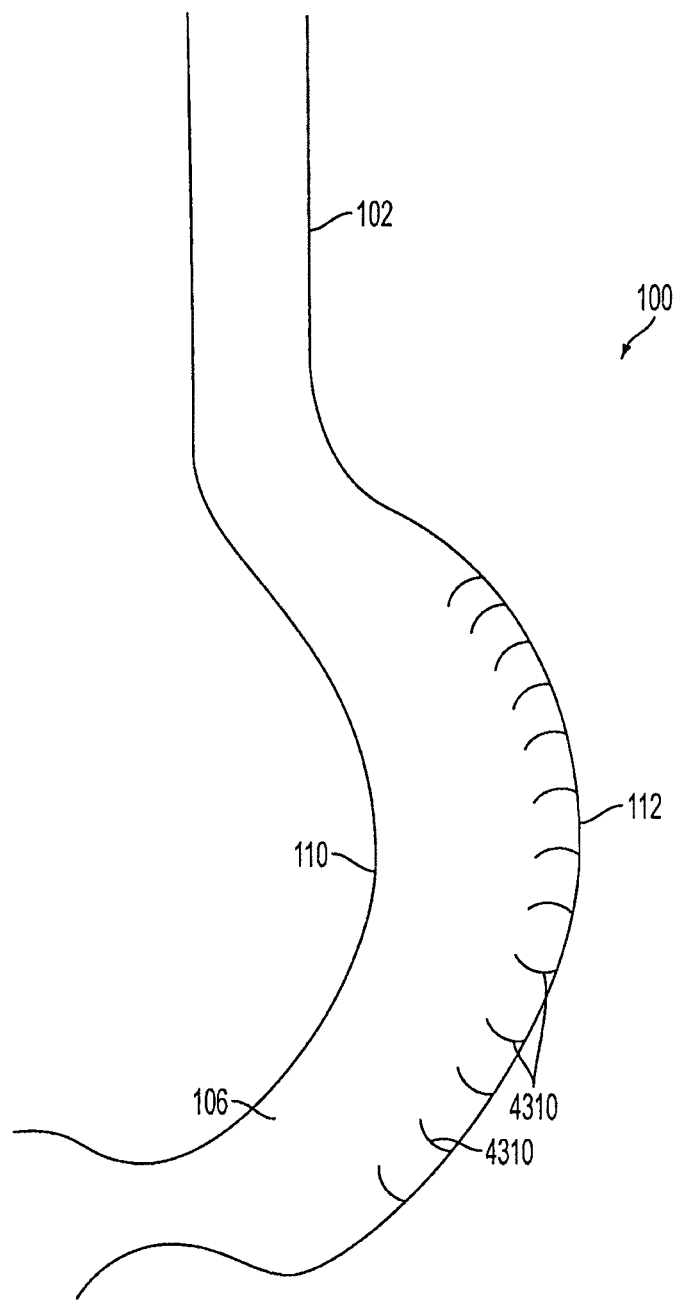
FIG. 45 is a view of a ligated stomach.

FIG. 45 is a view of a ligated stomach. After the ligation procedure is completed, the internal volume of the stomach 100 is reduced to approximately one-third of its original volume. The ligation procedure is reversible, as the sutures 4310 can be removed. In an embodiment, the gastric skirt 1902 is positioned around the ligated stomach as shown in FIG. 19. In another embodiment, the stomach 100 undergoes a VSG procedure instead of a ligation procedure prior to the gastric skirt 1902 being placed around the stomach.

Figure 46:
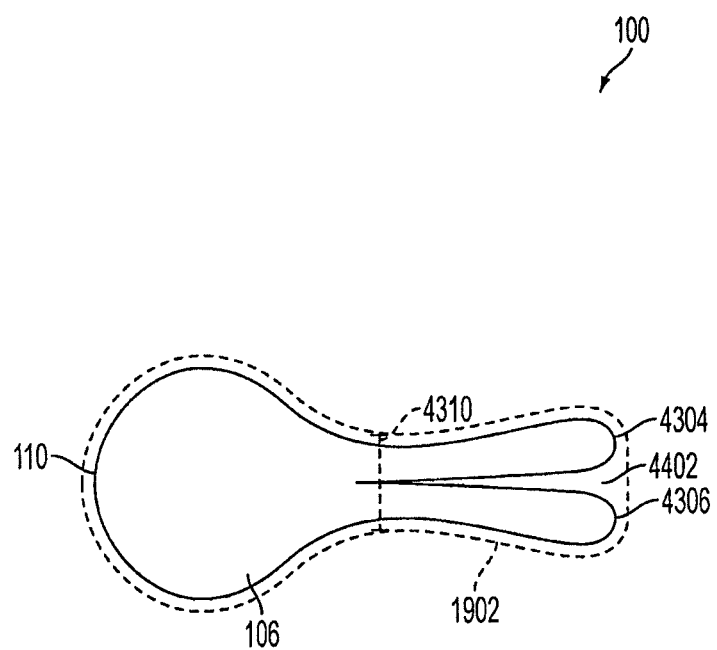
FIG. 46 is a lateral view of a gastric skirt positioned around a ligated stomach.
Figure 47:
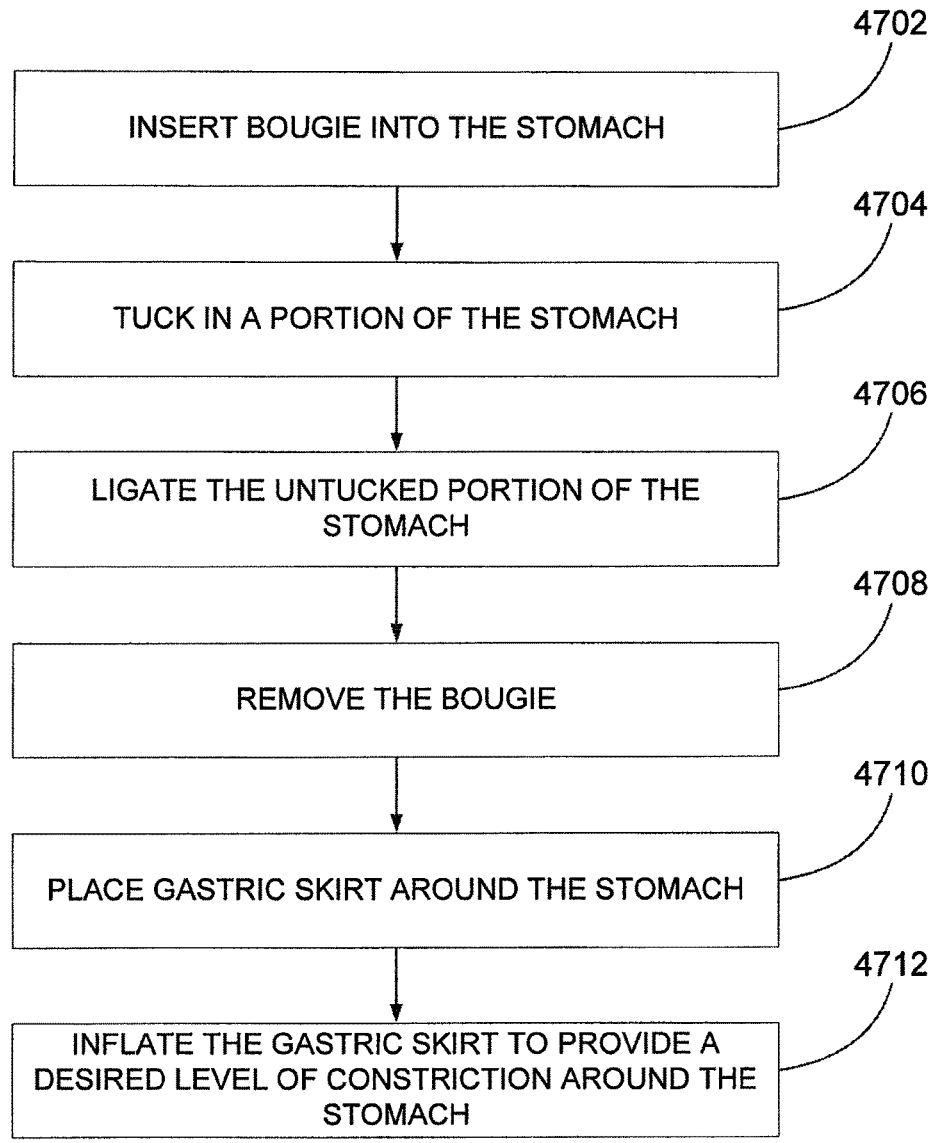
FIG. 47 is a flowchart illustrating a process of positioning a gastric skirt around a ligated stomach.

FIG. 46 is a lateral view of a gastric skirt positioned around a ligated stomach. The volume of the stomach body 106 is approximately one-third of its original volume. The sutures 4310 are inserted through the first untucked portion of the stomach 4304, the cavity 4402, and the second untucked portion of the stomach 4306. The sutures 4310 prevent food and stomach contents from entering and accumulating in the first untucked portion of the stomach 4304 and the second untucked portion of the stomach 4306. In an embodiment, the stomach 100 is covered with the gastric skirt 1902.

While the principles of the disclosure have been illustrated in relation to the exemplary embodiments shown herein, the principles of the disclosure are not limited thereto and include any modification, variation or permutation thereof.

What is claimed is:

1. A gastric restriction device for treating excessive weight or obesity in mammals, comprising:

a skirt having an interior surface and an exterior surface having a surface area of at least 14 square centimeters, the skirt having a left edge, a right edge, a top edge with a first indentation located at a center of the top edge, and a bottom edge with a second indentation located at a center of the bottom edge, the skirt having a narrow surface located between the first indentation and the second indentation and a broad surface formed from the left edge connecting to the right edge, the narrow surface operable to envelop a lesser curvature of an internal stomach organ of a mammal and the broad surface operable to envelop a greater curvature of the internal stomach organ;

a first attachment device attached to the right edge of the skirt; and a second attachment device attached to the left edge of the skirt and adapted to engage the first attachment device and maintain the left edge in proximity to the right edge.

2. The gastric restriction device of claim 1, wherein the skirt or the first and second attachment devices completely covers an entire area between the left edge and the right edge when the left edge is in proximity to the right edge and the first and second attachment devices are adapted to be positioned around the greater curvature of the internal stomach organ, thereby preventing expansion of the internal stomach organ when the first attachment device is fastened to the second attachment device.

3. The gastric restriction device of claim 1, wherein the skirt is adapted to be positioned around and in direct contact with the internal stomach organ of the mammal to tightly engage the internal stomach organ when the left edge is in proximity to the right edge.

4. The gastric restriction device of claim 1, wherein the top edge is a concave edge and the bottom edge is a concave edge.

5. The gastric restriction device of claim 1, wherein the skirt is made of an implantable silicon material or an ePTFE material.

6. A gastric constriction device for treating excessive weight or obesity in mammals, comprising:

a skirt including an interior surface and an exterior surface, the exterior surface with a surface area of at least 14 square centimeters, the skirt having a left edge, a right edge, a top edge, and a bottom edge, the top edge having a first indentation located at a center of the top edge, the bottom edge having a second indentation located at a center of the bottom edge, the skirt having a narrow surface located between the first indentation and the second indentation and a broad surface formed from the left edge connecting to the right edge, the narrow surface operable to cover a lesser curvature of a stomach of a mammal and the broad surface operable to cover a greater curvature of the stomach;

a first attachment device attached to the right edge of the skirt; and a second attachment device attached to the left edge of the skirt and adapted to engage the first attachment device and maintain the left edge in proximity to the right edge.

7. The gastric constriction device of claim 6, wherein the skirt or the first and second attachment devices completely covers an entire area between the left edge and the right edge when the left edge is in proximity to the right edge and the first and second attachment devices are adapted to be positioned around the greater curvature of the stomach, thereby preventing expansion of the stomach when the first attachment device is fastened to the second attachment device.

8. The gastric constriction device of claim 6, wherein the skirt is adapted to be positioned around and in direct contact with the stomach of the mammal to tightly engage the stomach when the left edge is in proximity to the right edge.

9. The gastric constriction device of claim 6, wherein the skirt is made of silicone.

10. The gastric constriction device of claim 6, wherein the skirt is made of a biodegradable and absorbable polymer.

11. The gastric constriction device of claim 6, wherein the skirt has a parallelogram shape.

12. The gastric constriction device of claim 6, wherein the first indentation has a concave shape and the second indentation has a concave shape.

* * * * *